US012110506B2

(12) United States Patent
Liu et al.

(10) Patent No.: US 12,110,506 B2
(45) Date of Patent: Oct. 8, 2024

(54) METHOD FOR CULTURING TUMOR INFILTRATING LYMPHOCYTES

(71) Applicants: SUZHOU GRIT BIOTECHNOLOGY CO., LTD., Shanghai (CN); SHANGHAI GRIT BIOTECHNOLOGY CO., LTD., Shanghai (CN); ZHUHAI TUOYU BIOTECHNOLOGY CO., LTD., Shanghai (CN); SHENZHEN GRIT BIOTECHNOLOGY CO., LTD., Shanghai (CN)

(72) Inventors: Yarong Liu, Shanghai (CN); Peipei Zhao, Shanghai (CN)

(73) Assignees: SUZHOU GRIT BIOTECHNOLOGY CO., LTD., Shanghai (CN); SHANGHAI GRIT BIOTECHNOLOGY CO., LTD., Shanghai (CN); ZHUHAI TUOYU BIOTECHNOLOGY CO., LTD., Shanghai (CN); SHENZHEN GRIT BIOTECHNOLOGY CO., LTD., Shanghai (CN)

(*) Notice: Subject to any disclaimer, the term of this patent is extended or adjusted under 35 U.S.C. 154(b) by 0 days.

(21) Appl. No.: 18/319,901

(22) Filed: May 18, 2023

(65) Prior Publication Data

US 2023/0303977 A1 Sep. 28, 2023

Related U.S. Application Data

(63) Continuation of application No. PCT/CN2021/131377, filed on Nov. 18, 2021.

(30) Foreign Application Priority Data

Nov. 19, 2020 (CN) .......................... 202011303703.3

(51) Int. Cl.
C12N 5/0783 (2010.01)
A61K 35/17 (2015.01)
A61P 35/00 (2006.01)

(52) U.S. Cl.
CPC ............ *C12N 5/0636* (2013.01); *A61K 35/17* (2013.01); *A61P 35/00* (2018.01); *C12N 2501/2302* (2013.01); *C12N 2501/515* (2013.01); *C12N 2502/11* (2013.01)

(58) Field of Classification Search
CPC .......... C12N 5/0636; C12N 2501/2302; C12N 2501/515; A61K 35/17
See application file for complete search history.

(56) References Cited

U.S. PATENT DOCUMENTS

| 8,383,099 | B2* | 2/2013 | Dudley .............. A61K 31/7076 435/372.3 |
|---|---|---|---|
| 2012/0244133 | A1 | 9/2012 | Rosenberg et al. |
| 2017/0044496 | A1 | 2/2017 | Sarnaik et al. |
| 2017/0107490 | A1 | 4/2017 | Maeurer |
| 2017/0246277 | A1 | 8/2017 | Schneck et al. |
| 2018/0228841 | A1 | 8/2018 | Frank et al. |
| 2019/0276802 | A1 | 9/2019 | Simpson-Abelson et al. |
| 2020/0164090 | A1 | 5/2020 | Yin et al. |
| 2024/0043801 | A1 | 2/2024 | Liu et al. |

FOREIGN PATENT DOCUMENTS

| CN | 106574244 A | 4/2017 |
|---|---|---|
| CN | 110042080 A | 7/2019 |
| CN | 110643574 A | 1/2020 |
| CN | 110938594 A | 3/2020 |
| CN | 111801415 A | 10/2020 |
| CN | 112040986 A | 12/2020 |
| CN | 112041433 A | 12/2020 |
| WO | WO 2015189357 A1 | 12/2015 |
| WO | WO 2019086711 A1 | 5/2019 |
| WO | WO 2019136459 A1 | 7/2019 |
| WO | WO 2019178420 A1 | 9/2019 |
| WO | WO 2019178421 A1 | 9/2019 |
| WO | WO 2019178422 A1 | 9/2019 |
| WO | WO 2020096927 A1 | 5/2020 |
| WO | WO 2020096988 A2 | 5/2020 |
| WO | WO 2020096988 A3 | 5/2020 |
| WO | WO 2020131547 A1 | 6/2020 |
| WO | WO 2020131547 A9 | 6/2020 |
| WO | WO 2020172202 A1 | 8/2020 |
| WO | WO 2020232029 A1 | 11/2020 |
| WO | WO 2021108455 A1 | 6/2021 |
| WO | WO 2021108727 A1 | 6/2021 |

(Continued)

OTHER PUBLICATIONS

Besser et al., Modifying interleukin-2 concentrations during culture improves function of T cells for adoptive immunotherapy, Cytotherapy, 11, 206-217, 2009. (Year: 2009).*
U.S. Appl. No. 18/269,407, filed Jun. 23, 2023, Liu et al.
Baldan et al., 2015, "Efficient and reproducible generation of tumour-infiltrating lymphocytes for renal cell carcinoma," Br. J. Cancer, 112(9):1510-1518.
International Searching Authority, English Translation of International Search Report and Written Opinion for International Patent Application No. PCT/CN2021/140841 (Pub No. WO 2022135525) mailed Mar. 23, 2022 (10 pages).
International Searching Authority, English Translation of Written Opinion for International Patent Application No. PCT/CN2021/131377 (Pub No. WO 2022105816) mailed Feb. 15, 2022 (6 pages).

(Continued)

*Primary Examiner* — Elly-Gerald Stoica
(74) *Attorney, Agent, or Firm* — JONES DAY

(57) ABSTRACT

A method for culturing tumor infiltrating lymphocytes (TIL), the method comprising co-culturing the expanded TIL with feeder cells after contacting the TIL with a T cell co-stimulatory molecule and/or a T cell growth factor for a period of time. In addition, further provided is a method for preventing and/or treating tumors by means of using the tumor infiltrating lymphocytes of the present application.

24 Claims, 23 Drawing Sheets

(56) References Cited

FOREIGN PATENT DOCUMENTS

| WO | WO 2021173964 A1 | 9/2021 |
|----|------------------|--------|
| WO | WO 2022135525 A1 | 6/2022 |
| WO | WO 2022223013 A1 | 10/2022 |
| WO | WO 2023011433 A1 | 2/2023 |

OTHER PUBLICATIONS

International Searching Authority, English Translation of International Search Report for International Patent Application No. PCT/CN2022/088338 (Pub No. WO 2022223013) mailed Jul. 22, 2022 (5 pages).
Jiang et al., 2014, In Vitro Culturing and Characteristics of Tumor-infiltrating Lymphocyte of Hepatocellular Carcinoma, 36(7):970-975, in Chinese with English abstract.
Santoiemma et al., 2015, "Tumor infiltrating lymphocytes in ovarian cancer," Cancer Biol. Ther., 16(6):807-820.
Tu, 2020, "Analysis of Cancerous Bloody Pleural Effusion TIL Cells In Vitro Culture," Smart Healthcare, 18(6):38-39, in Chinese with English abstract.
Wang, 2012, "Cytotoxicity Effect of T Cells Harbouring IL-15 on Hepatocellular Carcinoma Cell Line in vitro," Master Dissertation, College of Life Sciences, Zhejiang Sci-Tech University, Mar. 2012, in Chinese with English abstract (79 pages).
Zocchi et al., 1992, "Signalling in human tumour infiltrating lymphocytes: the CD28 molecule is functional and is physically associated with the CD45R0 molecule," Eur. J. Cancer, 28A(4-5):749-754.
International Searching Authority, English Translation of International Search Report for International Patent Application No. PCT/CN2021/131377 (Pub No. WO 2022105816) mailed Feb. 15, 2022 (4 pages).
Brinkman et al., 2014, "Easy quantitative assessment of genome editing by sequence trace decomposition," Nucleic Acids Res., 42(22):e168 (8 paegs).
Giordano et al., 2014, "The tumor necrosis factor alpha-induced protein 3 (TNFAIP3, A20) imposes a brake on antitumor activity of CD8 T cells," Proc. Natl. Acad. Sci. USA, 111(30):11115-11120.
International Searching Authority, English Translation of Written Opinion for International Patent Application No. PCT/CN2022/088338 (Pub No. WO 2022223013) mailed Jul. 22, 2022 (6 pages).
International Searching Authority, English Translation of International Search Report for International Patent Application No. PCT/CN2022/109577 (Pub No. WO 2023011433) mailed Oct. 31, 2022 (5 pages).
Verdeil et al., 2014, "Unleashing antitumor T-cell activation without ensuing autoimmunity: the case for A20-deletion in adoptive CD8+ T-cell therapy," Oncoimmunology, 3(10):e958951 (3 pages).

\* cited by examiner

METHOD FOR CULTURING TUMOR INFILTRATING LYMPHOCYTES

CROSS-REFERENCE TO RELATED APPLICATIONS

This application is a continuation of International Patent Application No. PCT/CN2021/131377, filed Nov. 18, 2021, which claims the benefit of priority to Chinese Patent Application No. 202011303703.3, filed Nov. 19, 2020, the contents of each of which is incorporated by reference herein in its entirety.

TECHNICAL FIELD

The present application relates to the field of biomedicine, and specifically to a method for culturing tumor infiltrating lymphocytes and a use thereof.

BACKGROUND OF THE INVENTION

Treating tumors by using adoptive autologous transferred tumor infiltrating lymphocytes is an effective approach to treat patients with poor prognosis. However, treating tumors by adoptive autologous transferred tumor infiltrating lymphocytes requires a large number of tumor infiltrating lymphocytes, and currently, the tumor infiltrating lymphocytes from patients' tumors have weak expansion abilities and poor cell functions. Therefore, how to provide a robust and reliable method for culturing tumor infiltrating lymphocytes is an urgent issue to be solved.

SUMMARY OF THE INVENTION

The present application provides a method for culturing tumor infiltrating lymphocytes, which has one or more effects selected from the group consisting of: increased number of TIL cells, enhanced cytokine secretion abilities, enhanced tumor cell killing abilities, improved proportion of T cell subpopulations, increased proportion of central memory T cells, decreased proportion of regulatory T cells, increased proportion of activated T cells, increased proportion of tumor-specific T cells, and increased proportion of stem cell-like T cells.

In one aspect, the present application provides a method for culturing tumor infiltrating lymphocytes (TILs), the method comprising co-culturing expanded TILs with feeder cells after contacting the expanded TILs with a T cell co-stimulatory molecule and/or a T cell growth factor for a period of time.

In one embodiment, the expanded TILs are TILs expanded in vitro.

In one embodiment, the expanded TILs are TILs obtained after subjecting the TILs, which are derived from tumor tissues and not expanded in vitro, to at least one stage of the in vitro expansion.

In one embodiment, compared to the TILs, which are derived from the tumor tissues and not expanded in vitro, the number of the expanded TILs is increased by at least 1-fold.

In one embodiment, wherein the expanded TILs are increased in number to at least 50-fold after the co-culture.

In one embodiment, wherein the number of the expanded TILs are increased to about 50-20000 folds after the co-culture.

In another aspect, the present application provides a method for culturing tumor infiltrating lymphocytes (TILs), wherein the method comprises subjecting the TILs, which are derived from tumor tissues and not expanded in vitro, to at least one stage of in vitro expansion, and wherein in a single stage of the in vitro expansion, the TILs expanded and/or not expanded in vitro are co-cultured with feeder cells after contacting with a T cell co-stimulatory molecule and/or a T cell growth factor for a period of time.

In one embodiment, in the first stage of in vitro expansion, the TILs not expanded in vitro are co-cultured with the feeder cells after contacting with the T cell co-stimulatory molecule and/or the T cell growth factor for the period of time.

In one embodiment, the TILs, which are derived from the tumor tissues and not expanded in vitro, are subjected to at least two stages of the in vitro expansion, and in the second stage of the in vitro expansion, the TILs expanded in vitro are co-cultured with the feeder cells after contacting with the T cell co-stimulatory molecule and/or the T cell growth factor for the period of time.

In one embodiment, the TILs, which are derived from the tumor tissues and not expanded in vitro, are subjected to the first and the second stages of the in vitro expansion, and in the second stage of the in vitro expansion, the TILs are co-cultured with the feeder cells.

In one embodiment, the first stage of in vitro expansion is carried out for at least about 7 days.

In one embodiment, the first stage of in vitro expansion is carried out for about 7 days to about 14 days.

In one embodiment, the second stage of the in vitro expansion is carried out for at least about 7 days.

In one embodiment, the second stage of the in vitro expansion is carried out for about 7 days to about 14 days.

In one embodiment, compared to co-culturing the TILs expanded and/or not expanded in vitro with the feeder cells and simultaneously contacting the TILs with the T cell co-stimulatory molecule and/or the T cell growth factor in a single stage of the in vitro expansion, co-culturing the TILs expanded and/or not expanded in vitro with the feeder cells after contacting the TILs with the T cell co-stimulatory molecule and/or the T cell growth factor for the period of time in a single stage of the in vitro expansion enhances the expansion effect of the TILs and/or shows improved TIL properties.

In one embodiment, the improved TIL properties comprise one or more properties selected from the group consisting of: increased number of TIL cells, increased proportion of viable cells, increased subsist abilities, improved proportion of T cell subpopulations, enhanced cytokine secretion abilities, enhanced tumor cell killing abilities, enhanced T cell receptor (TCR) clonal diversities and increased TIL cell number in tissues and/or tumors.

In one embodiment, the enhancing of the expansion effect of TILs comprises one or more selected from the group consisting of: increasing the number of TIL cells, changing the proportion of TIL cells, enhancing the secretion abilities of TIL cells, and enhancing the killing abilities of TIL cells.

In one embodiment, the changing of the proportion of TIL cells comprises one or more selected from the group consisting of: increasing the proportion of central memory T cells in TILs, decreasing the proportion of regulatory T cells, increasing the proportion of activated T cells, increasing the proportion of tumor-specific T cells, and increasing the proportion of stem cell-like T cells.

In one embodiment, the period of time is at least about 2 hours.

In one embodiment, the period of time is about 6-72 hours.

In one embodiment, the period of time is about 12-48 hours.

In one embodiment, the period of time is about 6, 12, 24, 48 or 72 hours.

In one embodiment, the TILs are co-cultured with the feeder cells after contacting with the T cell activator and/or the T cell growth factor for 12 hours or more.

In one embodiment, the TILs are co-cultured with the feeder cells after contacting with the T cell activator and/or the T cell growth factor for about 12 hours, about 24 hours, about 48 hours or about 72 hours.

In one embodiment, the T cell co-stimulatory molecule is selected from one or more of the group consisting of: CD80, CD86, B7-H3, 4-1BBL, CD27, CD30, CD134, B7h, CD40, LIGHT, an antibody that specifically binds to CD3, an antibody that specifically binds to CD28, an antibody that specifically binds to HVEM, an antibody that specifically binds to CD40L, an antibody that specifically binds to OX40, and an antibody that specifically binds to 4-1BB. For example, the T cell co-stimulatory molecule is selected from one or more of the group consisting of: cluster of differentiation 80 (CD80), CD86, CD276, 4-1BB ligand (4-1BBL), CD27, CD30, CD134, CD275, CD40, CD258, and functionally active fragments thereof. For example, the T cell co-stimulatory molecule is an agonist of one or more targets selected from the group consisting of: CD3, CD28, herpes virus entry mediator (HVEM), CD40L, OX40, and 4-1BB.

In one embodiment, the T cell activator comprises a CD3 agonist and/or a CD28 agonist.

In one embodiment, the T cell activator comprises a CD3 agonist.

In one embodiment, the T cell activator comprises an anti-CD3 antibody and/or an antigen-binding fragment thereof.

In one embodiment, the T cell activator comprises a CD28 agonist.

In one embodiment, the T cell activator comprises an anti-CD28 antibody and/or an antigen-binding fragment thereof, CD80 and/or a functionally active fragment thereof and/or CD86 and/or a functionally active fragment thereof.

In one embodiment, the T cell co-stimulatory molecule is an antibody that specifically binds to CD3.

In one embodiment, one of the T cell co-stimulatory molecules, or each of a plurality of the T cell co-stimulatory molecules is individually contacted with the TILs.

In one embodiment, a plurality of the T cell co-stimulatory molecules are contacted with the TILs simultaneously.

In one embodiment, one of the T cell co-stimulatory molecules, or each of a plurality of the T cell co-stimulatory molecules is individually added into the cell culture medium of the TILs separately.

In one embodiment, a plurality of the T cell co-stimulatory molecules are added simultaneously into the cell culture medium of the TILs.

In one embodiment, the one of the T cell co-stimulatory molecules is added into the cell culture medium of the TILs in one or more of the forms selected from the group consisting of: engineered cells expressing the T cell co-stimulatory molecule, nanoparticles comprising the T cell co-stimulatory molecule, and polymers comprising the T cell co-stimulatory molecule.

In one embodiment, the plurality of the T cell co-stimulatory molecules are added into the cell culture medium of the TILs in forms selected from the group consisting of: mixtures, fusion proteins, engineered cells expressing the plurality of the T cell co-stimulatory molecules, nanoparticles comprising the plurality of the T cell co-stimulatory molecules, and polymers comprising the plurality of the T cell co-stimulatory molecules.

In one embodiment, the T cell growth factor is one or more of the factors selected from the group consisting of: IL-2, IL-4, IL-7, IL-10, IL-12, IL-15, IL-21, and interferon gamma.

In one embodiment, the T cell growth factor is one or more of the factors selected from the group consisting of: IL-2, IL-7, IL-12, IL-15, IL-21, and interferon gamma.

In one embodiment, the T cell growth factor is IL-2 and/or a functionally active fragment thereof.

In one embodiment, the initial concentration of each of the T cell growth factors in the cell culture medium of the TILs is each independently at least about 300 IU/mL.

In one embodiment, the initial concentration of IL-2 in the cell culture medium of the TILs is at least 1000 IU/mL.

In one embodiment, one of the T cell growth factors, or each of a plurality of the T cell growth factors is individually contacted with the TILs.

In one embodiment, a plurality of the T cell growth factors are contacted with the TILs simultaneously.

In one embodiment, one of the T cell growth factors, or each of a plurality of the T cell growth factors is individually added into the cell culture medium of the TILs separately.

In one embodiment, a plurality of the T cell growth factors are added simultaneously into the cell culture medium of the TILs.

In one embodiment, the one of the T cell growth factors is added into the cell culture medium of the TILs in one or more of the forms selected from the group consisting of: engineered cells expressing the T cell growth factor, nanoparticles comprising the T cell growth factor, and polymers comprising the T cell growth factor.

In one embodiment, the plurality of the T cell growth factors are added into the cell culture medium of the TILs in one or more of the forms selected from the group consisting of: mixtures, fusion proteins, engineered cells expressing the plurality of the T cell growth factors, nanoparticles comprising the plurality of the T cell growth factors, and polymers comprising the plurality of the T cell growth factors.

In one embodiment, the TILs are TILs which are derived from fragments of tumor tissues and/or TILs which are derived from cryopreservation and resuscitation. In one embodiment, the TILs are TILs which are derived from fragments of the tumor tissue.

In one embodiment, the fragments have a volume of about 1-27 mm$^3$.

In one embodiment, the fragments have a volume of about 27 mm$^3$.

In one embodiment, the feeder cells comprise antigen presenting cells.

In one embodiment, the feeder cells comprise one or more of the cells selected from the group consisting of: peripheral mononuclear cells, dendritic cells, and artificial antigen presenting cells.

In one embodiment, the feeder cells are peripheral mononuclear cells.

In one embodiment, the feeder cells are irradiated feeder cells.

In one embodiment, the co-culture of the TILs with the feeder cells comprises contacting the surfaces of the feeder cells with the surfaces of the TILs.

In one embodiment, the co-culture of the TILs with the feeder cells comprises adding the feeder cells into the cell culture medium of the TILs.

In one embodiment, the feeder cells are added into the cell culture medium of the TILs at a proportion of the feeder cells to the TILs from about 40:1 to about 400:1.

In another aspect, the present application provides a tumor infiltrating lymphocyte (TIL) obtainable by the method described in the present application.

In another aspect, the present application provides a composition comprising TILs described in the present application.

In another aspect, the application provides a pharmaceutical composition comprising TILs described in the present application and/or a composition described in the present application, and optionally a pharmaceutically acceptable carrier.

In another aspect, the present application provides a method for affecting tumor cell growth, comprising administering to a subject TILs described in the present application and/or a pharmaceutical composition described in the present application. For example, the method for affecting tumor cell growth can be an in vitro method. For example, the method for affecting tumor cell growth can be an ex vivo method. For example, the method for affecting tumor cell growth can be a method for non-diagnostic and non-therapeutic purposes. For example, the method for affecting tumor cell growth can be a method for non-therapeutic purposes. For example, the method for affecting tumor cell growth can be a method for non-diagnostic purposes.

In another aspect, the present application provides use of the TILs described in the present application and/or the pharmaceutical composition described in the present application for the manufacture of a medicament for preventing and/or treating tumors.

In one embodiment, the tumors are selected from solid tumors.

In one embodiment, the tumors are one or more of the tumors selected from the group consisting of: melanoma, ovarian cancer, cervical cancer, lung cancer, bladder cancer, breast cancer, head and neck cancer, pancreatic cancer, liver cancer, stomach cancer, colorectal cancer, and kidney cancer.

In another aspect, the present application provides a method for preventing and/or treating tumors, comprising administering to a subject a TIL described in the present application and/or a pharmaceutical composition described in the present application.

In one embodiment, the tumors are selected from solid tumors.

In one embodiment, the tumors are one or more of the tumors selected from the group consisting of: melanoma, ovarian cancer, cervical cancer, lung cancer, bladder cancer, breast cancer, head and neck cancer, pancreatic cancer, liver cancer, stomach cancer, colorectal cancer, and kidney cancer.

In another aspect, the present application provides a TIL described in the present application and/or a pharmaceutical composition described in the present application for use in preventing and/or treating tumors.

In another aspect, the present application provides a TIL described in the present application and/or a pharmaceutical composition described in the present application for use in preventing and/or treating tumors, wherein the tumors are selected from solid tumors.

In another aspect, the present application provides a TIL described in the present application and/or a pharmaceutical composition described in the present application for use in preventing and/or treating tumors, wherein the tumors are one or more of the tumors selected from the group consisting of: melanoma, ovarian cancer, cervical cancer, lung cancer, bladder cancer, breast cancer, head and neck cancer, pancreatic cancer, liver cancer, stomach cancer, colorectal cancer, and kidney cancer.

Other aspects and advantages of the present application can be readily perceived by those skilled in the art from the following detailed description. In the following detailed description, only exemplary embodiments of the present application are shown and described. As will be recognized by those skilled in the art, the content of the present application enables those skilled in the art to make changes to the disclosed specific embodiments without departing from the spirit and scope of the invention involved in the present application. Correspondingly, the drawings and descriptions in the specification of the present application are merely exemplary, rather than restrictive.

BRIEF DESCRIPTION OF THE DRAWING

The specific features of the invention involved in the present application are as shown in the appended claims. The characteristics and advantages of the invention involved in the present application can be better understood by referring to the exemplary embodiments described in detail below and the accompanying drawings. A brief description of the drawings is as below:

DETAILED DESCRIPTION

Figure 1:
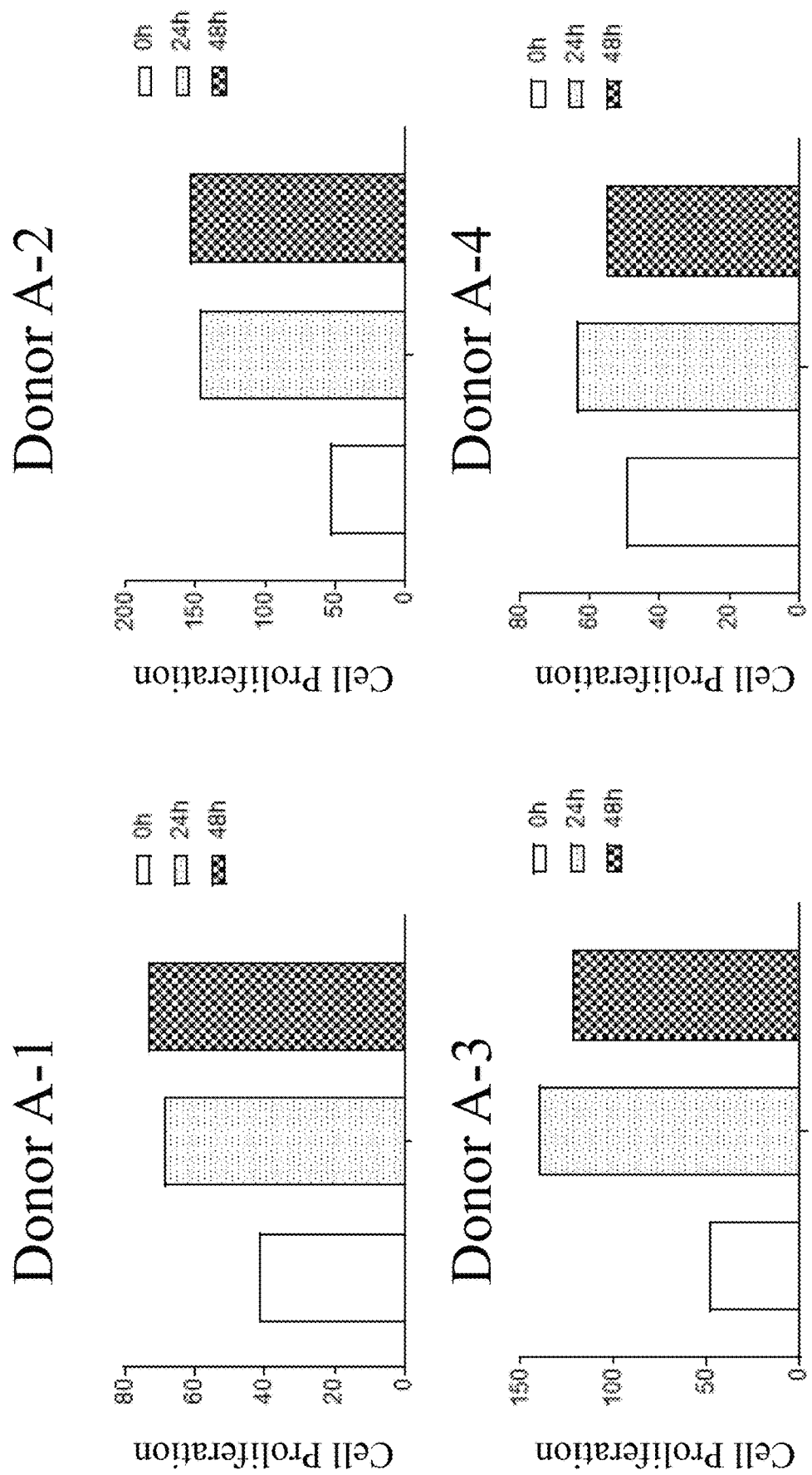
FIG. 1 shows for donors A-1, A-2, A-3 and A-4, the comparison of the proliferation abilities of TILs when cultured with feeder cells added at 0, 24 or 48 hours after addition of OKT3 and IL-2.

The implementation of the present application will be illustrated below by specific examples, and other advantages and effects of the present application will be easily known by those familiar with the art from the contents disclosed in the specification.

DEFINITION OF TERMS

In the present application, the term "expression" generally refers to the processes of transcription and/or translation of a gene encoding a polypeptide of interest that occur within a cell. The transcription level of a gene encoding a polypeptide of interest in a host cell can be determined by measuring the amount of the corresponding mRNA present in the cell. For example, quantitative measurement of an mRNA transcribed from a gene encoding a polypeptide of interest can be carried out by PCR or by RNA hybridization (see Sambrook et al., Molecular Cloning: A Laboratory Manual, ColdSpring Harbor Laboratory Press (1989)). The translation level of a gene encoding a polypeptide of interest can be measured by a variety of methods, e.g., by ELISA, by polypeptide biological activity assays, or by protein blotting or radioimmuno assays (see Sambrook et al., supra).

In the present application, the "stage" in the terms "one stage of in vitro expansion", "a single stage of in vitro expansion", or "the first stage of in vitro expansion", etc. generally refers to a process of expansion that TILs are subjected to in vitro. In one embodiment, each stage can be divided by the change in the number of TIL cells. In one embodiment, when the number of the TIL cells is increased by at least about 1-fold, it can be considered that the TIL cells enter the next stage of in vitro expansion. In some embodiments, when the number of the TIL cells is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 30-fold, at least about 40-fold, or at least about 50-fold, it can be considered that the TIL cells enter the next stage of the in vitro expansion. In one embodiment, each stage can also be divided by the culture conditions of the TIL cells. In one embodiment, after T cell co-stimulatory molecules and/or T cell growth factors are added or supplemented into the cell culture medium, it can be considered that the TIL cells enter the next stage of the in vitro expansion. In one embodiment, after TIL cells have been centrifuged and/or washed, it can be considered that the TIL cells enter the next stage of the in vitro expansion. In one embodiment, each stage can also be divided by the culture days of the TIL cells. In one embodiment, after the TIL cells have been cultured in vitro for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 30 days, about 40 days, about 50 days or about 100 days, it can be considered that the TIL cells enter the next stage of the in vitro expansion.

In the present application, the term "the first stage of in vitro expansion" generally refers to a stage of expansion using T cell growth factors after primary TILs are obtained from tissues. In one embodiment, the tissues can be tumor tissues. In one embodiment, the expansion can be autologous or allogeneic in vivo expansion, or can be in vitro expansion. The first stage of the expansion can also be referred to as a preREP (pre-rapid expansion protocol) stage.

In the present application, the term "the second stage of in vitro expansion" generally refers to a stage of expansion again, after a tissue has been removed from a subject and expanded. In one embodiment, compared to the TILs subjected to the first stage of in vitro expansion, the number of the TIL cells subjected to the second stage of in vitro expansion is increased, e.g., can be increased by at least about 10-fold (or at least about 20, 30, 40, 50, 60, 70, 80 or 90-fold), or in one embodiment, the cell number can be increased by at least about 100-fold. In one embodiment, the second and the first stages of the expansion can be different in culture conditions, e.g., the culture materials added can be different. The second stage of the expansion can also be referred to as a REP (rapid expansion protocol) stage.

In the present application, the term "in vivo" generally refers to an event that occurs in the body of a subject.

In the present application, the term "in vitro" generally refers to an event that occurs outside the body of a subject.

In the present application, the term "ex vivo" generally refers to an event that involves a treatment or surgery on cells, tissues and/or organs which have been removed from a subject. In one embodiment, the cells, tissues and/or organs can be returned into the subject's body by a surgery or treatment method.

In the present application, the term "secretion" generally refers to transfer of an expressed polypeptide or protein by a cell to the extracellular environment.

In the present application, the term "secretion ability" generally refers to an ability of a cell to express a polypeptide or protein and to transfer the polypeptide or protein to the extracellular environment.

In the present application, the term "irradiation" generally refers to process of a substance by means of radiation. For example, in one embodiment, irradiation can refer to irradiating a substance with X-rays, alpha rays, beta rays, or gamma rays.

In the present application, the term "engineered cells" generally refers to cells which have been genetically modified by adding additional genetic material in the form of DNA or RNA to the total genetic material of the cells. In one embodiment, the engineered cells can be TILs genetically modified to express the T cell co-stimulatory molecules and/or the T cell growth factors according to the present application.

In the present application, the term "co-culture" generally refers to culturing two or more different populations of cells with some degree of contact between them. The "contact" between the two or more different populations of cells, in one embodiment, can be by direct contact, i.e., the cells of one population are directly physically contacted with the cells of another population. Alternatively, in one embodiment, the contact can be by indirect contact mediated by sharing a culture medium. The shared medium can contain metabolites produced and released by at least one population of co-cultured cells, and be used to culture the cells of another population.

In the present application, the term "contact" generally means that two or more substances of different types are brought into contact together in any order, in any manner, and for any length of time. In one embodiment, the contact can be by direct contact, for example, feeder cells, T cell co-stimulatory molecules and/or T cell growth factors can be added into the culture medium of TIL cells. In one embodiment, the contact can be by indirect contact, for example, metabolites produced and released by a feeder cell can be used to culture a TIL cell.

In the present application, the term "mixture" generally refers to a combination of two or more different substances.

In the present application, the terms "simultaneous contact", "concurrent contact", "while contacting with", "simultaneously" and "concurrently" generally refer to the administration of two or more substances to a subject such that the substances are present in the subject and the environment in which the subject is cultured at the same time. Simultaneous contact can include administration of different compositions at the same time, administration of different compositions at different times, or administration of a composition in which two or more active pharmaceutical ingredients are present.

In the present application, the term "expansion" generally refers to a several-fold increase in the number of cells over a period of time. In one embodiment, the cell number can be increased by at least about 3-fold (or 4, 5, 6, 7, 8 or 9-fold). In one embodiment, the cell number can be increased by at least about 10-fold (or 20, 30, 40, 50, 60, 70, 80 or 90-fold). Alternatively, in one embodiment, the cell number can be increased by at least about 100-fold. In the present application, the term "expanded" generally means that the cells have been subjected to one or more of the expansions described above.

In the present application, the term "polymer" generally refers to a molecule composed of individual chemical moieties linked together, which moieties can be the same or different. In one embodiment, the term "polymer" can refer to individual chemical moieties linked tail to tail to form a linear molecule, as well as individual chemical moieties linked together in the form of branched (e.g., "multi-arm" or "star") structures. In one embodiment, a polymer can include, for example, hydrogel, polyethylene glycol, or poloxamer. Poloxamer is a nonionic triblock copolymer with a central hydrophobic chain of polyoxypropylene (poly (propylene oxide)) and two pendant hydrophilic chains of polyoxyethylene (poly(ethylene oxide)). The substances encompassed in the present application may be formulated with, or administered with, any polymers described herein or known in the art.

In the present application, the term "antibody" generally refers to an immunoglobulin reactive to a specified protein or peptide or fragment thereof. Such antibodies include, but are not limited to, human antibodies, primatized antibodies, chimeric antibodies, monoclonal antibodies, monospecific antibodies, polyclonal antibodies, multispecific antibodies, nonspecific antibodies, bispecific antibodies, multispecific antibodies, humanized antibodies, synthetic antibodies, recombinant antibodies, hybrid antibodies, mutant antibodies, graft-conjugated antibodies (i.e., antibodies conjugated or fused to other proteins, radiolabels, cytotoxins), and antibodies produced in vitro. The antibody can be antibodies from any class, including but not limited to IgG, IgA, IgM, IgD, and IgE, and antibodies from any subclass (e.g., IgG1, IgG2, IgG3, and IgG4). The antibody can have a heavy chain constant region selected from, e.g., IgG1, IgG2, IgG3, or IgG4. The antibody can also have a light chain selected from, e.g., kappa (κ) or lambda (k). The antibody can be derived from any species, including but not limited to mice, human, camel, llama, fish, shark, goat, rabbit, chicken, and cattle. The constant region of the antibody can be altered, e.g., mutated, to modify the properties of the antibody (e.g., to enhance or decrease one or more of the following: the Fc receptor binding, the antibody glycosylation, the number of cysteine residues, the effector cell function, or the complement function). In general, the antibody specifically binds to a predetermined antigen, e.g., an antigen associated with a disorder, e.g., an inflammatory, an immune, an autoimmune, a neurodegenerative, a metabolic, and/or a malignant disorder.

In the present application, the term "anti-CD3 antibody" generally refers to an antibody or variant thereof targeting CD3, e.g., a monoclonal antibody, including a human, humanized, chimeric or murine antibody, which are against the CD3 receptors in the T cell antigen receptors of mature T cells. The anti-CD3 antibody can include OKT-3. The anti-CD3 antibody can also include other anti-CD3 antibodies including, for example, in one embodiment otelixizumab, teplizumab, and visilizumab.

In the present application, the term "IL-2" or "IL2" generally refers to a T cell growth factor known as interleukin 2, and includes all forms of IL-2, which can include in one embodiment human and mammalian forms, conservative amino acid substitutions, glycoform modifications or variants, or active fragments thereof. The GeneID of the gene encoding the IL2 can be 3558.

In the present application, the term "antigen presenting cell" or "APC" generally refers to an immune system cell which displays on its surface an exogenous antigen complexed with a major histocompatibility complex (MHC), such as a helper cell (e.g., a B cell, a dendritic cell, etc.). T cells can recognize these complexes using their T cell receptors (TCRs). APCs can process antigens and present them to T cells. In one embodiment, the antigen presenting cells can be selected from the group consisting of: peripheral mononuclear cells, dendritic cells, and artificial antigen presenting cells.

In the present application, the term "TIL properties" generally refers to properties of TIL cells obtained by the culturing method of the present application. Changes in the TIL properties can comprise: increased number of TIL cells, increased proportion of viable cells, increased subsist abilities, improved proportion of T cell subpopulations, enhanced cytokine secretion abilities, enhanced tumor cell killing abilities, enhanced T cell receptors (TCRs) clonal diversities and enhanced TIL cell number in tissues and/or tumors, or any combination thereof. Changes of the present application can be increased or decreased. In the present application, the term "expansion effect" generally refers to an effect that occurs after cells have been expanded. Changes in the expansion effect can include changes in the number and/or proportion of cells, changes in secretion ability, changes in killing ability, or changes in expression ability, or any combination thereof. The changes can be enhancement or reduction.

In the present application, the term "expanded" generally refers to being cultured to produce changes in the number of cells, and expanded cells can also produce changes in the number and/or proportion of cells, changes in secretion ability, changes in killing ability or changes in expression ability, or any combination thereof. The changes can be increased or decreased.

In the present application, the term "nanoparticle" generally refers to at least one microscopic particle having a size of less than 100 nm. In general, nanoparticles have diameters in the range of 50 nm to 500 nm (i.e., 0.05 m to 0.5 m); are structurally stable in physiological environments; and can accommodate smaller molecules (such as drugs or other bioactive agents), and then can deliver the molecules to desired sites.

In the present application, the term "artificial antigen presenting cell" generally refers to an artificially constructed immune system cell for displaying an exogenous antigen complexed with a major histocompatibility complex (MHC). In one embodiment, the isolated artificial antigen presenting cells (aAPCs) can be included, which can comprise cells expressing HLA-A/B/C (the GeneID of the gene encoding it can be 3105, 3106 or 3107), CD64 (the GeneID of the gene encoding it can be 2209), CD80 (the GeneID of the gene encoding it can be 941), ICOS-L (the GeneID of the gene encoding it can be 23308) and CD58 (the GeneID of the gene encoding it can be 965), and can be modified to express more than one co-stimulatory molecules, wherein the above can include the numbers themselves.

In the present application, the term "fusion protein" generally refers to a polypeptide or protein containing the amino acid sequence of a first polypeptide or protein or fragment, analog or derivative thereof, as well as the amino acid sequence of a heterologous polypeptide or protein (i.e., a second polypeptide or protein or fragment, analog or derivative thereof that is different from the first polypeptide or protein or fragment, analog or derivative thereof, or a fraction that is generally not the first polypeptide or protein or fragment, analog or derivative thereof). In some cases, the fusion protein can include a prophylactic or therapeutic medicament fused to a heterologous protein, polypeptide or peptide. Wherein, the heterologous protein, polypeptide or peptide can or may not be different types of prophylactic or therapeutic medicaments. For example, two different proteins, polypeptides or peptides with immunomodulatory activities can be fused together to form a fusion protein. In some cases, compared to the activity of the original polypeptide or protein before being fused with the heterologous protein, polypeptide or protein, the fusion protein may have retained or enhanced activity.

In the present application, the term "killing ability" generally refers to an ability achieved by killing target cells by means of contacting the cells with an effective amount of substances. In one embodiment, the substances can be TIL cells. The killing can include killing cells by autologous CDC, apoptosis, ADCC, and/or phagocytosis, or by promoting these mechanisms of other cells or substances, or by a combination of two or more of these mechanisms.

In the present application, the term "administration" generally refers to delivery of a substance to a subject in need thereof by any route known in the art. Pharmaceutical carriers and preparations or compositions are also well known in the art. Administration routes can include: intravenous, intramuscular, intradermal, subcutaneous, transdermal, mucosal, intratumoral and/or mucosal.

In the present application, the term "kit" generally refers to two or more components packaged together in a container, receptacle or other container, one of which corresponds to the substance of the present application. For example, the TIL cells of the present application are included.

In the present application, the term "subject" generally refers to a cell or an animal, which can be a mammal such as human, a non-human primate (ape, gibbon, gorilla, chimpanzee, orangutan, and macaque), a domestic animal (dog and cat), a farm animal (a poultry such as chicken and duck, horse, cattle, goat, sheep, and pig) and a laboratory animal (mouse, rat, rabbit, and guinea pig). The human subject includes a fetal, a neonatal, an infant, an adolescent and an adult subject. The subject includes an animal disease model, e.g., a tumor animal model, and other animal models known to those skilled in the art.

In the present application, the term "kit" generally refers to two or more components packaged together in a container, receptacle or other container, one of which corresponds to the substance of the present application. For example, TIL cells of the present application are comprised.

In the present application, the term "feeder cell" generally refers to a cultured cell that grows in vitro and secretes at least one factor into the culture medium and can be used to support the growth of another cell of interest in culture. In one embodiment, the feeder cells can include antigen presenting cells.

In the present application, the term "specific binding" generally refers to an antibody that recognizes a specific antigen, but does not substantially recognize or bind to other molecules in a sample. For example, if an antibody can specifically bind to the specific antigen from one species, the antibody can also specifically bind to the antigen or a homologous antigen from one or more other species. Such interspecies reactivities themselves may not alter the classification of the antibody as specific. In some cases, an antibody that specifically binds to an antigen can also bind to different allelic forms of the antigen.

In the present application, the term "complete culture process" generally refers to a complete process starting from the isolation of cells from tumor tissues isolated from a patient, through one or more expansions, and finally obtaining cells that can be administered to a subject.

In the present application, the term "cell culture medium" generally refers to a nutrient solution in which cells, for example mammalian cells, are grown. The formulation of the cell culture medium is well known in the art. Typically, the cell culture medium includes buffers, salts, carbohydrates, amino acids, vitamins, and essential trace elements. The cell culture medium may or may not contain serum, peptone, and/or protein. The cell culture medium can be supplemented with additional components or increased concentration of components, such as amino acids, salts, sugars, vitamins, hormones, growth factors, buffers, antibiotics, lipids, trace elements, etc., depending on the requirements of cells to be cultured and/or desired cell culture parameters.

In the present application, the term "pharmaceutical preparation" or "pharmaceutical composition" generally refers to a preparation that allows the biological activity of the active ingredient to be effective, and that can be free of additional components that are unacceptably toxic to the subject to whom the preparation will be administered. Such preparations are sterile. "Pharmaceutically acceptable" excipients (carriers, additives) are those that can be reasonably administered to a subject mammal to provide an effective dose of the active ingredient used.

In the present application, the term "tumor infiltrating lymphocyte" or "TIL" generally refers to a population of cells initially obtained as leukocytes that have left the bloodstream of a subject and migrated into a tumor. TILs can include, but are not limited to, $CD8^+$ cytotoxic T cells (lymphocytes), Th1 and Th17$CD4^+$T cells, natural killer cells, dendritic cells, and M1 macrophages. TILs can include primary TILs and secondary TILs. The "primary TILs" can be those TIL cells obtained from a tissue sample of a subject. The "secondary TILs" can be any TIL cell population that has been expanded or expanded in the present application. In some embodiments, the tumor infiltrating lymphocytes may not be isolated or purified, or may be infiltrated with tumor cells. In one embodiment, the TILs of the present application can refer to a population of TIL cells.

In the present application, "$CD4^+$ cells" generally refer to CD4-positive cells, which can be T cells, for example. The terms "$CD4^+$ cell", "CD4-positive cell" can be used synonymously. These cells can be identified by methods known in the art, for example by staining the cells with fluorescently labeled antibodies against CD4 and using fluorescence-activated cell sorting. For example, existing data can demonstrate that an increase in the proportion of $CD4^+$ cells can increase the abilities of cell populations to secrete IFN-γ and/or TNF, and can enhance the tumor suppressor effects of T cell populations. For example, see Tay, R. E., Richardson, E. K. et al. (2020). Cancer Gene Therapy, 1-13. However, there is a lack of a method for increasing the proportion of $CD4^+$ cells in the art, and the present application can provide a method for affecting the proportion of $CD4^+$ cells.

In the present application, "$CD8^+$ cells" generally refer to CD8-positive cells, which can be T cells, for example. The terms "$CD8^+$ cell", "CD8-positive cell" can be used synonymously. These cells can be identified by methods known in the art, for example by staining the cells with fluorescently labeled antibodies against CD8 and using fluorescence-activated cell sorting.

In the present application, the term "central memory T cell" generally refers to T cells that have long-term memory and are able to be restimulated by antigens. The central memory T cells can have phenotypes of $CD45RA^-CCR7^+$. For example, the central memory T cells can be identified by $CD45RA^-$ and $CCR7^+$. Alternatively, for example, the central memory T cells can have phenotypes of $CD45RO^+$ $CD62L^+$, for example, the central memory T cells can be identified by $CD45RO^+$ and $CD62L^+$. The central memory T cells can have a stronger anti-tumor growth ability than ordinary T cells.

In the present application, the term "regulatory T cell" generally refers to a subpopulation of T cells that control autoimmune reactivities in the body. Regulatory T cells can have phenotypes of $CD4^+CD25^+Foxp3^+$, for example, the regulatory T cells can be identified by $CD4^+$, $CD25^+$ and $Foxp3^+$. The regulatory T cells can have abilities to suppress the anti-tumor growth of T cells.

In the present application, the term "activated T cell" generally refers to T cells that have been activated to have abilities to resist tumor growth. The activated T cells can have phenotypes of $PD1^+$, $LAG3^+$ or $CD28^+$, for example, the activated T cells can be identified by $PD1^+$, $LAG3^+$ or $CD28^+$. The activated T cells can have abilities to resist tumor growth.

In the present application, the term "tumor-specific T cell" generally refers to T cells that can specifically resist tumor growth. The tumor-specific T cells can have phenotypes of $CD103^+CD39^+$. For example, the tumor-specific T cells can be identified by $CD103^+$ and $CD39^+$. The tumor-specific T cells can have more specific anti-tumor growth abilities than ordinary T cells.

In the present application, the term "stem-like T cells" generally refers to a class of T cells that can have the potential to self-proliferate and/or differentiate. The stem-like T cells can have phenotypes of $TCF1^+$, for example, the stem-like T cells can be identified by $TCF1^+$. The tumor-specific T cells can have stronger and/or longer-term anti-tumor growth abilities than normal T cells.

In the present application, the term "NK cell" is also referred to as "natural killer cell", and generally refers to a cell with large granules in the cytoplasm. NK cells are developed from bone marrow lymphoid stem cells and can differentiate and develop depending on the bone marrow or thymus microenvironment. In the present application, the proportion of NK cells in TIL cells can be altered by the methods of the present application.

In the present application, the term "tumor fragment" generally refers to tumor fragments that can be formed by fragmentation after tumor tissue is removed from a subject.

In the present application, the term "composition" or "pharmaceutical composition" generally refers to at least one cell, and at least one and optionally more than one other pharmaceutically acceptable chemical components such as the mixture of carriers, stabilizers, diluents, dispersing agents, suspending agents, thickening agents and/or excipients.

In the present application, the term "pharmaceutically acceptable carrier" generally refers to one or more non-toxic materials that do not interfere with the effectiveness of the biological activity of the active ingredient. Such preparations can conventionally contain salts, buffers, preservatives, compatible carriers, and optionally other therapeutic agents. Such pharmaceutically acceptable preparations can also contain compatible solid or liquid fillers, diluents or encapsulating substances suitable for administration to humans. Other contemplated carriers, excipients, and/or additives that can be used in the formulations described herein can include, for example, flavoring agents, antimicrobial agents, sweeteners, antioxidants, antistatic agents, lipids, protein excipients (such as serum albumin, gelatin, and casein), salt-forming counterions (such as sodium), and the like. These and other known pharmaceutical carriers, excipients and/or additives suitable for use in the formulations described herein are known in the art.

In the present application, the term "T cell co-stimulatory molecule" generally refers to a ligand that binds to the corresponding binding receptor on a T cell and mediates a T cell co-stimulatory response. The co-stimulatory molecules can be cell surface molecules other than an antigen receptor or its ligand required for an effective immune response. Costimulatory molecules can include, but are not limited to, MHC class I molecules, TNF receptor proteins, immunoglobulin-like proteins, cytokine receptors, integrins, signaling lymphocyte activation molecules (SLAM proteins), NK cell activation receptors, BTLA (the GeneID of the gene encoding it can be 151888), Toll ligand receptors, OX40 (the GeneID of the gene encoding it can be 7293), CD2 (the GeneID of the gene encoding it can be 914), CD7 (the GeneID of the gene encoding it can be 924), CD27 (the GeneID of the gene encoding it can be 939), CD28 (the GeneID of the gene encoding it can be 940), CD30 (the GeneID of the gene encoding it can be 943), CD40 (the GeneID of the gene encoding it can be 958), CDS, ICAM-1 (the GeneID of the gene encoding it can be 3383), LFA-1 (CD11a/CD18) (the GeneID of the gene encoding it can be 3689), 4-1BB (CD137) (the GeneID of the gene encoding it can be 3604), B7-H3 (the GeneID of the gene encoding it can be 80381), ICOS (CD278) (the GeneID of the gene encoding it can be 29851), GITR (the GeneID of the gene encoding it can be 8784), BAFFR (the GeneID of the gene encoding it can be 115650), LIGHT (the GeneID of the gene encoding it can be 8740), HVEM (LIGHTR) (the GeneID of the gene encoding it can be 8764), KIRDS2, SLAMF7 (the GeneID of the gene encoding it can be 57823), NKp80 (KLRF1) (the GeneID of the gene encoding it can be 51348), NKp44 (the GeneID of the gene encoding it can be 9436), NKp30 (the GeneID of the gene encoding it can be 259197), NKp46 (the GeneID of the gene encoding it can be 9437), CD19 (the GeneID of the gene encoding it can be 930), CD4 (the GeneID of the gene encoding it can be 920), CD8a (the GeneID of the gene encoding it can be 925), CD80 (the GeneID of the gene encoding it can be 926), IL-2Rβ, IL-2Rγ, IL7Rα (the GeneID of the gene encoding it can be), ITGA4 (the GeneID of the gene encoding it can be 3676), VLA1 (the GeneID of the gene encoding it can be 3672), CD49a (the GeneID of the gene encoding it can be 3672), IA4 (the GeneID of the gene encoding it can be 3732), CD49D (the GeneID of the gene encoding it can be 3676), ITGA6 (the GeneID of the gene encoding it can be 3655), VLA-6 (the GeneID of the gene encoding it can be 3655), CD49f (the GeneID of the gene encoding it can be 3655), ITGAD (the GeneID of the gene encoding it can be 3681), CD11d (the GeneID of the gene encoding it can be 3681), ITGAE (the GeneID of the gene encoding it can be 3682), CD103 (the GeneID of the gene encoding it can be 3682), ITGAL (the GeneID of the gene encoding it can be 3683), CD11a (the GeneID of the gene encoding it can be 3683), LFA-1 (the GeneID of the gene encoding it can be 3683), ITGAM (the GeneID of the gene encoding it can be 3684), CD11b (the GeneID of the gene encoding it can be 3684), ITGAX (the GeneID of the gene encoding it can be 3687), CD11c (the GeneID of the gene encoding it can be 3687), ITGB1 (the GeneID of the gene encoding it can be 3688), CD29 (the GeneID of the gene encoding it can be 3688), ITGB2 (the GeneID of the gene encoding it can be 3689), CD18 (the GeneID of the gene encoding it can be 3689), LFA-1 (the GeneID of the gene encoding it can be 3689), ITGB7 (the GeneID of the gene encoding it can be 3695), NKG2D (the GeneID of the gene encoding it can be 22914), NKG2C (the GeneID of the gene encoding it can be 3822), TNFR2 (the GeneID of the gene encoding it can be 7133), TRANCE/RANKL (the GeneID of the gene encoding it can be 8600), DNAM1 (CD226) (the GeneID of the gene encoding it can be 10666), SLAMF4 (CD244, 2B4) (the GeneID of the gene encoding it can be 51744), CD84 (the GeneID of the gene encoding it can be 8832), CD96 (Tactile) (the GeneID of the gene encoding it can be 10225), CEACAM1 (the GeneID of the gene encoding it can be 634), CRTAM (the GeneID of the gene encoding it can be 56253), Ly9(CD229) (the GeneID of the gene encoding it can be 4063), CD160 (BY55) (the GeneID of the gene encoding it can be 11126), PSGL1 (the GeneID of the gene encoding it can be 6404), CD100 (SEMA4D) (the GeneID of the gene encoding it can be 10507), CD69 (the GeneID of the gene encoding it can be 969), SLAMF6 (NTB-A, Ly108) (the GeneID of the gene encoding it can be 114836), SLAM (SLAMF1, CD150, IPO-3) (the GeneID of the gene encoding it can be 6504), BLAME (SLAMF8) (the GeneID of the gene encoding it can be 56833), SELPLG (CD162) (the GeneID of the gene encoding it can be 6404), LTBR (the GeneID of the gene encoding it can be 4055), LAT (the GeneID of the gene encoding it can be 27040), GADS (the GeneID of the gene encoding it can be 9402), SLP-76 (the GeneID of the gene encoding it can be 3937), PAG/Cbp (the GeneID of the gene encoding it can be 55824), CD19a, and ligands that specifically bind to CD3, ligands that specifically bind to CD28, ligands that specifically bind to HVEM, ligands that specifically bind to CD40L, ligands that specifically bind to OX40, and ligands that specifically bind to 4-1BB body. A co-stimulatory intracellular signaling domain refers to the intracellular portion of a co-stimulatory molecule. The intracellular signaling domain can comprise the entire intracellular portion of a molecule from which it is derived or the entire native intracellular signaling domain or a functional fragment thereof.

In the present application, the term "T cell growth factor" generally refers to a biologically active polypeptide or small molecule compound that causes cell proliferation. In one embodiment, the T cell growth factor can be selected from one or more of the group consisting of: IL-2 (the GeneID of the gene encoding it can be 3558), IL-4 (the GeneID of the gene encoding it can be 3565), IL-7 (the GeneID of the gene encoding it can be 3574), IL-10 (the GeneID of the gene encoding it can be 3586), IL-12 (the GeneID of the gene encoding it can be 3592 or 3593), IL-15 (the GeneID of the gene encoding it can be 3600), and interferon gamma (the GeneID of the gene encoding it can be 3458).

In the present application, the term "substantially simultaneously" generally means that TILs can be in contact with two or more substances simultaneously within a period of time during the contact process, but may not be limited to the fact that the TILs are always in contact with the two or more substances simultaneously during the entire contacting process. For example, substantially simultaneously can mean that the TILs can be in contact with at least 10%, 20%, 30%, 40%, 50%, 60%, 70%, 75%, 80%, 85%, 90%, and 95% of each of the two or more substances simultaneously within a period of time.

In the present application, the term "tumor" generally refers to any new pathological tissue proliferation. The tumor of the present application can be benign or malignant. The tumor of the present application can be solid or hematologic. The term "tumor" can be selected from one or more of the group consisting of: melanoma, ovarian cancer, cervical cancer, lung cancer, bladder cancer, breast cancer, head and neck cancer, pancreatic cancer, liver cancer, stomach cancer, colorectal cancer, and kidney cancer.

In the present application, the term "tumor tissue" generally refers to a sample from any tissue of a tumor in a subject, including any solid tumor and/or non-solid tumor in the subject.

In the present application, the terms "about" and "approximately" generally refer to within a statistically significant numerical range. Such a range can be within an order of magnitude of a given value or range, can be within 50%, can be within 20%, can be within 10%, can be within 5%. The permissible variation encompassed by the term "about" or "approximately" depends on the particular system under study, and can be readily understood by one of ordinary skill in the art. The terms "above", "below", "at most" and "at least" can include the number itself.

DETAILED DESCRIPTION OF THE INVENTION

In one aspect, the present application provides a method for culturing tumor infiltrating lymphocytes (TILs). Wherein, the expanded TILs can be co-cultured with feeder cells after contacting with T cell co-stimulatory molecules and/or T cell growth factors. In one aspect, the present application provides a method for culturing tumor infiltrating lymphocytes (TILs), which includes that: the expanded TILs can be co-cultured with feeder cells after contacting with T cell co-stimulatory molecules and/or T cell growth factors for a period of time. In one embodiment, the expanded TILs can be TILs that have been expanded in vitro.

In one embodiment, the expanded TILs are TILs obtained after at least one stage of the in vitro expansion of the TILs, which are derived from tumor tissues and not expanded in vitro. For example, they can be subjected to at least 2 stages of the in vitro expansion, can be subjected to at least 3 stages of the in vitro expansion, can be subjected to at least 4 stages of the in vitro expansion, can be subjected to at least 5 stages of the in vitro expansion, can be subjected to at least 6 stages of the in vitro expansion, can be subjected to at least 7 stages of the in vitro expansion, can be subjected to at least 8 stages of the in vitro expansion, can be subjected to at least 9 stages of the in vitro expansion, or can be subjected to at least 10 stages of the in vitro expansion.

For example, each stage of the in vitro expansion can be divided by the change in the number of the TIL cells. For example, when the number of the TIL cells is increased by at least about 1-fold, it can be considered that the TIL cells enter the next stage of in vitro expansion. In some embodiments, when the number of the TIL cells is increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 30-fold, at least about 40-fold, at least about 50-fold, at least about 100-fold, at least about 200-fold, at least about 500-fold, or at least about 1000-fold, it can be considered that the TIL cells enter the next stage of the in vitro expansion. For example, each stage of the in vitro expansion can also be divided by the culture conditions of the TIL cells. For example, when the T cell activator and/or the T cell growth factor are added or supplemented into the cell culture medium, it can be considered that the TIL cells enter the next stage of the in vitro expansion. For example, the T cell activator and the T cell co-stimulatory molecule can be used interchangeably in the present application. For example, when TL-2 is added or supplemented into the cell culture medium, it can be considered that the TIL cells enter the next stage of the in vitro expansion. For example, when the feeder cells are added or supplemented into the cell culture medium, it can be considered that the TIL cells enter the next stage of the in vitro expansion. For example, after the TIL cells are subjected to operations of centrifugation and/or cell washing, it can be considered that the TIL cells enter the next stage of the in vitro expansion. For example, each stage can also be divided by the culture days of the TIL cells. For example, when the TIL cells are cultured in vitro for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 30 days, about 40 days, about 50 days or about 100 days, it can be considered that the TIL cells enter the next stage of the in vitro expansion.

For example, the second stage of in vitro expansion can be carried out for at least about 7 days. For example, the second stage of in vitro expansion can be carried out for at least about 9 days. For example, the second stage of in vitro expansion can be carried out for at most about 14 days. For example, the second stage of in vitro expansion can be carried out for at most about 13 days. For example, the second stage of in vitro expansion can be carried out for about 7 days to about 14 days, about 9 days to about 14 days, about 7 days to about 13 days, or about 9 days to about 13 days. For example, the second stage of in vitro expansion of the present application can be carried out for at least about 9 days, at least about 10 days, at least about 11 days, at least about 12 days, at least about 13 days, or at least about 14 days. For example, the second stage of in vitro expansion of the present application can be carried out for about 9 days to about 14 days. For example, the second stage of in vitro expansion of the present application can be carried out for about 9 days to about 14 days, about 10 days to about 14 days, about 11 days to about 14 days, about 12 days to about 14 days, about 13 days to about 14 days, about 9 days to about 13 days, about 10 days to about 13 days, about 11 days to about 13 days, about 12 days to about 13 days, about 9 days to about 12 days, about 10 days to about 12 days, about 11 days to about 12 days, or about 10 days to about 11 days. For example, the second stage of in vitro expansion of the present application can be considered as a REP (rapid expansion protocol) stage.

For example, the first stage of in vitro expansion can be carried out for at least about 7 days. For example, the first stage of in vitro expansion can be carried out for about 7 days to about 14 days. For example, the first stage of in vitro expansion of the present application can be carried out for at least about 7 days, at least about 8 days, at least about 9 days, at least about 10 days, at least about 11 days, at least about 12 days, at least about 13 days, or at least about 14 days. For example, the first stage of in vitro expansion of the present application can be carried out for about 7 days to about 14 days, about 8 days to about 14 days, about 9 days to about 14 days, about 10 days to about 14 days, about 11 days to about 14 days, about 12 days to about 14 days, about 13 days to about 14 days, about 9 days to about 13 days, about 10 days to about 13 days, about 11 days to about 13 days, about 12 days to about 13 days, about 9 days to about 12 days, about 10 days to about 12 days, about 11 days to about 12 days, or about 10 days to about 11 days. For example, the first stage of in vitro expansion of the present application can be considered as a preREP stage.

For example, the days for which the second stage of in vitro expansion of the present application is carried out can be calculated from the start time of the second stage of in vitro expansion. For example, the time when the second stage of in vitro expansion starts can be considered as the second stage of in vitro expansion has been carried out for about 0 days. For example, carrying out for about 24 hours after starting the second stage of in vitro expansion can be considered as the second stage of in vitro expansion has been carried out for about 1 day. For example, the day when the second stage of in vitro expansion starts can be considered as the second stage of in vitro expansion has been carried out for about 0 days. For example, the days for which the second stage of in vitro expansion of the present application is carried out can be calculated with the days for which the second stage of in vitro expansion is carried out. For example, the second day after starting the second stage of in vitro expansion can be considered as the second stage of in vitro expansion has been carried out for about 1 day.

For example, the culture method of the present application can be divided in a two-step division manner. For example, (A) a first TIL population which is derived from tumor tissues and not expanded in vitro can be contacted with a T cell growth factor, wherein a second TIL population is obtained via the step (A); and (B) The second TIL population can be co-cultured with feeder cells after contacting with a T cell activator and/or the T cell growth factor for a period of time, wherein a third TIL population is obtained via the step (B). For example, the step (A) can be carried out for about 7 days to about 14 days. For example, the step (B) can be carried out for about 7 days to about 14 days.

For example, the culture method of the present application can be divided in a three-step division manner. For example, (A) a first TIL population which is derived from tumor tissues and not expanded in vitro can be contacted with a T cell growth factor, wherein a second TIL population is obtained via the step (A); (B) the second TIL population can be contacted with a T cell activator and/or the T cell growth factor, wherein a third TIL population is obtained via the step (B); and (C) the third TIL population can be co-cultured with feeder cells, wherein a fourth TIL population is obtained via the step (C). For example, the step (A) can be carried out for about 7 days to about 14 days. For example, the step (B) can be carried out for about 0 days to about 8 days. For example, the step (C) can be carried out for about 5 days to about 14 days.

For example, the culture method of the present application can be divided in a four-step division manner. For example, (A) a first TIL population which is derived from tumor tissues and not expanded in vitro can be contacted with a T cell growth factor, wherein a second TIL population is obtained via the step (A); (B) the second TIL population can be contacted with a T cell activator and/or the T cell growth factor, wherein a third TIL population is obtained via the step (B); (C) the expression of an optional gene of the third TIL population can be increased or decreased and/or the activity thereof can be increased or decreased, wherein a fourth TIL population is obtained via the step (C); and (D) the fourth TIL population can be co-cultured with feeder cells, wherein a fifth TIL population is obtained via the step (D). For example, the step (A) can be carried out for about 7 days to about 14 days. For example, the step (B) can be carried out for about 0 days to about 4 days. For example, the step (C) can be carried out for about 0 days to about 4 days. For example, the step (D) can be carried out for about 5 days to about 14 days.

For example, the improved TIL properties of the present application comprise one or more of the properties selected from the group consisting of: increased number of TIL cells, increased proportion of viable cells, increased subsist abilities, improved proportion of T cell subpopulations, enhanced cytokine secretion abilities, enhanced tumor cell killing abilities, enhanced T cell receptor (TCR) clonal diversities and increased TIL cell number in tissues and/or tumors.

In one embodiment, the expanded TILs can be co-cultured with the feeder cells after contacting with the T cell co-stimulatory molecule. In one embodiment, the expanded TILs can be co-cultured with the feeder cells after contacting with the T cell growth factor. In one embodiment, the expanded TILs can be co-cultured with the feeder cells after contacting with the T cell co-stimulatory molecule and the T cell growth factor. In one embodiment, the expanded TILs can be co-cultured with at least a portion of the feeder cells after contacting with the T cell co-stimulatory molecule and/or the T cell growth factor. For example, a portion of the feeder cells can be co-cultured with the expanded TILs while the expanded TILs are in contact with the T cell co-stimulatory molecule and/or the T cell growth factor, and at least another portion of the feeder cells are co-cultured with the expanded TILs after the expanded TILs are in contact with the T cell co-stimulatory molecule and/or the T cell growth factor. For example, the at least another portion of the feeder cells can comprise about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, or about 0.1% of the total feeder cells used.

In one embodiment, the expanded TILs can be expanded in vitro. In one embodiment, the expanded TIL cells can be expanded in vivo autologously. In one embodiment, the expanded TIL cells can be expanded in vivo allogeneically. In one embodiment, the expanded TILs can be expanded ex vivo.

In one embodiment, compared to the TILs, which are derived from the tumor tissues and not expanded in vitro, the number of the expanded TILs can be increased by at least 1-fold. For example, compared to the TILs, which are derived from the tumor tissues and not expanded in vitro, the number of the expanded TIL can be increased by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 30-fold, at least about 40-fold, or at least about 50-fold.

In one embodiment, compared to the TILs, which are derived from the tumor tissues and not expanded in vitro, the number of the expanded TIL cells can be increased by more than 50-fold. For example, compared to the TILs which are derived from the tumor tissue, the number of the expanded TIL cells can be increased by more than about 50-fold, more than about 60-fold, more than about 70-fold, more than about 80-fold, more than about 90-fold, more than about 100-fold, more than about 200-fold, more than about 300-fold, more than about 400-fold, more than about 500-fold, more than about 600-fold, more than about 700-fold, more than about 800-fold, more than about 900-fold, more than about 2000-fold, more than about 3000-fold, more than about 4000-fold, more than about 5000-fold, more than about 6000-fold, more than about 7000-fold, more than about 8000-fold, more than about 9000-fold, more than about 10000-fold, more than about 15000-fold, or more than about 20000-fold.

In one aspect, the present application provides a method for culturing tumor infiltrating lymphocytes (TILs). Wherein, the TILs subjected to the first stage of the expansion are subjected to a second stage of the expansion, wherein in the second stage of the expansion, the TILs can be co-cultured with feeder cells after contacting with a T cell co-stimulatory molecule and/or a T cell growth factor.

In one embodiment, in the second stage of the expansion, the TILs can be co-cultured with the feeder cells after contacting with the T cell co-stimulatory molecule. In one embodiment, in the second stage of the expansion, the TILs can be co-cultured with the feeder cells after contacting with the T cell growth factor. In one embodiment, in the second stage of the expansion, the TILs can be co-cultured with the feeder cells after contacting with the T cell co-stimulatory molecule and the T cell growth factor. In one embodiment, in the second stage of the expansion, the TILs can be co-cultured with at least a portion of the feeder cells after contacting with the T cell co-stimulatory molecule and/or the T cell growth factor. For example, in the second stage of the expansion, a portion of the feeder cells can be co-cultured with the TILs while the TILs are in contact with the T cell co-stimulatory molecule and/or the T cell growth factor, and at least another portion of the feeder cells are co-cultured with the TILs after the TILs are in contact with the T cell co-stimulatory molecule and/or the T cell growth factor. For example, the at least another portion of the feeder cells can comprise about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, or about 0.1% of the total feeder cells used.

For example, in the present application, the feeder cells of the present application are added into the cell culture medium of the TILs of the present application at a proportion of the feeder cells of the present application to the TILs of the present application from about 40:1 to about 400:1. For example, in the present application, the feeder cells of the present application are added into the cell culture medium of the TILs of the present application at a proportion of the feeder cells of the present application to the TILs of the present application from about 40:1 to about 400:1, about 40:1 to about 300:1, about 40:1 to about 200:1, about 40:1 to about 100:1, about 40:1 to about 90:1, about 40:1 to about 80:1, about 40:1 to about 70:1, about 40:1 to about 60:1, about 40:1 to about 50:1, about 50:1 to about 400:1, about 60:1 to about 400:1, about 70:1 to about 400:1, about 80:1 to about 400:1, about 90:1 to about 400:1, about 100:1 to about 400:1, about 200:1 to about 400:1, or about 300:1 to about 400:1.

In one embodiment, compared to the TILs subjected to the first stage of the expansion, the number of the TIL cells subjected to the second stage of the expansion can be increased by more than about 50-fold. For example, compared to the TILs subjected to the first stage of the expansion, the number of the TIL cells subjected to the second stage of the expansion can be increased by more than about 50-fold, more than about 60-fold, more than about 70-fold, more than about 80-fold, more than about 90-fold, more than about 100-fold, more than about 200-fold, more than about 300-fold, more than about 400-fold, more than about 500-fold, more than about 600-fold, more than about 700-fold, more than about 800-fold, more than about 900-fold, more than about 1000-fold, more than about 2000-fold, more than about 3000-fold, more than about 4000-fold, more than about 5000-fold, more than about 6000-fold, more than about 7000-fold, more than about 8000-fold, more than about 9000-fold, more than about 10000-fold, more than about 15000-fold, or more than about 20000-fold. In one embodiment, the increase in the number of the TIL cells can be expressed as an expansion fold, and the expansion fold can be the fold to which the number of the TIL cells is expanded after the end of the second stage of the expansion compared to before the start of the second stage of the expansion. For example, if the number of the TIL cells is $1 \times 10^8$ before the start of the second stage of the expansion, and the number of the TIL cells after the end of the second stage of the expansion is $1 \times 10^9$, then it can be considered that the expansion fold of the TIL cells is 10.

In one aspect, the present application provides a method for culturing tumor infiltrating lymphocytes (TILs), which includes that the TILs which are derived from tumor tissues and not expanded in vitro can be subjected to at least one stage of in vitro expansion, wherein in a single stage of the in vitro expansion, the TILs expanded and/or not expanded in vitro can be co-cultured with feeder cells after contacting with a T cell co-stimulatory molecule and/or a T cell growth factor for a period of time.

In another embodiment, the TILs, which are derived from the tumor tissues and not expanded in vitro, can be subjected to at least two stages of the in vitro expansion, wherein in the second stage of in vitro expansion and/or the single stage of the in vitro expansion afterwards, the TILs expanded and/or not expanded in vitro can be co-cultured with the feeder cells after contacting with the T cell co-stimulatory molecule and/or the T cell growth factor for the period of time.

For example, the TILs, which are derived from the tumor tissues and not expanded in vitro, can be subjected to one stage of the in vitro expansion, wherein in the first stage of in vitro expansion, the TILs not expanded in vitro can be co-cultured with the feeder cells after contacting with the T cell co-stimulatory molecule and/or the T cell growth factor for the period of time.

For example, the TILs, which are derived from the tumor tissues and not expanded in vitro, can be subjected to two stages of the in vitro expansion, wherein in the first stage of in vitro expansion, the TILs not expanded in vitro can be co-cultured with the feeder cells after contacting with the T cell co-stimulatory molecule and/or the T cell growth factor for the period of time. The TILs, which are derived from the tumor tissues and not expanded in vitro, can also be subjected to two stages of the in vitro expansion, wherein in the second stage of in vitro expansion, the TILs expanded in vitro can be co-cultured with the feeder cells after contacting with the T cell co-stimulatory molecule and/or the T cell growth factor for the period of time.

For example, the TTLs, which are derived from the tumor tissues and not expanded in vitro, can also be subjected to two stages of the in vitro expansion, wherein in the first stage of in vitro expansion, the TILs not expanded in vitro can be co-cultured with the feeder cells after contacting with the T cell co-stimulatory molecule and/or the T cell growth factor for the period of time, and wherein in the second stage of in vitro expansion, the TILs expanded in vitro can be co-cultured with the feeder cells after contacting with the T cell co-stimulatory molecule and/or the T cell growth factor for the period of time.

For example, the TTLs, which are derived from the tumor tissues and not expanded in vitro, can be subjected to three stages of the in vitro expansion, wherein in the first stage of in vitro expansion, the TILs not expanded in vitro can be co-cultured with the feeder cells after contacting with the T cell co-stimulatory molecule and/or the T cell growth factor for the period of time. The TILs, which are derived from the tumor tissues and not expanded in vitro, can also be subjected to three stages of the in vitro expansion, wherein in the second stage of in vitro expansion, the TILs expanded in vitro can be co-cultured with the feeder cells after contacting with the T cell co-stimulatory molecule and/or the T cell growth factor for the period of time. The TILs, which are derived from the tumor tissues and not expanded in vitro, can also be subjected to three stages of the in vitro expansion, wherein in the third stage of the in vitro expansion, the TILs expanded in vitro can be co-cultured with the feeder cells after contacting with the T cell co-stimulatory molecule and/or the T cell growth factor for the period of time.

For example, the TTLs, which are derived from the tumor tissues and not expanded in vitro, can also be subjected to three stages of the in vitro expansion, wherein in the first stage of in vitro expansion, the TILs not expanded in vitro can be co-cultured with the feeder cells after contacting with the T cell co-stimulatory molecule and/or the T cell growth factor for the period of time, and wherein in the second stage of in vitro expansion, the TILs expanded in vitro can be co-cultured with the feeder cells after contacting with the T cell co-stimulatory molecule and/or the T cell growth factor for the period of time. For example, the TILs, which are derived from the tumor tissues and not expanded in vitro, can also be subjected to three stages of the in vitro expansion, wherein in the first stage of in vitro expansion, the TILs not expanded in vitro can be co-cultured with the feeder cells after contacting with the T cell co-stimulatory molecule and/or the T cell growth factor for the period of time, and wherein in the third stage of the in vitro expansion, the TILs expanded in vitro can be co-cultured with the feeder cells after contacting with the T cell co-stimulatory molecule and/or the T cell growth factor for the period of time. For example, the TILs, which are derived from the tumor tissues and not expanded in vitro, can also be subjected to three stages of the in vitro expansion, wherein in the second stage of in vitro expansion, the TILs not expanded in vitro can be co-cultured with the feeder cells after contacting with the T cell co-stimulatory molecule and/or the T cell growth factor for the period of time, and wherein in the third stage of the in vitro expansion, the TILs expanded in vitro can be co-cultured with the feeder cells after contacting with the T cell co-stimulatory molecule and/or the T cell growth factor for the period of time. For example, the TILs, which are derived from the tumor tissues and not expanded in vitro, can also be subjected to three stages of the in vitro expansion, wherein in the first stage of in vitro expansion, the TILs not expanded in vitro can be co-cultured with the feeder cells after contacting with the T cell co-stimulatory molecule and/or the T cell growth factor for the period of time, and wherein in the second stage of in vitro expansion, the TILs expanded in vitro can be co-cultured with the feeder cells after contacting with the T cell co-stimulatory molecule and/or the T cell growth factor for the period of time, and wherein in the third stage of the in vitro expansion, the TILs expanded in vitro can be co-cultured with the feeder cells after contacting with the T cell co-stimulatory molecule and/or the T cell growth factor for the period of time.

In one aspect, the present application provides a method for culturing tumor infiltrating lymphocytes (TILs). Wherein, the TILs can be co-cultured with feeder cells after contacting with a T cell co-stimulatory molecule and/or a T cell growth factor. The TILs can be subjected to more than two stages of expansion during the entire culture process. The contact of the TILs with the T cell co-stimulatory molecule and/or the T cell growth factor and the co-culture of the TILs and the feeder cells can occur in the same stage of the expansion.

In one embodiment, the TILs can be subjected to more than two stages of the expansion during the entire culture process. The TILs can be co-cultured with the feeder cells after contacting with the T cell co-stimulatory molecule. In one embodiment, the TILs can be subjected to more than two stages of the expansion during the entire culture process. The TILs can be co-cultured with the feeder cells after contacting with the T cell growth factor. In one embodiment, the TILs can be subjected to more than two stages of the expansion during the entire culture process. The TILs can be co-cultured with the feeder cells after contacting with the T cell co-stimulatory molecule and the T cell growth factor. In one embodiment, the TILs can be subjected to more than two stages of the expansion during the entire culture process. The TILs can be co-cultured with at least a portion of the feeder cells after contacting with the T cell co-stimulatory molecule and/or the T cell growth factor. For example, the TILs can be subjected to more than two stages of the expansion during the entire culture process. A portion of the feeder cells can be co-cultured with the TILs while the TILs are in contact with the T cell co-stimulatory molecule and/or the T cell growth factor, and at least another portion of the feeder cells are co-cultured with the TILs after the TILs are in contact with the T cell co-stimulatory molecule and/or the T cell growth factor. For example, the at least another portion of the feeder cells can comprise about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, or about 0.1% of the total feeder cells used.

In one embodiment, the TILs can be subjected to more than two stages of the expansion during the entire culture process. For example, the TILs can be subjected to more than 2, 3, 4, 5, 6, 7, 8, 9, 10, 20, 50, 100 stages of the expansion during the entire culture process.

In one embodiment, the contact of the TILs with the T cell co-stimulatory molecule and/or the T cell growth factor and the co-culture of the TILs and the feeder cells can occur in the first stage of the expansion and/or the second stage of the expansion. In one embodiment, the contact of the TILs with the T cell co-stimulatory molecule and/or the T cell growth factor and the co-culture of the TILs and the feeder cells can occur in the first stage of the expansion, the second stage of the expansion and/or the third stage of the expansion. For example, the contact of the TILs with the T cell co-stimulatory molecule and/or the T cell growth factor and the co-culture of the TILs and the feeder cells can occur in the first stage of the expansion. For example, the contact of the TILs with the T cell co-stimulatory molecule and/or the T cell growth factor and the co-culture of the TILs and the feeder cells can occur in the second stage of the expansion. For example, the contact of the TILs with the T cell co-stimulatory molecule and/or the T cell growth factor and the co-culture of the TILs and the feeder cells can occur in the third stage of the expansion. For example, the contact of the TILs with the T cell co-stimulatory molecule and/or the T cell growth factor and the co-culture of the TILs and the feeder cells can occur in the first stage of the expansion and the second stage of the expansion. For example, the contact of the TILs with the T cell co-stimulatory molecule and/or the T cell growth factor and the co-culture of the TILs and the feeder cells can occur in the first stage of the expansion and the third stage of the expansion. For example, the contact of the TILs with the T cell co-stimulatory molecule and/or the T cell growth factor and the co-culture of the TILs and the feeder cells can occur in the second stage of the expansion and the third stage of the expansion. For example, the contact of the TILs with the T cell co-stimulatory molecule and/or the T cell growth factor and the co-culture of the TILs and the feeder cells can occur in the first stage of the expansion, the second stage of the expansion and the third stage of the expansion.

In one embodiment, compared to co-culturing the TILs with the feeder cells and at the same time that contacting the TILs with the T cell co-stimulatory molecule and the T cell growth factor, co-culturing the TILs with the feeder cells after contacting the TILs with the T cell co-stimulatory molecule and/or the T cell growth factor for the period of time interval can enhance the expansion effect of the TILs. For example, the enhancing of the expansion effect of TILs can include that selected from the group consisting of: increasing the number of TIL cells, changing the proportion of TIL cells, enhancing the secretion abilities of TIL cells, and enhancing the killing abilities of TIL cells. In one embodiment, co-culturing the TILs with the feeder cells after contacting the TILs with the T cell co-stimulatory molecule and/or the T cell growth factor for the period of time interval can increase the number of the TIL cells. In one embodiment, co-culturing the TILs with the feeder cells after contacting the TILs with the T cell co-stimulatory molecule and/or the T cell growth factor for the period of time interval can enhance the secretion abilities of the TIL cells. In one embodiment, co-culturing the TILs with the feeder cells after contacting the TILs with the T cell co-stimulatory molecule and/or the T cell growth factor for the period of time interval can enhance the expansion effect of the TILs.

In one embodiment, co-culturing the TILs with the feeder cells after contacting the TILs with the T cell co-stimulatory molecule and/or the T cell growth factor for the period of time interval can change the proportion of the TIL cells. For example, the changing of the proportion of the TIL cells can include that selected from the group consisting of: possibly increasing the proportion of central memory T cells (Tcm) in TILs, possibly increasing the proportion of the TIL cells other than regulatory T cells (Treg), possibly reducing the proportion of regulatory T cells (Treg), possibly increasing the proportion of activated T cells, possibly increasing the proportion of tumor-specific T cells, and possibly increasing the proportion of stem-like T cells. For example, the changing of the proportion of the TIL cells can include that selected from the group consisting of: possibly increasing the proportion of $CD45RA^-CCR7^+$ central memory T cells (Tcm) in TILs, possibly increasing the proportion of the TIL cells other than $CD4^+CD25^+Foxp3^+$ regulatory T cells (Treg), possibly increasing the proportion of $CD4^+CD25^+Foxp3^+$ regulatory T cells (Treg), possibly increasing the proportion of activated T cells, possibly increasing the proportion of $CD103^+CD39^+$ tumor-specific T cells, and possibly increasing the proportion of $TCF1^+$ stem-like T cells. Alternatively, for example, the changing of the proportion of the TIL cells in the present application can include increasing the proportion of $CD45RO^+CD62L^+$ central memory T cells (Tcm) in TILs. For example, the changing of the proportion of the TIL cells can include that selected from the group consisting of: increasing the proportion of $PD1^+$ cells, increasing the proportion of $LAG3^+$ cells, and increasing the proportion of $CD28^+$ cells. The changing of the proportion of the TIL cells can include the proportion of central memory T cells, the proportion of activated T cells, the proportion of tumor-specific T cells, and/or the stem cell-like T cells in the TIL cells cultured according to the method of the present application. Compared to co-culturing the TILs with the feeder cells while contacting the TILs with the T cell co-stimulatory molecule and the T cell growth factor, an increase of at least about 1%, at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 97%, at least about 98%, or at least about 99% is obtained. The changing of the proportion of the TIL cells can include regulatory T cells (Treg) in the TIL cells cultured according to the method of the present application, compared to co-culturing the TILs with the feeder cells while contacting the TILs with the T cell co-stimulatory molecule and the T cell growth factor, a reduction of at least about 1%, at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 97%, at least about 98%, or at least about 99% is obtained.

In one embodiment, the TILs can be co-cultured with the feeder cells after contacting with the T cell co-stimulatory molecule and/or the T cell growth factor. In one embodiment, the after can refer to after more than 2 hours. For example, the TILs can be co-cultured with the feeder cells after contacting with the T cell co-stimulatory molecule and/or the T cell growth factor for 6 to 72 hours or 12 to 48 hours. For example, the TILs can be co-cultured with the feeder cells after contacting with the T cell co-stimulatory molecule and/or the T cell growth factor for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 36 hours, about 48 hours, about 60 hours or about 72 hours. For example, the TILs can be co-cultured with the feeder cells after contacting with the T cell co-stimulatory molecule and/or the T cell growth factor for about 1 day, about 2 days, about 3 days, about 4 days, about 5 days, about 6 days, about 7 days, about 8 days, about 9 days, about 10 days, about 11 days, about 12 days, about 13 days, or about 14 days.

In one embodiment, the TILs can be co-cultured with the feeder cells after contacting with the T cell co-stimulatory molecule and/or the T cell growth factor. In one embodiment, the T cell co-stimulatory molecule can be selected from one or more of the group consisting of: CD80, CD86, B7-H3, 4-1BBL, CD27, CD30, CD134, B7h, CD40, LIGHT, an antibody that specifically binds to CD3, an antibody that specifically binds to CD28, an antibody that specifically binds to HVEM, an antibody that specifically binds to CD40L, an antibody that specifically binds to OX40, and an antibody that specifically binds to 4-1BB.

In one embodiment, the contact of the TILs with the T cell co-stimulatory molecule can include contacting one or more of the T cell co-stimulatory molecules with the TILs alone, and/or contacting a plurality of the T cell co-stimulatory molecules with the TILs simultaneously. In one embodiment, the contact can include contacting one or more of the T cell co-stimulatory molecules with the TILs alone. In one embodiment, the contact can include contacting a plurality of the T cell co-stimulatory molecules with the TILs simultaneously. For example, the one or more of the T cell co-stimulatory molecules can be added into the cell culture medium of the TILs alone. For example, the plurality of the T cell co-stimulatory molecules can be added simultaneously into the cell culture medium of the TILs. For example, the one of the T cell co-stimulatory molecules can be added into the cell culture medium of the TILs in one or more of the forms selected from the group consisting of: engineered cells expressing the T cell co-stimulatory molecule, nanoparticles chimeric with the T cell co-stimulatory molecule, and polymers chimeric with the T cell co-stimulatory molecule. For example, the plurality of the T cell co-stimulatory molecules can be added into the cell culture medium of the TILs in forms selected from the group consisting of: mixtures, fusion proteins, engineered cells expressing the plurality of the T cell co-stimulatory molecules, nanoparticles chimeric with the plurality of the T cell co-stimulatory molecules, and polymers chimeric with the plurality of the T cell co-stimulatory molecules. For example, the T cell co-stimulatory molecule can be an antibody that specifically binds to CD3, such as can be OKT3 from Miltenyi Biotech.

In one embodiment, the TILs can be co-cultured with the feeder cells after contacting with the T cell co-stimulatory molecule and/or the T cell growth factor. In one embodiment, the T cell growth factor can be selected from one or more of the group consisting of: IL-2, IL-4, IL-7, IL-10, IL-12, IL-15, and interferon gamma. For example, the T cell growth factor can be IL-2. In one embodiment, the initial concentration of IL-2 in the cell culture medium of the TILs can be more than about 1000 IU/mL. In one embodiment, the initial concentration of IL-2 in the cell culture medium of the TILs can be more than about 1500 IU/mL, about 2000 IU/mL, about 2500 IU/mL, about 2600 IU/mL, about 2700 IU/mL, about 2800 IU/mL, about 2900 IU/mL, about 3000 IU/mL, about 3100 IU/mL, about 3200 IU/mL, about 3300 IU/mL, about 3400 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, about 8000 IU/mL, about 8500 IU/mL, or about 9000 IU/mL.

In one embodiment, the contact of the TILs with the T cell growth factor can include contacting one or more of the T cell growth factors with the TILs alone, and/or contacting a plurality of the T cell growth factors with the TILs simultaneously. In one embodiment, the contact can include contacting one or more of the T cell growth factors with the TILs alone. In one embodiment, the contact can include contacting a plurality of the T cell growth factors with the TILs simultaneously. For example, the one or more of the T cell growth factors can be added into the cell culture medium of the TILs alone. For example, the plurality of the T cell growth factors can be added simultaneously into the cell culture medium of the TILs. For example, the one of the T cell growth factors can be added into the cell culture medium of the TILs in one or more of the forms selected from the group consisting of: engineered cells expressing the T cell growth factor, nanoparticles chimeric with the T cell growth factor, and polymers chimeric with the T cell growth factor. For example, the plurality of the T cell growth factors can be added into the cell culture medium of the TILs in forms selected from the group consisting of: mixtures, fusion proteins, engineered cells expressing the plurality of the T cell growth factors, nanoparticles chimeric with the plurality of the T cell growth factors, and polymers chimeric with the plurality of the T cell growth factors.

In one embodiment, the TILs can be TILs which are derived from fragments of the tumor tissue. In one embodiment, the TILs can be obtained by processing the tumor tissue into tumor fragments. In one embodiment, the tumor fragments have a volume of about 1-27 mm$^3$. In one embodiment, the tumor fragments have a volume of about 1 mm$^3$, about 2 mm$^3$, about 3 mm$^3$, about 4 mm$^3$, about 5 mm$^3$, about 6 mm$^3$, about 7 mm$^3$, about 8 mm$^3$, about 9 mm$^3$, about 10 mm$^3$, about 11 mm$^3$, about 12 mm$^3$, about 13 mm$^3$, about 15 mm$^3$, about 17 mm$^3$, about 19 mm$^3$, about 20 mm$^3$, about 21 mm$^3$, about 23 mm$^3$, about 24 mm$^3$, about 25 mm$^3$, about 26 mm$^3$ or 27 mm$^3$.

In one embodiment, the feeder cells can include antigen presenting cells. In one embodiment, the feeder cells can include one or more selected from the group consisting of: peripheral mononuclear cells, dendritic cells, and artificial antigen presenting cells. For example, the feeder cells can be peripheral mononuclear cells. For example, the feeder cells can be dendritic cells. For example, the feeder cells can be artificial antigen presenting cells. For example, the feeder cells can be isolated artificial antigen presenting cells (aAPCs), which can comprise cells expressing HLA-A/B/C, CD64, CD80, ICOS-L, and CD58, and can be modified to express more than one co-stimulatory molecules. In one embodiment, the feeder cells can be irradiated. For example, the feeder cells can be irradiated with gamma rays, or can be irradiated with X-rays.

In one embodiment, the TILs can be co-cultured with the feeder cells. In one embodiment, the co-culture can be contacting the surfaces of the TILs and the feeder cells, for example, the feeder cells can be added into the cell culture medium of the TILs. In one embodiment, the co-culture can be contacting the surfaces of the TILs and the feeder cells. In one embodiment, the feeder cells can be immobilized on a device and added into the cell culture medium of the TILs. In one embodiment, the feeder cells can be separated from the cells of the TILs by membranes, meshes and grids, but they can exchange substances or can be in contact to some extent. In one embodiment, the cellular metabolites of the feeder cells can be added into the cell culture medium of the TILs. For example, in the present application, the feeder cells of the present application are added into the cell culture medium of the TILs of the present application at a proportion of the feeder cells of the present application to the TILs of the present application from about 40:1 to about 400:1. For example, in the present application, the feeder cells of the present application are added into the cell culture medium of the TILs of the present application, at a proportion of the feeder cells of the present application to the TILs of the present application from about 40:1 to about 400:1, about 40:1 to about 300:1, about 40:1 to about 200:1, about 40:1 to about 100:1, about 40:1 to about 90:1, about 40:1 to about 80:1, about 40:1 to about 70:1, about 40:1 to about 60:1, about 40:1 to about 50:1, about 50:1 to about 400:1, about 60:1 to about 400:1, about 70:1 to about 400:1, about 80:1 to about 400:1, about 90:1 to about 400:1, about 100:1 to about 400:1, about 200:1 to about 400:1, or about 300:1 to about 400:1.

In one aspect, the present application provides a method for culturing tumor infiltrating lymphocytes (TILs). The method for obtaining TIL cells from a tissue sample of a subject can be to obtain an in situ tumor sample or a metastatic tumor sample the weight of which can be at least about 1 g through a surgery on the patient, or can be to combine a plurality of tissues. The tumor tissue is transported at approximately 2-8 degrees in basic medium and processed within 48 hours. The tissue pieces can be mechanically disrupted to a size of about 1-27 mm$^3$ per piece, transferred into a gas-permeable culture bag or Grex, to which are added T cell serum-free medium and IL-2 with a concentration of 1000-9000 IU/mL (e.g., the concentration can be 6000 IU/mL), and cultured for about 3-14 days. The cells in the medium are collected and can be transferred together with the tissue pieces into a gas-permeable culture bag, or Grex, or Xuri equipment. The T cell serum-free medium can be supplemented with a CD3 antibody at about 30 ng/mL and IL-2 (1000-9000 IU/mL). After activation for a period of time, irradiated PBMCs (TILs and PBMCs are in a proportion of 1:40-1:400) are added, and the expansion and culture last about 3-14 days. After filtering the tissue pieces, the cells in the medium can be collected, washed, cryopreserved, and detected using a cell processing system. The CD3 proportion of the final product can be greater than 80%, the cell viability rate can be greater than 70%, and greater than 80% of the T cells can be memory effector T cells and effector T cells. After stimulation, the final product can secrete IFNγ, and can be characterized by an up-regulated proportion of activated T cells.

In one aspect, the present application provides a tumor infiltrating lymphocyte (TIL), which can be cultured according to the culture method of the present application. In one embodiment, the TILs provided by the present application can comprise one of or a batch of TILs cultured by the culture method of the present application. In one embodiment, the TILs provided by the present application can comprise a plurality of or multiple batches of TILs cultured by the culture method of the present application and combined in any proportion.

In some embodiments, the TILs expanded using the method of the present application can be administered to a patient as a pharmaceutical composition. In some embodiments, the pharmaceutical composition can be a suspension of the TILs in a sterile buffer. The TILs expanded using the PBMCs of the present application can be administered by any suitable route known in the art. In some embodiments, T cells can be administered as a single intra-arterial or intravenous infusion, which can last about 30 to 60 minutes. Other suitable routes of administration can include intraperitoneal, intrathecal and intralymphatic administration.

Any suitable dose of TILs can be administered. In some embodiments, for example when the tumor is a melanoma, from about $2.3\times10^9$ to about $13.7\times10^{10}$ TILs can be administered. In some embodiments, from about $1\times10^9$ to about $12\times10^{10}$ TILs can be administered. In some embodiments, from about $1.2\times10^{10}$ to about $4.3\times10^{10}$ TILs can be administered. In some embodiments, from about $3\times10^{10}$ to about $12\times10^{10}$ TILs can be administered. In some embodiments, from about $4\times10^{10}$ to about $10\times10^{10}$ TILs can be administered. In some embodiments, from about $5\times10^{10}$ to about $8\times10^{10}$ TILs can be administered. In some embodiments, from about $6\times10^{10}$ to about $8\times10^{10}$ TILs can be administered. In some embodiments, from about $7\times10^{10}$ to about $8\times10^{10}$ TILs can be administered. In some embodiments, the therapeutically effective dose can be about $2.3\times10^9$ to about $13.7\times10^{10}$. In some embodiments, the therapeutically effective dose can be about $1\times10^9$ to about $12\times10^{10}$. In some embodiments, the therapeutically effective dose can be about $1.2\times10^{10}$ to about $4.3\times10^{10}$. In some embodiments, the therapeutically effective dose can be about $3\times10^{10}$ to about $12\times10^{10}$. In some embodiments, the therapeutically effective dose can be about $4\times10^{10}$ to about $10\times10^{10}$. In some embodiments, the therapeutically effective dose can be about $5\times10^{10}$ to about $8\times10^{10}$. In some embodiments, the therapeutically effective dose can be about $6\times10^{10}$ to about $8\times10^{10}$. In some embodiments, the therapeutically effective dose can be about $7\times10^{10}$ to about $8\times10^{10}$.

In some embodiments, the number of TILs provided in the compositions of the present application can be about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, about $1\times10^7$, about $2\times10^7$, about $3\times10^7$, about $4\times10^7$, about $5\times10^7$, about $6\times10^7$, about $7\times10^7$, about $8\times10^7$, about $9\times10^7$, about $1\times10^8$, about $2\times10^8$, about $3\times10^8$, about $4\times10^8$, about $5\times10^8$, about $6\times10^8$, about $7\times10^8$, about $8\times10^8$, about $9\times10^8$, about $1\times10^9$, about $2\times10^9$, about $3\times10^9$, about $4\times10^9$, about $5\times10^9$, about $6\times10^9$, about $7\times10^9$, about $8\times10^9$, about $9\times10^9$, about $1\times10^{10}$, about $2\times10^{10}$, about $3\times10^{10}$, about $4\times10^{10}$, about $5\times10^{10}$, about $6\times10^{10}$, about $7\times10^{10}$, about $8\times10^{10}$, about $9\times10^{10}$, about $1\times10^{11}$, about $2\times10^{11}$, about $3\times10^{11}$, about $4\times10^{11}$, about $5\times10^{11}$, about $6\times10^{11}$, about $7\times10^{11}$, about $8\times10^{11}$, about $9\times10^8$, about $1\times10^{12}$, about $2\times10^{12}$, about $3\times10^{12}$, about $4\times10^{12}$, about $5\times10^{12}$, about $6\times10^{12}$, about $7\times10^{12}$, about $8\times10^{12}$, about $9\times10^{12}$, about $1\times10^{13}$, about $2\times10^{13}$, about $3\times10^{13}$, about $4\times10^{13}$, about $5\times10^{13}$, about $6\times10^{13}$, about $7\times10^{13}$, about $8\times10^{13}$, or about $9\times10^{13}$. In some embodiments, the number of the TILs provided in the compositions of the present application can range from about $1\times10^6$ to $5\times10^6$, about $5\times10^6$ to $1\times10^7$, about $1\times10^7$ to $5\times10^7$, about $5\times10^7$ to $1\times10^8$, about $1\times10^8$ to $5\times10^8$, about $5\times10^8$ to $1\times10^9$, about $1\times10^9$ to $5\times10^9$, about $5\times10^9$ to $1\times10^{10}$, about $1\times10^{10}$ to $5\times10^{10}$, about $5\times10^{10}$ to $1\times10^{11}$, about $5\times10^{11}$ to $1\times10^{12}$, about $1\times10^{12}$ to $5\times10^{12}$, or about $5\times10^{12}$ to $1\times10^{13}$.

In some embodiments, the concentration of the TILs provided in the compositions of the present application can be less than, e.g., about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, about 0.0001% w/w, w/v, or v/v of the composition.

In some embodiments, the concentration of the TILs provided in the composition of the present application can be greater than about 90%, about 80%, about 70%, about 60%, about 50%, about 40%, about 30%, about 20%, about 19.75%, about 19.50%, about 19.25%, about 19%, about 18.75%, about 18.50%, about 18.25%, about 18%, about 17.75%, about 17.50%, about 17.25%, about 17%, about 16.75%, about 16.50%, about 16.25%, about 16%, about 15.75%, about 15.50%, about 15.25%, about 15%, about 14.75%, about 14.50%, about 14.25%, about 14%, about 13.75%, about 13.50%, about 13.25%, about 13%, about 12.75%, about 12.50%, about 12.25%, about 12%, about 11.75%, about 11.50%, about 11.25%, about 11%, about 10.75%, about 10.50%, about 10.25%, about 10%, about 9.75%, about 9.50%, about 9.25%, about 9%, about 8.75%, about 8.50%, about 8.25%, about 8%, about 7.75%, about 7.50%, about 7.25%, about 7%, about 6.75%, about 6.50%, about 6.25%, about 6%, about 5.75%, about 5.50%, about 5.25%, about 5%, about 4.75%, about 4.50%, about 4.25%, about 4%, about 3.75%, about 3.50%, about 3.25%, about 3%, about 2.75%, about 2.50%, about 2.25%, about 2%, about 1.75%, about 1.50%, about 125%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about or 0.0002%, or about 0.0001% w/w, w/v, or v/v of the composition.

In some embodiments, the concentration of the TILs provided in the compositions of the present application can range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12%, or about 1% to about 10% w/w, w/v or v/v.

In some embodiments, the concentration of the TILs provided in the compositions of the present application can range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, or about 0.1% to about 0.9% w/w, w/v, or v/v of the composition.

In some embodiments, the amount of TILs provided in the compositions of the present application can be equal to or less than about 10 g, about 9.5 g, about 9.0 g, about 8.5 g, about 8.0 g, about 7.5 g, about 7.0 g, about 6.5 g, about 6.0 g, about 5.5 g, about 5.0 g, about 4.5 g, about 4.0 g, about 3.5 g, about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 g, about 0.02 g, about 0.01 g, about 0.009 g, about 0.008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g.

In some embodiments, the amount of TIL provided in the compositions of the present application can be greater than about 0.0001 g, about 0.0002 g, about 0.0003 g, about 0.0004 g, about 0.0005 g, about 0.0006 g, about 0.0007 g, about 0.0008 g, about 0.0009 g, about 0.001 g, about 0.0015 g, about 0.002 g, about 0.0025 g, about 0.003 g, about 0.0035 g, about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 g, about 0.015 g, about 0.02 g, about 0.025 g, about 0.03 g, about 0.035 g, about 0.04 g, about 0.045 g, about 0.05 g, about 0.055 g, about 0.06 g, about 0.065 g, about 0.07 g, about 0.075 g, about 0.08 g, about 0.085 g, about 0.09 g, about 0.095 g, about 0.1 g, about 0.15 g, about 0.2 g, about 0.25 g, about 0.3 g, about 0.35 g, about 0.4 g, about 0.45 g, about 0.5 g, about 0.55 g, about 0.6 g, about 0.65 g, about 0.7 g, about 0.75 g, about 0.8 g, about 0.85 g, about 0.9 g, about 0.95 g, about 1 g, about 1.5 g, about 2 g, about 2.5 g, about 3 g, about 3.5 g, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g.

In some embodiments, the TILs can be administered in a single dose. Such administration can be by injection, e.g., intravenous injection. In some embodiments, the TILs can be administered in multiple doses. The dosage can be once, twice, three times, four times, five times, six times or more than six times per year. The dosage can be once a month, once every two weeks, once a week or once every 2 days. In some embodiments, the administration of the TILs can be continuous.

In another aspect, the present application provides a method for culturing tumor infiltrating lymphocytes (TILs). The method for obtaining TIL cells from a tissue sample of a subject can be to obtain an in situ tumor sample or a metastatic tumor sample the weight of which can be at least about 1 g through a surgery on the patient, or can be to combine a plurality of tissues. The tumor tissue is transported at about 2-8 degrees in a sample transport solution, e.g. a commercially commonly used tumor tissue transport solution, tumor tissue preservation solution or tumor tissue transport solution, and processed within 48 hours. The tissue pieces can be mechanically disrupted to a size of about 1-27 mm$^3$ per piece, transferred into a gas-permeable culture bag or Grex, to which are added T cell serum-free medium and IL-2 with a concentration of 300-9000 IU/mL (e.g., the concentration can be 1000-9000 IU/mL, for example can be 6000 IU/mL), and cultured for about 3-14 days. The harvested TIL cells can be cryopreserved and then resuscitated, or the cells in the medium can be directly collected and transferred into a gas permeable culture bag, or Grex, or Xuri equipment. The T cell serum-free medium can be supplemented with a CD3 antibody of the present application at a concentration of 300-9000 IU/mL (for example, the concentration can be 1000-9000 IU/mL, for example, it can be 6000 IU/mL) IL-2. After activating the TILs of the present application for a period of time, irradiated PBMC (TILs and PBMCs are in a proportion of about 1:40-about 1:400) are added, and the expansion and culture last about 3-14 days. The cells in the medium can be collected, washed, cryopreserved, and detected using a cell processing system. The CD3 proportion of the final product can be greater than 80%, the cell viability rate can be greater than 50%, and greater than 80% of the T cells can be memory effector T cells and effector T cells. After stimulation, the final product can secrete IFN-γ, and/or can be characterized by an up-regulated proportion of activated T cells.

In one aspect, the present application provides a pharmaceutical preparation. In some embodiments, the pharmaceutical preparation can comprise TILs described in the present application and/or a composition described in the present application, as well as a pharmaceutically acceptable carrier.

In one aspect, the present application provides a kit, which can comprise a T cell co-stimulatory molecule, a T cell growth factor and/or feeder cells of the method for culturing tumor infiltrating lymphocytes (TILs) described in the present application, and instructions describing the steps of the method for culturing tumor infiltrating lymphocytes (TILs) of the present application. In one aspect, the present application provides a kit, which can comprise the TILs described in the present application and/or the pharmaceutical preparation described in the present application.

In one aspect, the present application provides a method for affecting tumor cell growth, which can include administering to a subject TILs described in the present application and/or a pharmaceutical preparation described in the present application. In some embodiments, affecting tumor growth can comprise reducing the volume of the tumor to, for example, about 99%, about 95%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2% or about 0.1% of the volume before the administration.

In one aspect, the present application provides a use of the TILs described in the present application and/or the pharmaceutical preparation described in the present application in preparing a medicament which can prevent and/or treat tumors. In some embodiments, the tumors are selected from solid tumors. In some embodiments, the tumors can be selected from one or more of the group consisting of: melanoma, ovarian cancer, cervical cancer, lung cancer, bladder cancer, breast cancer, head and neck cancer, pancreatic cancer, liver cancer, stomach cancer, colorectal cancer, and kidney cancer.

In one aspect, the present application provides a method for preventing and/or treating tumors, which can include administering to a subject a TIL described in the present application and/or a pharmaceutical preparation described in the present application. In some embodiments, the tumors are selected from solid tumors. In some embodiments, the tumors can be selected from one or more of the group consisting of: melanoma, ovarian cancer, cervical cancer, lung cancer, bladder cancer, breast cancer, head and neck cancer, pancreatic cancer, liver cancer, stomach cancer, colorectal cancer, and kidney cancer.

In one aspect, the present application provides a TIL described in the present application and/or a pharmaceutical preparation described in the present application, which can be used to prevent and/or treat tumors. In some embodiments, the tumors are selected from solid tumors. In some embodiments, the tumors can be selected from one or more of the group consisting of: melanoma, ovarian cancer, cervical cancer, lung cancer, bladder cancer, breast cancer, head and neck cancer, pancreatic cancer, liver cancer, stomach cancer, colorectal cancer, and kidney cancer.

Illustrative Embodiments

Embodiment 1. A method for culturing tumor infiltrating lymphocytes (TILs), comprising co-culturing expanded TILs with feeder cells after contacting the expanded TTLs with a T cell co-stimulatory molecule and/or a T cell growth factor for a period of time.

Embodiment 2. The method according to embodiment 1, wherein the expanded TILs are TILs expanded in vitro.

Embodiment 3. The method according to any one of embodiments 1-2, wherein the expanded TILs are TILs obtained after subjecting the TILs, which are derived from tumor tissues and not expanded in vitro, to at least one stage of in vitro expansion.

Embodiment 4. The method according to embodiment 3, wherein the number of the expanded TILs is increased by at least 1-fold compared to the TILs that are derived from the tumor tissues and not expanded in vitro.

Embodiment 5. The method according to any one of embodiments 1-4, wherein the number of the expanded TILs is increased to at least 50-fold after the co-culture.

Embodiment 6. The method according to any one of embodiments 1-5, wherein the number of the expanded TILs is increased to about 50-20000 folds after the co-culture.

Embodiment 7. A method for culturing tumor infiltrating lymphocytes (TTLs), wherein the method comprises subjecting the TILs, which are derived from tumor tissues and not expanded in vitro, to at least one stage of in vitro expansion, and wherein in a single stage of the in vitro expansion, the TILs expanded and/or not expanded in vitro are co-cultured with feeder cells after contacting with a T cell co-stimulatory molecule and/or a T cell growth factor for a period of time.

Embodiment 8. The method according to embodiment 7, wherein in the first stage of the in vitro expansion, the TILs not expanded in vitro are co-cultured with the feeder cells after contacting with the T cell co-stimulatory molecule and/or the T cell growth factor for the period of time.

Embodiment 9. The method according to embodiment 7, wherein the method comprises subjecting the TILs, which are derived from the tumor tissues and not expanded in vitro, to at least two stages of the in vitro expansion, and wherein in the second stage of the in vitro expansion, the TILs expanded in vitro are co-cultured with the feeder cells after contacting with the T cell co-stimulatory molecule and/or the T cell growth factor for the period of time.

Embodiment 10. The method according to any one of embodiments 7-9, wherein the TILs obtainable by co-culturing the TILs expanded and/or not expanded in vitro with the feeder cells after contacting the TILs with the T cell co-stimulatory molecule and/or the T cell growth factor for the period of time in a single stage of the in vitro expansion shows improved TIL properties, compared to co-culturing the TILs expanded and/or not expanded in vitro with the feeder cells and simultaneously contacting the TILs with the T cell co-stimulatory molecule and/or the T cell growth factor in a single stage of the in vitro.

Embodiment 11. The method according to embodiment 10, wherein the improved TIL properties comprise one or more of the properties selected from the group consisting of: increased number of TIL cells, increased proportion of viable cells, increased subsist abilities, improved proportion of T cell subpopulations, enhanced cytokine secretion abilities, enhanced tumor cell killing abilities, enhanced T cell receptor (TCR) clonal diversities and increased TIL cell number in tissues and/or tumors.

Embodiment 12. The method according to embodiment 11, wherein the changing of the proportion of TIL cells comprises one or more of the properties selected from the group consisting of: increasing the proportion of central memory T cells in TTLs, decreasing the proportion of regulatory T cells, increasing the proportion of activated T cells, increasing the proportion of tumor-specific T cells, and increasing the proportion of stem cell-like T cells.

Embodiment 13. The method according to any one of embodiments 1-12, wherein the expanded TILs are co-cultured with the feeder cells after contacting with the T cell co-stimulatory molecule and/or the T cell growth factor for at least about 2 hours.

Embodiment 14. The method according to any one of embodiments 1-13, wherein the expanded TILs are co-cultured with the feeder cells after contacting with the T cell co-stimulatory molecule and/or the T cell growth factor for about 6 to 72 hours.

Embodiment 15. The method according to any one of embodiments 1-14, wherein the expanded TILs are co-cultured with the feeder cells after contacting with the T cell co-stimulatory molecule and/or the T cell growth factor for about 12 to 48 hours.

Embodiment 16. The method according to any one of embodiments 1-14, wherein the expanded TILs are co-cultured with the feeder cells after contacting with the T cell co-stimulatory molecule and/or the T cell growth factor for about 6, 12, 24, 48 or 72 hours.

Embodiment 17. The method according to any one of embodiments 1-16, wherein the T cell co-stimulatory molecule is one or more of the molecules selected from the group consisting of: CD80, CD86, B7-H3, 4-1BBL, CD27, CD30, CD134, B7h, CD40, LIGHT, an antibody that specifically binds to CD3, an antibody that specifically binds to CD28, an antibody that specifically binds to HVEM, an antibody that specifically binds to CD40L, an antibody that specifically binds to OX40, and an antibody that specifically binds to 4-1BB.

Embodiment 18. The method according to any one of embodiments 1-17, wherein the T cell co-stimulatory molecule is an antibody and/or an antigen-binding fragment thereof that specifically binds to CD3.

Embodiment 19. The method according to any one of embodiments 1-18, wherein the method comprises contacting one of the T cell co-stimulatory molecules, or each of a plurality of the T cell co-stimulatory molecules with the TILs individually.

Embodiment 20. The method according to any one of embodiments 1-18, wherein the method comprises contacting a plurality of the T cell co-stimulatory molecules with the TILs simultaneously.

Embodiment 21. The method according to any one of embodiments 1-19, wherein the method comprises adding one of the T cell co-stimulatory molecules, or each of a plurality of the T cell co-stimulatory molecules into the cell culture medium of the TILs separately.

Embodiment 22. The method according to any one of embodiments 1-18 and 20, wherein the method comprises adding a plurality of the T cell co-stimulatory molecules simultaneously into the cell culture medium of the TILs.

Embodiment 23. The method according to any one of embodiments 1-19 and 21, wherein the one of the T cell co-stimulatory molecules is added into the cell culture medium of the TILs in one or more of the forms selected from the group consisting of: engineered cells expressing the T cell co-stimulatory molecule, nanoparticles comprising the T cell co-stimulatory molecule, and polymers comprising the T cell co-stimulatory molecule.

Embodiment 24. The method according to any one of embodiments 1-18, 20 and 22, wherein the plurality of the T cell co-stimulatory molecules are added into the cell culture medium of the TILs in forms selected from the group consisting of: mixtures, fusion proteins, engineered cells expressing the plurality of the T cell co-stimulatory molecules, nanoparticles comprising the plurality of the T cell co-stimulatory molecules, and polymers comprising the plurality of the T cell co-stimulatory molecules.

Embodiment 25. The method according to any one of embodiments 1-24, wherein the T cell growth factor is one or more of the factors selected from the group consisting of: IL-2, IL-4, IL-7, IL-10, IL-12, IL-15, IL-21, and interferon gamma.

Embodiment 26. The method according to any one of embodiments 1-25, wherein the T cell growth factor is one or more of the factors selected from the group consisting of: IL-2, IL-7, IL-12, IL-15, IL-21, and interferon gamma.

Embodiment 27. The method according to any one of embodiments 1-26, wherein the T cell growth factor is IL-2 and/or a functionally active fragment thereof.

Embodiment 28. The method according to any one of embodiments 1-27, wherein the initial concentration of IL-2 in the cell culture medium of the TILs is at least 1000 IU/mL.

Embodiment 29. The method according to any one of embodiments 1-28, wherein the method comprises contacting one of the T cell growth factors, or each of a plurality of the T cell growth factors with the TILs individually.

Embodiment 30. The method according to any one of embodiments 1-28, wherein the method comprises contacting a plurality of the T cell growth factors with the TTLs simultaneously.

Embodiment 31. The method according to any one of embodiments 1-29, wherein the method comprises adding one of the T cell growth factors, or each of a plurality of the T cell growth factors into the cell culture medium of the TILs separately.

Embodiment 32. The method according to any one of embodiments 1-28 and 30, wherein the method comprises adding a plurality of the T cell growth factors simultaneously into the cell culture medium of the TILs.

Embodiment 33. The method according to any one of embodiments 1-29 and 31, wherein the one of the T cell growth factors is added into the cell culture medium of the TILs in one or more of the forms selected from the group consisting of: engineered cells expressing the T cell growth factor, nanoparticles comprising the T cell growth factor, and polymers comprising the T cell growth factor.

Embodiment 34. The method according to any one of embodiments 1-28, 30 and 32, wherein the plurality of the T cell growth factors are added into the cell culture medium of the TTLs in one or more of the forms selected from the group consisting of: mixtures, fusion proteins, engineered cells expressing the plurality of the T cell growth factors, nanoparticles comprising the plurality of the T cell growth factors, and polymers comprising the plurality of the T cell growth factors.

Embodiment 35. The method according to any one of embodiments 1-34, wherein the TTLs are TILs which are derived from fragments of the tumor tissue.

Embodiment 36. The method according to embodiment 35, wherein the fragments have a volume of about 1-27 mm3.

Embodiment 37. The method according to any one of embodiments 35-36, wherein the fragments have a volume of about 27 mm3.

Embodiment 38. The method according to any one of embodiments 1-37, wherein the feeder cells comprise antigen presenting cells.

Embodiment 39. The method according to any one of embodiments 1-38, wherein the feeder cells comprise one or more of the cells selected from the group consisting of: peripheral mononuclear cells, dendritic cells, and artificial antigen presenting cells.

Embodiment 40. The method according to any one of embodiments 1-39, wherein the feeder cells are peripheral mononuclear cells.

Embodiment 41. The method according to any one of embodiments 1-40, wherein the feeder cells are irradiated feeder cells.

Embodiment 42. The method according to any one of embodiments 1-41, wherein the co-culture of the TILs with the feeder cells comprises contacting the surfaces of the feeder cells with the surfaces of the TILs.

Embodiment 43. The method according to any one of embodiments 1-42, wherein the co-culture of the TILs with the feeder cells comprises adding the feeder cells into the cell culture medium of the TTLs.

Embodiment 44. A tumor infiltrating lymphocyte (TIL), wherein the TIL is obtainable by the method of any one of embodiments 1 to 43.

Embodiment 45. A composition, comprising the TIL of embodiment 44.

Embodiment 46. A pharmaceutical composition, comprising the TIL of embodiment 44 and/or the composition of embodiment 45, and optionally a pharmaceutically acceptable carrier.

Embodiment 47. A method for affecting tumor cell growth, comprising administering to a subject the TIL of embodiment 44 and/or the pharmaceutical composition of embodiment 46.

Embodiment 48. Use of the TIL as defined in embodiment 44 and/or the pharmaceutical composition as defined in embodiment 46 for the manufacture of a medicament for preventing and/or treating tumors.

Embodiment 49. The use according to embodiment 48, wherein the tumors are selected from solid tumors.

Embodiment 50. The use according to any one of embodiments 48 to 49, wherein the tumors are one or more of the tumors selected from the group consisting of: melanoma, ovarian cancer, cervical cancer, lung cancer, bladder cancer, breast cancer, head and neck cancer, pancreatic cancer, liver cancer, stomach cancer, colorectal cancer, and kidney cancer.

Embodiment 51. A method for preventing and/or treating tumors, comprising administering to a subject the TIL as defined in embodiment 44 and/or the pharmaceutical composition as defined in embodiment 46.

Embodiment 52. The method according to embodiment 51, wherein the tumors are selected from solid tumors.

Embodiment 53. The method according to any one of embodiments 51 to 52, wherein the tumors are one or more of tumors selected from the group consisting of: melanoma, ovarian cancer, cervical cancer, lung cancer, bladder cancer, breast cancer, head and neck cancer, pancreatic cancer, liver cancer, stomach cancer, colorectal cancer, and kidney cancer.

Embodiment 54. A TIL as defined in embodiment 44 and/or a pharmaceutical composition as defined in embodiment 46 for use in preventing and/or treating tumors.

Embodiment 55. A TIL as defined in embodiment 44 and/or a pharmaceutical composition as defined in embodiment 46 for use in preventing and/or treating tumors, wherein the tumors are selected from solid tumors.

Embodiment 56. A TIL as defined in embodiment 44 and/or a pharmaceutical composition as defined in embodiment 46 for use in preventing and/or treating tumors, wherein the tumors are one or more of tumors selected from the group consisting of: melanoma, ovarian cancer, cervical cancer, lung cancer, bladder cancer, breast cancer, head and neck cancer, pancreatic cancer, liver cancer, stomach cancer, colorectal cancer, and kidney cancer.

Not to be limited by any theory, the following examples are only used to illustrate the culture methods of the TILs and the use in the present application, and are not intended to limit the scope of the invention of the present application.

EXAMPLES

Example 1 Method for Culturing Tumor Infiltrating Lymphocyte (TIL) Cells 1.1 Reception and Preparation of Feeder Cells
1.1.1 Reception of Apheresis Blood The information of the apheresis blood, batch numbers and volumes were recorded, and the blood sample was rewarmed to room temperature.

1.1.2 Manual Isolation and Cryopreservation of PBMCs (Peripheral Blood Mononuclear Cells)

The blood bag was sterilized with 75% alcohol and transferred into a biosafety cabinet. After the blood bag cutting with one sterile scissor, the apheresis blood was transferred into 50 mL centrifuge tubes. The blood bag was washed with 20 mL PBS or normal saline injected by a 20 mL syringe. The washing solution was also transferred into the 50 mL centrifuge tubes. The liquid volume in each 50 mL centrifuge tube should not exceed 30 mL. The apheresis blood within the tube was centrifuged at 3000 g for 10 minutes. During the centrifugation, 6-8 tubes of 50 mL centrifuge tubes were prepared, into which should be added a pre-warmed lymphocyte separation solution (Ficoll, Tianjin Haoyang), 20 mL/tube. After the centrifugation, the upper layer of plasma was discarded, and the cell pellets were diluted with PBS or normal saline. The diluted blood cell mixture solution was slowly added dropwise onto the upper layer of the lymphocyte separation solution without destroying the interface at about 25 mL of samples per tube, and the final volume within each tube should be no more than 28 mL.

Centrifugation was carried out at temperature of 18-22° C. and 500-600 g for 15-30 minutes using a horizontal rotor. After centrifugation, the resulting buffy coat will be at the interface between normal saline and Ficoll. The upper layer of plasma and normal saline were aspirated off, and the middle buffy coat was transferred to another 50 mL sterile centrifuge tube with a pipette. The collected buffy coat was diluted with PBS or normal saline and centrifuged at room temperature and 600 g for 10 minutes. After the centrifugation was completed, the supernatant was discarded. The cells were washed once with PBS or normal saline, and centrifuged at room temperature and 500 g for 5 minutes.

If there were lots of remanent red blood cells, the red blood cells should be lysed after the centrifugation. A red blood cell lysis solution was added at a volume ratio of 1:2 to 1:3 of the cell pellets to the red blood cell lysis solution, and mixed well. Red blood cells lysis at room temperature for 10 minutes, the centrifuge tubes were gently mixed 2-3 times to ensure the lysis effect. After the lysis was completed, PBS or normal saline were added to wash the cells. After the lysis, the cells were washed twice, centrifuged at 400 g for 6 minutes, and counted before the last centrifugation.

The supernatant was discarded, the cells were resuspended in the basic medium with a cell density adjusted to about $2-3\times10^7$/mL, wherein the liquid level should be not higher than 1 cm, and the volume in each T225 culture flask should be less than 200 mL. The suspension was irradiated with X-rays at 50 Gy in the tiled state. The supernatant was discarded after centrifugation, and the cells were cryopreserved according to the counting results in about $1-2\times10^8$/mL and 1-2 mL/tube. The cells were placed in a programmed cooling box and transferred to a −80° C. freezer for cryopreservation.

1.1.3 Automatic Isolation and Cryopreservation of PBMCs

The tubing of the blood bag was connected to the input end of a cpro separation kit (Cytiva) aseptically. If the blood volume was more than 120 mL, a pre-concentration step should be performed to concentrate the blood volume to within 120 mL. A neatcell procedure should be used to isolate and wash PBMCs, wherein the washing solution was normal saline, and the intermediate volume was 20 mL; the resuspending solution was the basic medium, and 80 mL/batch was added. After isolation, the PBMCs of each donor were 100 mL per bag, wherein when in the tiled state, the liquid level should be no more than 1 cm, and the suspension was irradiated with X-rays at 50 Gy. Sampling and counting were carried out after irradiation. The PBMC suspensions of 3-5 donors were mixed according to the ratio of 0.5:1 to 1:2. Cells were collected and washed three times using a culture wash procedure, and the washing solution was normal saline; the intermediate volume and the final volume were set, so that the volume reached no less than 2 mL/$1\times10^9$ cells; an equal to 2-fold cryopreservation solution was added and mixed well. The cell density was adjusted to about $1\times10^7$/mL to $2\times10^8$/mL with a 1-fold cryopreservation solution. The suspension was divided into 20 mL/bag, cryopreserved in a programmed cooler, and stored in liquid nitrogen.

1.2 Reception and Processing of Tumor Tissues 1.2.1 Reception of Tissues

Tumor tissues and blood samples were received from donors. The sample information was checked and recorded, and corresponding sample labels were printed.

1.2.2 Tissue Processing and Culture

The sample tubes and blood collection tubes were sterilized with 75% alcohol and transferred into a biosafety cabinet. The PBMC cells in the blood samples were isolated and cryopreserved according to the above procedures for manual isolation and cryopreservation of PBMCs. A kind of culture flasks and bags with gas permeable surfaces, e.g. G-Rex100 culture flasks (Wilson Wolf Manufacturing) were taken. A 300 mL rewarmed complete medium was added, which could optionally select X-vivo 15 medium or other commercially available T cell culture media, e.g., T cell culture media of Stem Cell, Lonza, Thermo, Miltenyi brands etc., and into which essential amino acids and antibiotics could be added. IL-2 was added at a concentration of about 1000~9000 IU/mL, e.g., 6000 IU/mL of IL-2. Several 10 cm culture dishes were taken, into which was added an appropriate amount of a medium. The tumor tissues were taken out from the sample tubes into the 10 cm culture dishes using sterile ophthalmic forceps. The amount of the medium was such that the tumor tissues were just immersed. The tissue morphology was observed and recorded. The tissues were washed and the culture dishes were replaced. The tissues were cut initially using ophthalmic scissors and ophthalmic forceps to remove fatty tissues and necrotic tissues. Each tissue piece was further cut to a size of about 27 mm3. Non-suspended tumor tissue pieces were taken. 20 mL syringes were used after removing the inner pistons to connect the culture bags. About 1 g of the tissue pieces were transferred into the culture bags through the syringes using pipettes. The culture bags were placed in a carbon dioxide incubator to culture. The scissors and forceps were preliminary disinfected with 75% alcohol after cleaning, and sterilize after ultrasonic cleaning, to obtain primary TILs.

1.3 First Stage of Expansion and Harvest 1.3.1 First Stage of Expansion

According to the cell growth status, the medium was replenished or half-changed every 3-7 days to ensure cell nutrition. A complete medium was used, which should optionally select X-vivo 15 medium or other commercially available T cell culture media, e.g. T cell culture media of Stem Cell, Lonza, Thermo, Miltenyi brands etc., and into which essential amino acids and antibiotics should be added. TL-2 was added at a concentration of about 1000-9000 IU/mL, e.g., 6000 IU/mL of IL-2. Sampling and counting were carried out on days 3-14, e.g. on days 3, 4, 5, 6, 7, 8, 9, 10, 11, 12, 13, or 14, of the first stage of the expansion. If the cell number were between $5\times10^5$ and $5\times10^8$, the cells entered the harvest step of the first stage of the expansion described below.

1.3.2 Harvest of First Stage of Expansion

The cells at the end of the first stage of the expansion were collected, and centrifuged. The medium was discarded. The cells were washed once with PBS or normal saline to obtain the TILs subjected to the first stage of the expansion. Sampling and counting were carried out to leave an amount of about $5\times10^5$ to $2\times10^8$ cells to enter the step of the first stage of the expansion described below; an amount of about $5\times10^5$ cells hould be taken for quality control detection; the rest of the cells were added into an equal volume of 2-fold cryopreservation solution to cryopreserve.

1.4 Second Stage of Expansion 1.4.1 Activation of TILs Subjected to Second Stage of Expansion An amount of $5\times10^5$ to $2\times10^8$ cells subjected to the first stage of the expansion was taken. A complete medium was used, which should optionally select X-vivo 15 medium or other commercially available T cell culture media, e.g. T cell culture media of Stem Cell, Lonza, Thermo, Miltenyi brands etc., and into which essential amino acids and antibiotics should be added. The cell density was adjusted to $5\times10^5$ to $2\times10^6$/mL, and the cells were added into the suspension 24-well culture plate at 1 mL/well. A CD3 antibody, for example, about 30 ng/mL of OKT3 was added. IL-2 was added at a concentration of about 1000-9000 IU/mL, e.g., 6000 IU/mL of IL-2.

1.4.2 Expanded Culture for Second Stage of Expansion

In the second stage of the expansion, some time $T_n$ later than adding OKT3 and IL-2 ($T_n$ could be from 0 hours to 14 days), the feeder cells mixed from 1-5 donors were resuscitated; the activated TIL cells, tissue pieces and feeder cells were transferred into G-Rex100 culture flasks or gas-permeable bags, into which the complete medium was supplemented. Sampling and counting were carried out every 1-3 days, and the medium was replenished or half-changed according to the cell status until the total number of the cells were greater than $1\times10^9$, or the culture time of the second-stage of the expansion reached 14 days, then the culture was terminated.

1.4.3 Harvest of Tumor Infiltrating Lymphocytes

The TILs subjected to the second stage of the expansion were obtained by taking the cells subjected to the second stage of the expansion, discarding the supernatant of the medium after centrifugation, and washing three times with PBS or normal saline or a compound electrolyte solution. Sampling and counting were carried out during the third washing. According to the counting results, the supernatant was discarded after the last centrifugation, and $3 \times 10^6$ cells were taken for quality control detection; all the remaining cells were added to the cryopreservation solution, and the cell density was adjusted to $1-3 \times 10^8$/mL for cryopreservation.

1.5 Application of Tumor Infiltrating Lymphocytes

Resuscitated therapeutic tumor infiltrating lymphocytes could be administered to a subject by intravenous infusion.

Example 2 Comparison of Proliferation Abilities of TILs Cultured with Feeder Cells Added at Different Times In the activation of TILs subjected to second stage of expansion in 1.4 of Example 1, some time $T_n$ later than adding OKT3 and IL-2 ($T_n$ could be from 0 hours to 14 days), the feeder cells were added to the culture bags of tumor Infiltrating lymphocytes. In this example, $T_n$ selected from 0 hours, 6 hours, 12 hours, 24 hours, 48 hours, 72 hours, 5 days, 7 days, and 9 days to obtain TILs cultured with feeder cells added at different times, and a comparison experiment of cell counting was carried out.

The analysis of the proliferation abilities of the TILs cultured with the feeder cells added at different times is shown in FIG. 1. The numerical values of the ordinate, in each group of graphs of the TILs cultured with the feeder cells added at different times, represent the fold to which the number of the TIL cells was expanded after the end of the second stage of the expansion compared to before the start of the second stage of the expansion. The proliferation results of the TILs which are derived from 4 donors showed that the proliferation abilities of the TILs cultured with the feeder cells added 0 hours after addition of OKT3 and IL-2 (i.e., at the same time) were weaker than the TILs cultured with the feeder cells added 24 hours or 48 hours after addition of OKT3 and IL-2.

Example 3 Comparison of Flow Detection of TILs Cultured with Feeder Cells Added at Different Times In the activation of TILs subjected to second stage of expansion in 1.4 of Example 1, some time Tn after adding OKT3 and IL-2 (Tn could be from 0 hours to 14 days), the feeder cells were added to the culture bags of tumor Infiltrating lymphocytes. In this example, $T_n$ selected from 0 hours, 6 hours, 12 hours, 24 hours, 48 hours, 72 hours, 5 days, 7 days, and 9 days to obtain TILs cultured with feeder cells added at different times, and a comparison experiment of flow detection was carried out.

Sources of TIL Flow Detection Experiment Materials

Transcription Factor Buffer Set, manufacturer BD, product number 562574; V-bottom 96-well plate, manufacturer Corning, product number 3894; flow tube, manufacturer Corning, product number 352052.

The flow antibodies in this example were purchased from BD or Biolegend. $1 \times 10^5$ to $5 \times 10^5$ cell samples per group were added into flow tubes or V-bottom 96-well plates. Centrifugation was performed at 600 g for 3 minutes and the supernatant was discarded. Washing was carried out once using PBS, with 1 mL/tube for flow tubes, and 250 µL/well for 96-well plates, and the supernatant was discarded. A prepared antibody working solution was added for cell surface staining. The concentration of the antibody (BD or Biolegend) was 1:100 to 1:200, and the activity detection dye was contained in 1:10000. Staining was carried out with 100 µL/tube for flow tubes, and 50 µL/well for 96-well plates, and incubating was performed at 2-8° C. in dark for 30 minutes. Preparing reagents required for transcription factor staining during the staining process: Transcription Factor Buffer Set (BD) was used to dilute a 4×Fixation/Permeabilization Solution (BD) to produce 1×working solution A; double distilled water was used to dilute a 5×Perm/Wash Buffer (BD) to produce 1×working solution B. They were pre-cooled at 4 degrees for use. After staining, an appropriate amount of PBS was added to wash cells twice (250 µL/time for 96-well plates, 1 mL/time for flow tubes). Centrifugation was performed at 600 g for 3 minutes. After the centrifugation, the supernatant was discarded. Cell fixation and permeabilization: the Cells were sufficiently resuspended. An appropriate amount (100 µL/well for 96-well plates, and 1 mL/tube for flow tubes) of 1×working solution A was added to fix and permeabilize. Incubating was performed at 2-8° C. in dark for 40-50 minutes. After the fixation and permeabilization were completed, 1×working solution B was added to wash the cells (250 µL/time for 96-well plates, and 2 mL/time for flow tubes). Centrifugation was performed at 2-8° C. and 350 g for 6 minutes, and washing was carried out twice. 1×working solution B was used to prepare intracellular antibodies with 50 µL/well for 96-well plates, and 100 µL/tube for flow tubes, and the antibody concentration was 1:100 to 1:200. Staining was performed at 2-8° C. in dark for 30 minutes. After the Staining was completed, 1×working solution B was added to wash the cells (250 µL/time for 96-well plates, and 2 mL/time for flow tubes). Centrifugation was performed at 2-8° C. and 350 g for 6 minutes, and washing was carried out twice. After the surface staining was completed, PBS was used to wash cells once (250 L/time for 96-well plates, 1 mL/time for flow tubes). Centrifugation was performed at room temperature and 600 g for 3 minutes. After the centrifugation, the supernatant was discarded. The cells were resuspended using 100-500 µL PBS for flow detection on machine.

The analysis of the flow results of the TILs cultured with the feeder cells added at different times is shown in FIGS. 2-8.

Figure 2:
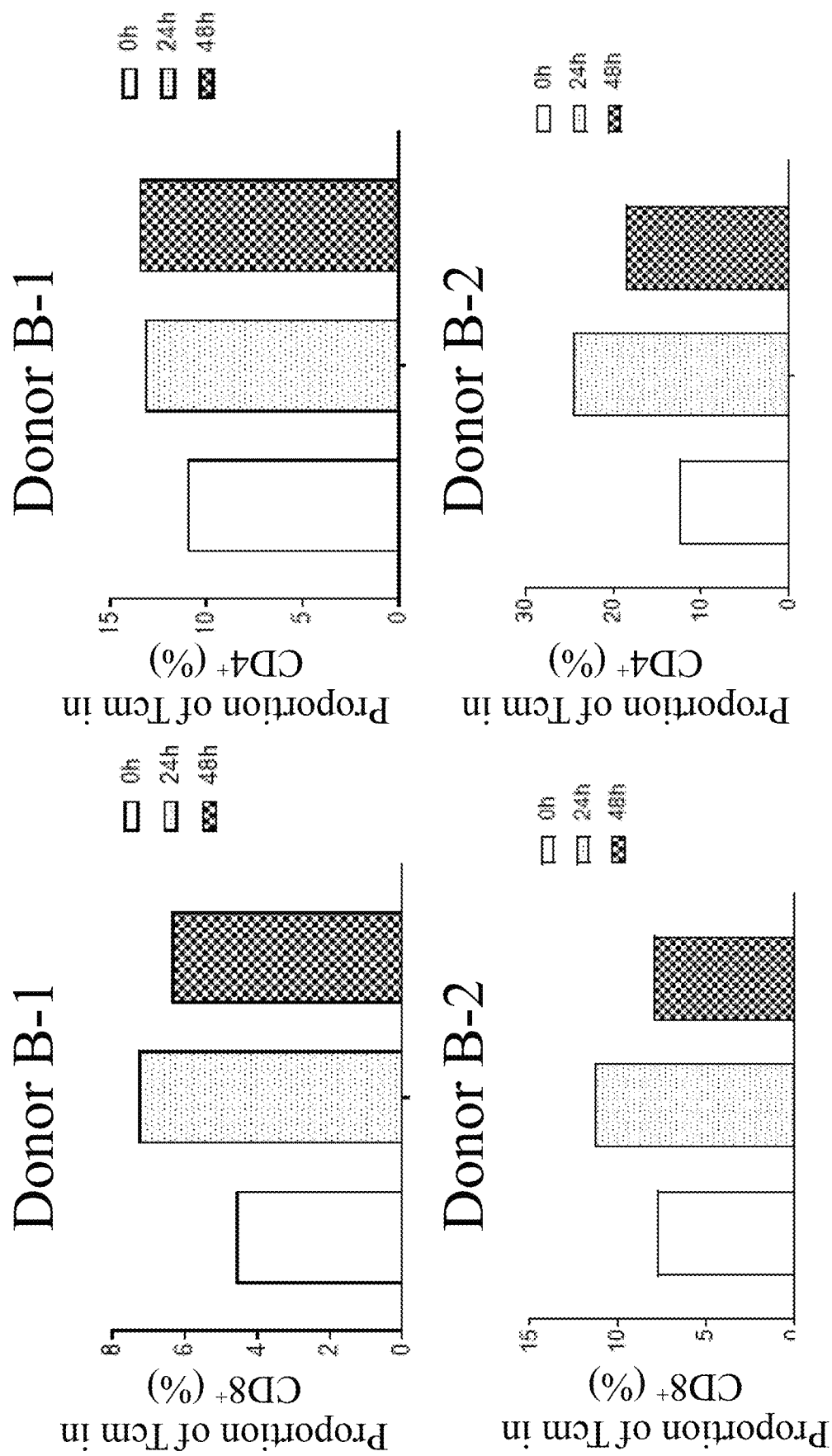
FIG. 2 shows for donors B-1 and B-2, the comparison of the proportion of $CD45RA^- CCR7^+$ central memory T cells (Tcm) in $CD8^+$ or in $CD4^+$ in TILs cultured with feeder cells added at 0, 24 or 48 hours after addition of OKT3 and IL-2.
Figure 3:
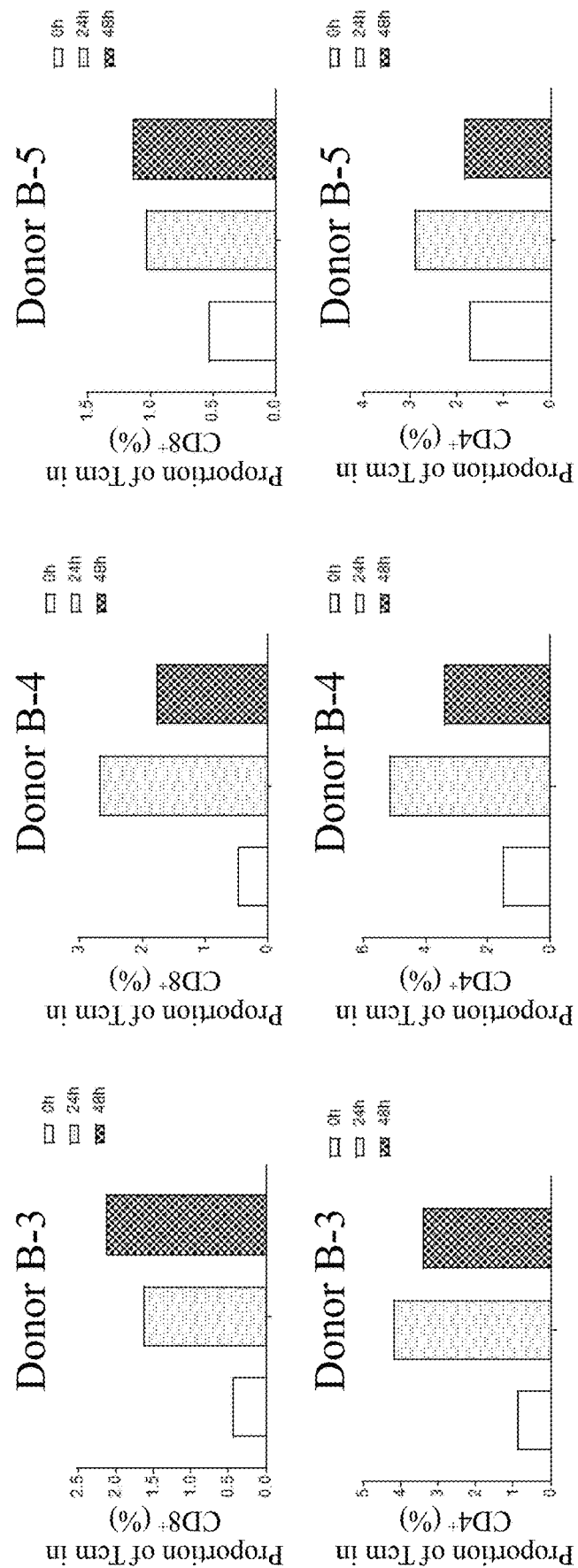
FIG. 3 shows for donors B-3, B-4 and B-5, the comparison of the proportion of $CD45RA^-CCR7^+$ central memory T cells (Tcm) in $CD8^+$ or in $CD4^+$ in TILs cultured with feeder cells added at 0, 24 or 48 hours after addition of OKT3 and IL-2.

FIGS. 2-3 show the ratio of $CD45RA^-CCR7^+$ central memory T cells (Tcm) of TIL cells obtained by culturing TILs with feeder cells added at 0, 24 or 48 hours after addition of OKT3 and IL-2. The results show that the TILs cultured with the feeder cells added at 24 hours or 48 hours had higher ratio of central memory T cells than the TILs cultured with the feeder cells added at the same time.

Figure 4:
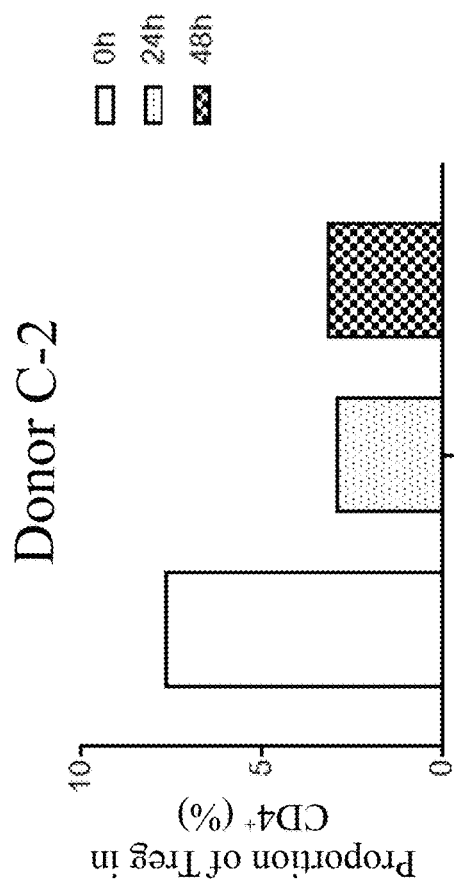
FIG. 4 shows for donors C-1 and C-2, the comparison of the proportion of $CD4^+CD25^+Foxp3^+$ regulatory T cells (Treg) in TILs cultured with feeder cells added at 0, 24 or 48 hours after addition of OKT3 and IL-2.
Figure 4:
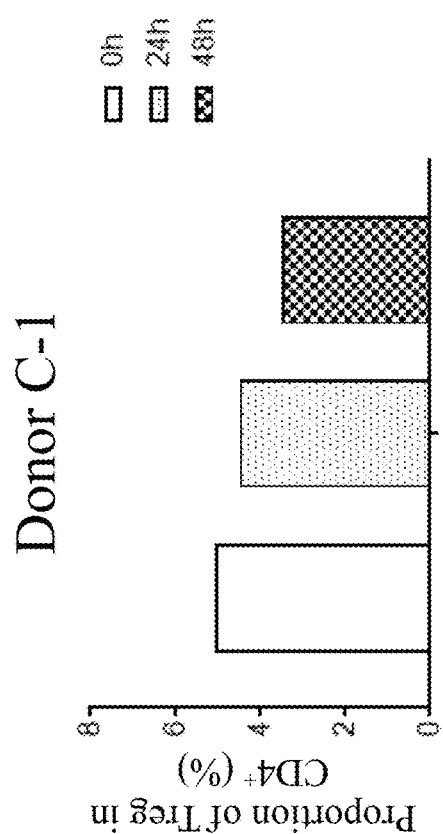

FIG. 4 shows the ratio of $CD4^+CD25^+Foxp3^+$ regulatory T cells (Treg) of TIL cells obtained by culturing TILs with feeder cells added at 0, 24 or 48 hours after addition of OKT3 and IL-2. The results show that the TILs cultured with the feeder cells added at 24 hours or 48 hours had lower ratio of regulatory T cells than the TILs cultured with the feeder cells added at the same time.

Figure 5:
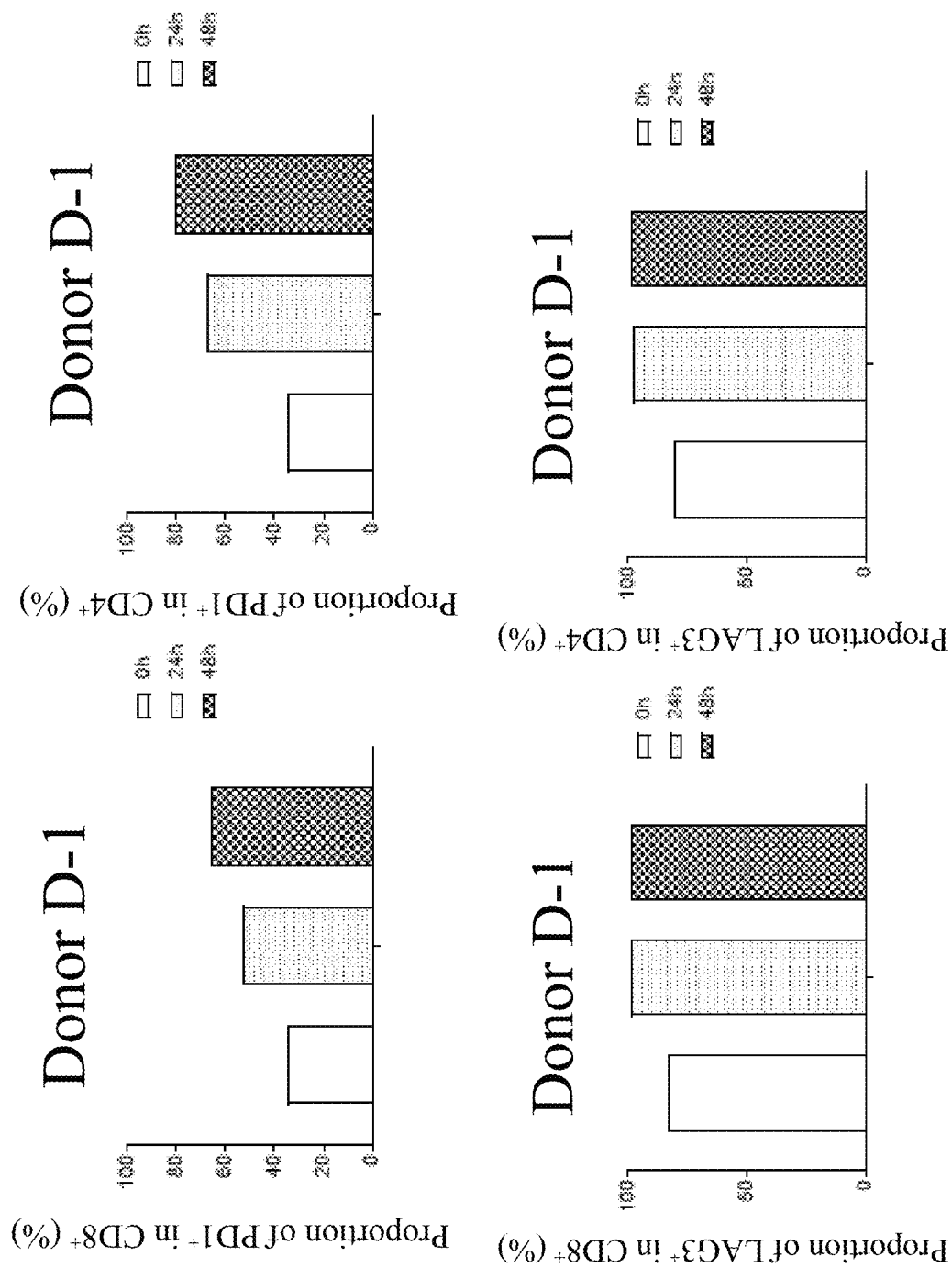
FIG. 5 shows for donors D-1 and D-2, the comparison of the proportion of PD1V activated T cells and $LAG3^+$ activated T cells in $CD8^+$ or in $CD4^+$ in TILs cultured with feeder cells added at 0, 24 or 48 hours after addition of OKT3 and IL-2.
Figure 5:
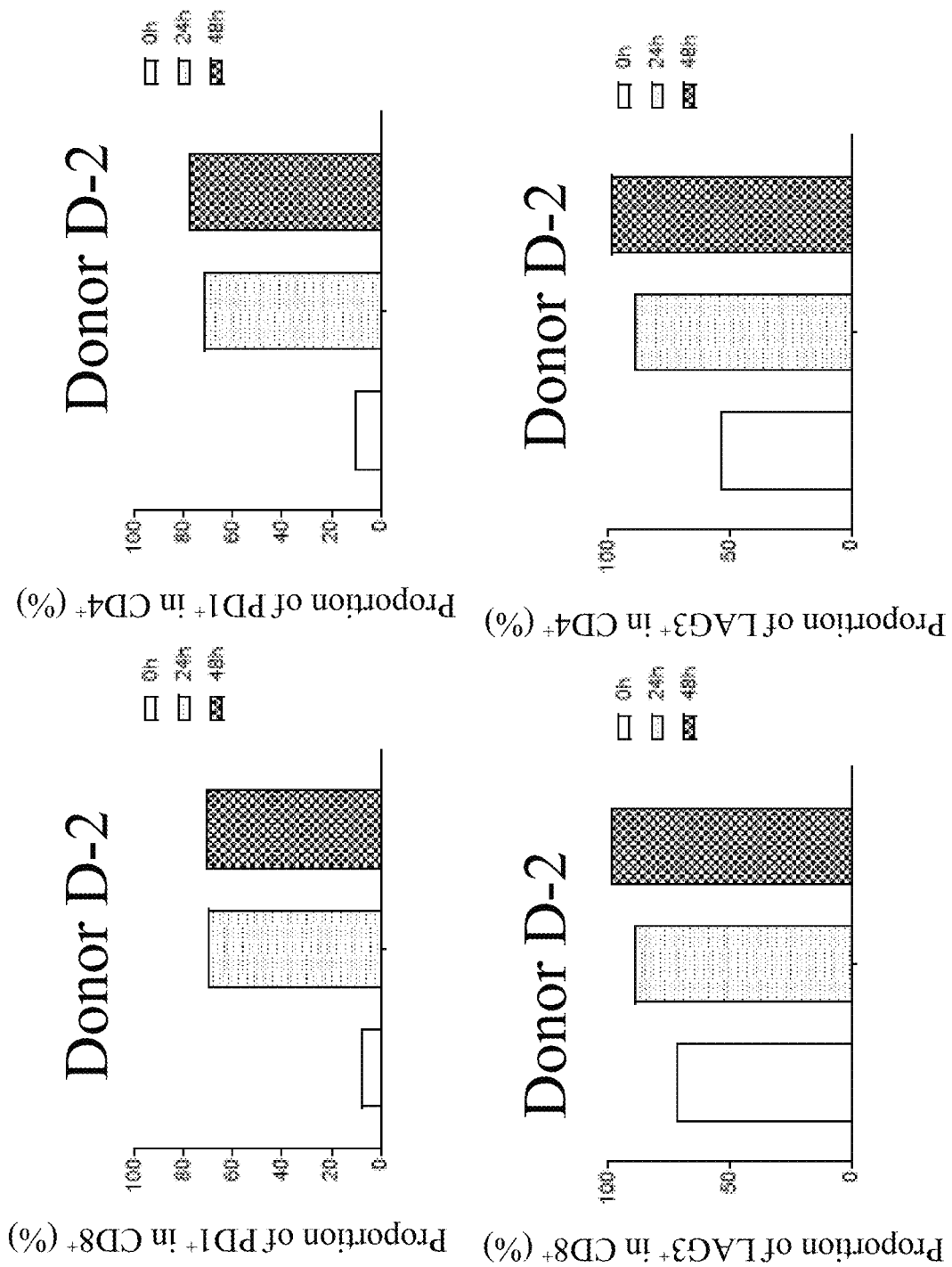
Figure 6:
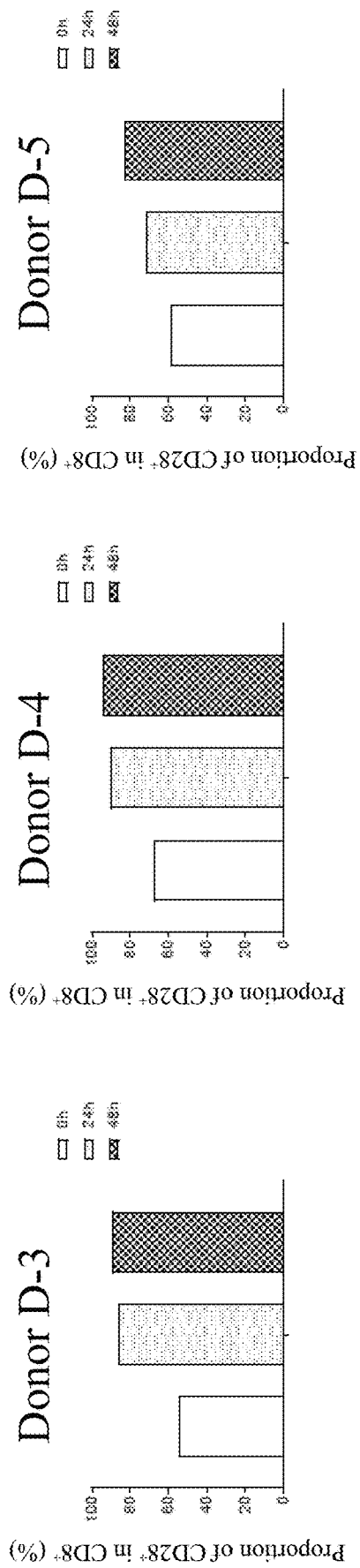
FIG. 6 shows for donors D-3, D-4 and D-5, the comparison of the proportion of $CD28^+$ activated T cells in $CD8^+$ in TILs cultured with feeder cells added at 0, 24 or 48 hours after addition of OKT3 and IL-2.

FIGS. 5-6 show the ratio of activated T cells of TIL cells obtained by culturing TILs with feeder cells added at 0, 24 or 48 hours after addition of OKT3 and IL-2. The results show that the TILs cultured with the feeder cells added at 24 hours or 48 hours had higher ratio of activated T cells, for example higher ratio of PD1$^+$, LAG3$^+$ and/or CD28$^+$cells, than the TILs cultured with the feeder cells added at the same time.

Figure 7:
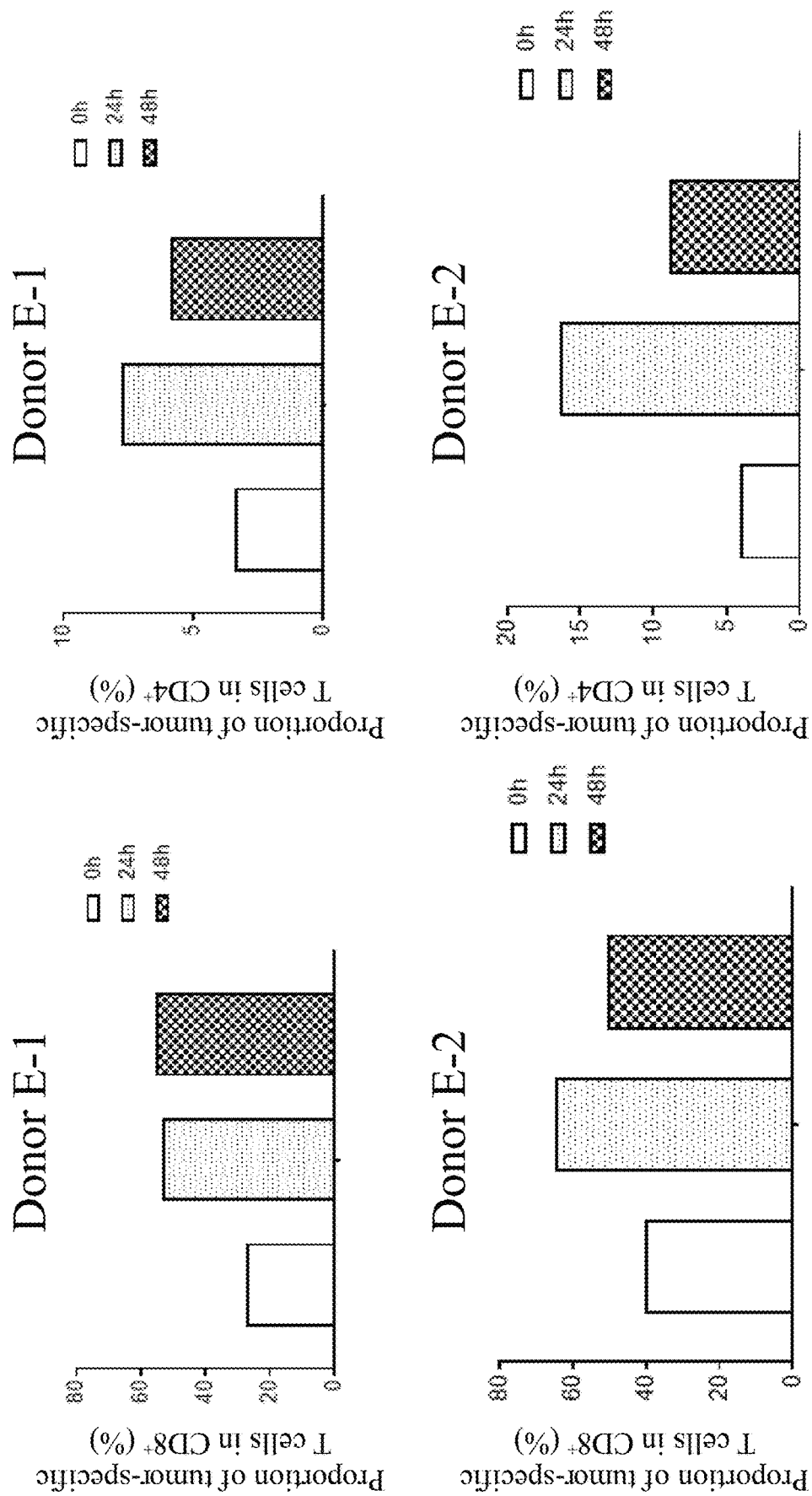
FIG. 7 shows for donors E-1 and E-2, the comparison of the proportion of $CD103^+CD39^+$ tumor-specific T cells in $CD8^+$ or in $CD4^+$ in TILs cultured with feeder cells added at 0, 24 or 48 hours after addition of OKT3 and IL-2.

FIG. 7 shows the ratio of CD103$^+$CD39$^+$ tumor-specific T cells of TIL cells obtained by culturing TILs with feeder cells added at 0, 24 or 48 hours after addition of OKT3 and IL-2. The results show that the TILs cultured with the feeder cells added at 24 hours or 48 hours had higher ratio of tumor-specific T cells than the TILs cultured with the feeder cells added at the same time.

Figure 8:
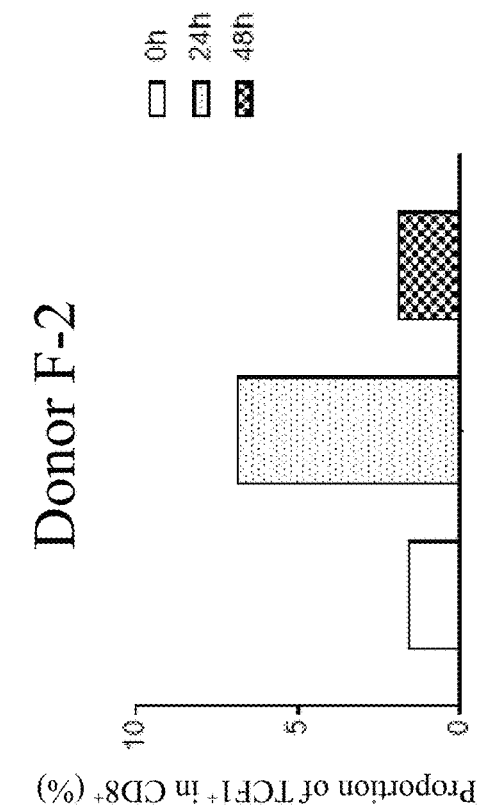
FIG. 8 shows for donors F-1 and F-2, the comparison of the proportion of $TCF1^+$ stem cell-like T cells in TILs cultured with feeder cells added at 0, 24 or 48 hours after addition of OKT3 and IL-2.
Figure 8:
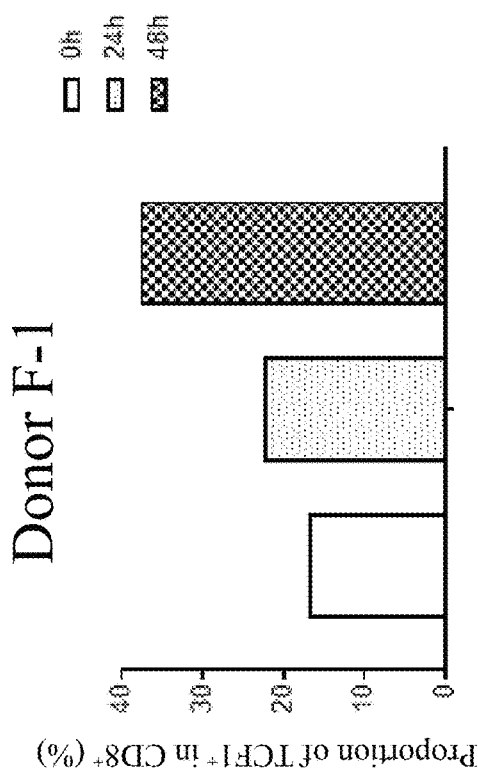

FIG. 8 shows of the ratio of TCF1$^+$ stem cell-like T cells of TIL cells obtained by culturing TILs with feeder cells added at 0, 24 or 48 hours after addition of OKT3 and IL-2. The results show that TILs cultured with the feeder cells added at 24 hours or 48 hours had higher ratio of stem cell-like T cells than the TILs cultured with the feeder cells added at the same time.

Example 4 Statistics of the Results of TILs Cultured with Feeder Cells Added at Different Times In the activation of TILs subjected to second stage of expansion in 1.4 of Example 1, the amount of cells subjected to the first stage of the expansion was taken. The cell density was adjusted to 5×10$^5$ to 2×10$^6$/mL, and the cells were added into the suspension 24-well culture plate at 1 mL/well. A CD3 antibody, for example, about 30 ng/mL of OKT3 was added. IL-2 was added at a concentration of about 1000-9000 IU/mL, e.g., 3000 or 6000 IU/mL of IL-2. 0 hours, 24 hours, and 48 hours after the addition of the above-mentioned OKT3 and IL-2, the feeder cells were added into the culture environment of the tumor infiltrating lymphocytes. Wherein, the TILs and the feeder cells could be added at a ratio of 1:40-1:400. All the cells were collected after culturing for about 9-14 days in the second stage of the expansion, to detect the TILs obtained by the culture and perform statistics on the results of the TILs.

Detection of Proliferation Abilities

Cell counts were performed on the TILs obtained by culturing with feeder cells added at different times.

The TILs which are derived from tumors of different donors were used as different batches; the data of the experiment groups in which OKT3 and IL-2 were added with the feeder cells at the same time (0 h group) in each batch were used as benchmark 1. The data of the experiment groups at other time points in the same batch were normalized, and statistics on the relative proliferation ability of each experiment group in the second stage of the expansion relative to the 0 h group was performed.

Figure 9:
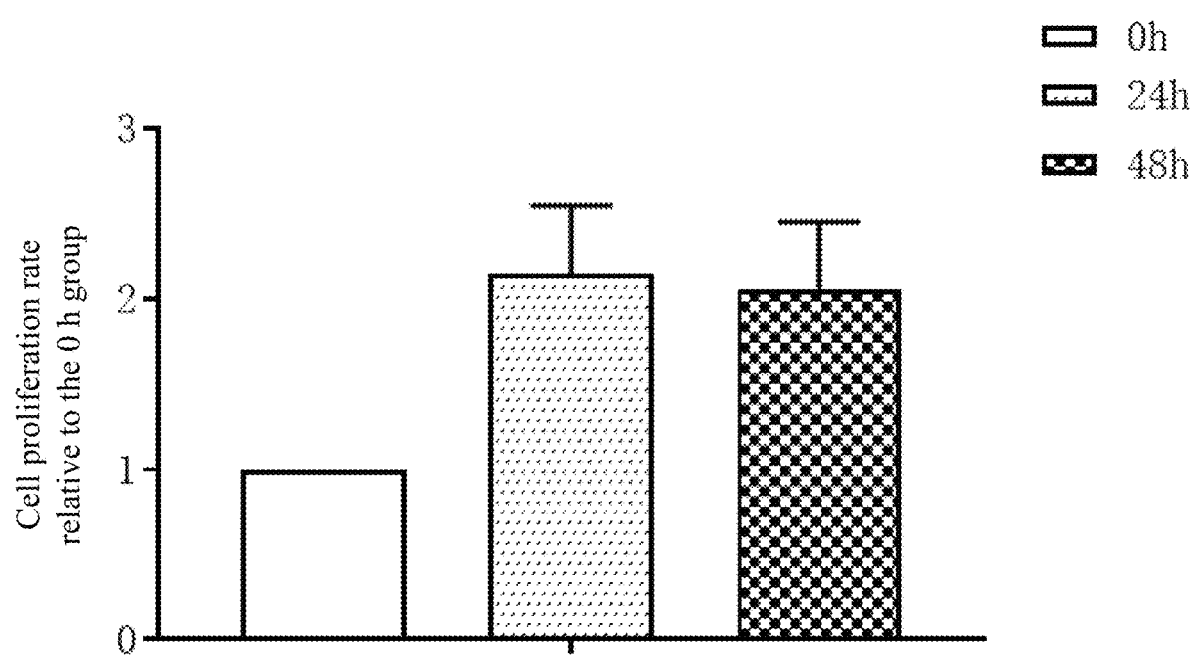
FIG. 9 is a graph showing the results of the cell proliferation abilities of TIL cells obtained by culturing TILs with feeder cells added at 0, 24 or 48 hours after addition of OKT3 and IL-2.

FIG. 9 is a graph showing the results of the cell proliferation abilities of TIL cells obtained by culturing TILs with feeder cells added at 0, 24 or 48 hours after addition of OKT3 and IL-2. The proliferation abilities of the TILs cultured with the feeder cells added after 24 hours or 48 hours after the addition of OKT3 and IL-2 were significantly enhanced relative to the TILs cultured with the feeder cells added 0 hours after (i.e., at the same time) the addition of OKT3 and IL-2.

Flow Detection of TIL Cell Composition

Flow detection was performed on the TIL populations obtained by culturing with above feeder cells added at different times.

The TILs which are derived from tumors of different donors were used as different batches; the data of the experiment groups in which OKT3 and IL-2 were added with the feeder cells at the same time (0 h group) in each batch were used as benchmark 1. The data of the experiment groups at other time points in the same batch were normalized, and statistics on the cell composition ratio of each experiment group in the second stage of the expansion relative to the 0 h group was performed.

For the experiment flow of the flow detection, reference can be made to the content of example 3 of the present application.

Figure 10:
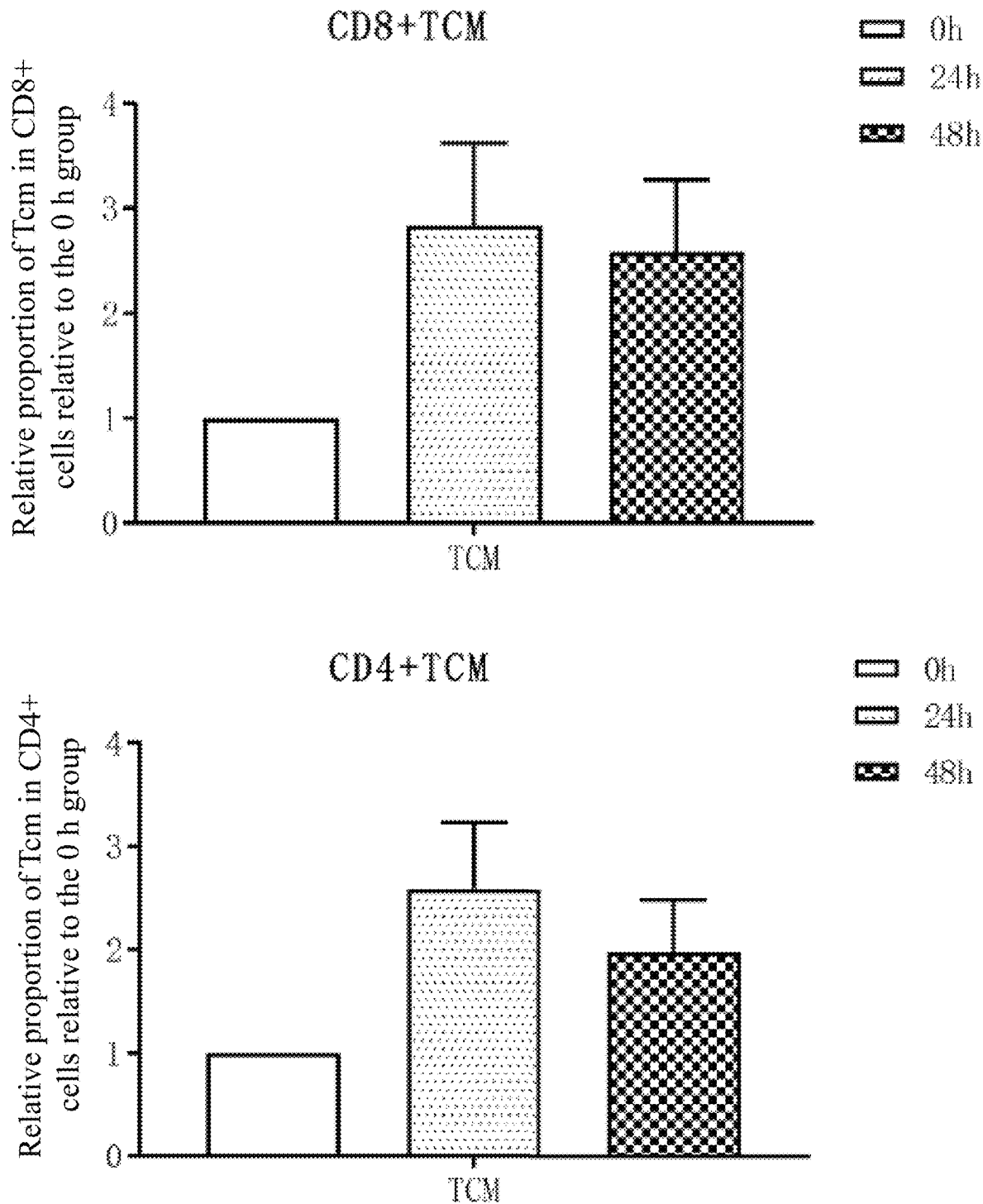
FIG. 10 is a graph showing the results of the proportion of $CD45RA^-CCR7^+$ central memory T cells (Tcm) of TIL cells obtained by culturing TILs with feeder cells added at 0, 24 or 48 hours after addition of OKT3 and IL-2.

FIG. 10 is a graph showing the results of the ratio of CD45RA$^-$CCR7$^+$ central memory T cells (Tcm) of TIL cells obtained by culturing TILs with feeder cells added at 0, 24 or 48 hours after addition of OKT3 and IL-2. The results show that the TILs cultured with the feeder cells added at 24 hours or 48 hours had higher ratio of central memory T cells in CD8$^+$ or in CD4$^+$ than the TILs cultured with the feeder cells added at the same time.

Figure 11:
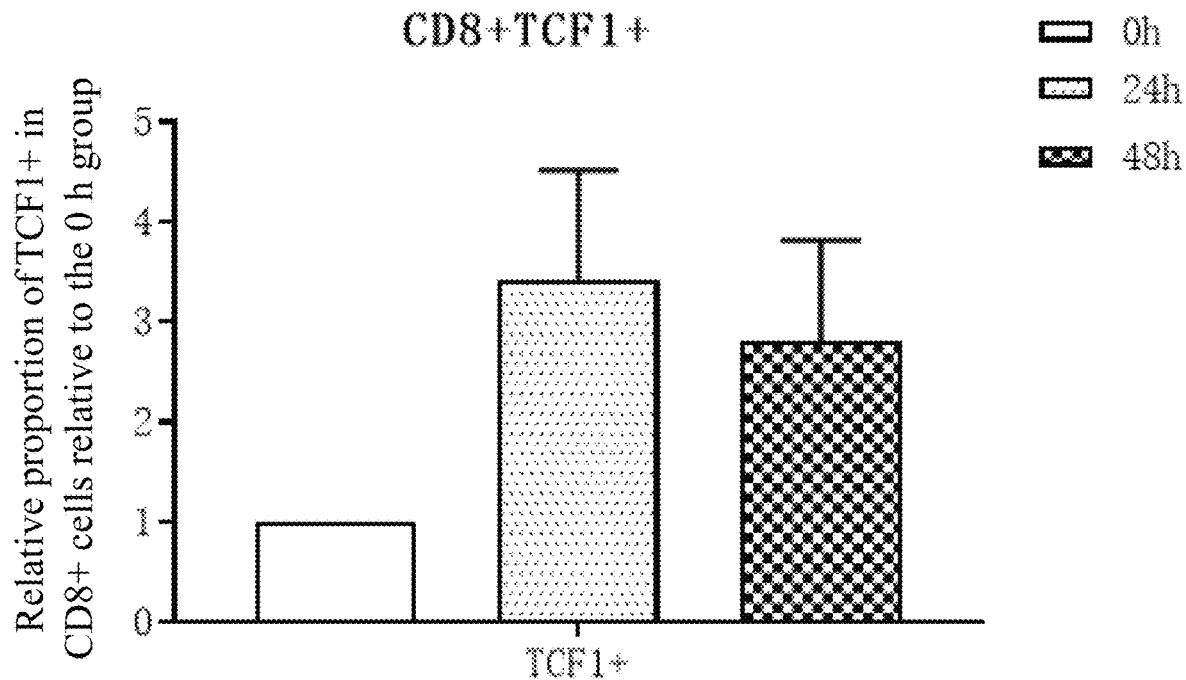
FIG. 11 shows of the proportion of TCF1$^+$ stem cell-like T cells of TIL cells obtained by culturing TILs with feeder cells added at 0, 24 or 48 hours after addition of OKT3 and IL-2.

FIG. 11 shows of the ratio of TCF1$^+$ stem cell-like T cells of TIL cells obtained by culturing TILs with feeder cells added at 0, 24 or 48 hours after addition of OKT3 and IL-2. The results show that the TILs cultured with the feeder cells added at 24 hours or 48 hours had higher ratio of stem cell-like T cells in CD8$^+$ than the TILs cultured with the feeder cells added at the same time.

Figure 12:
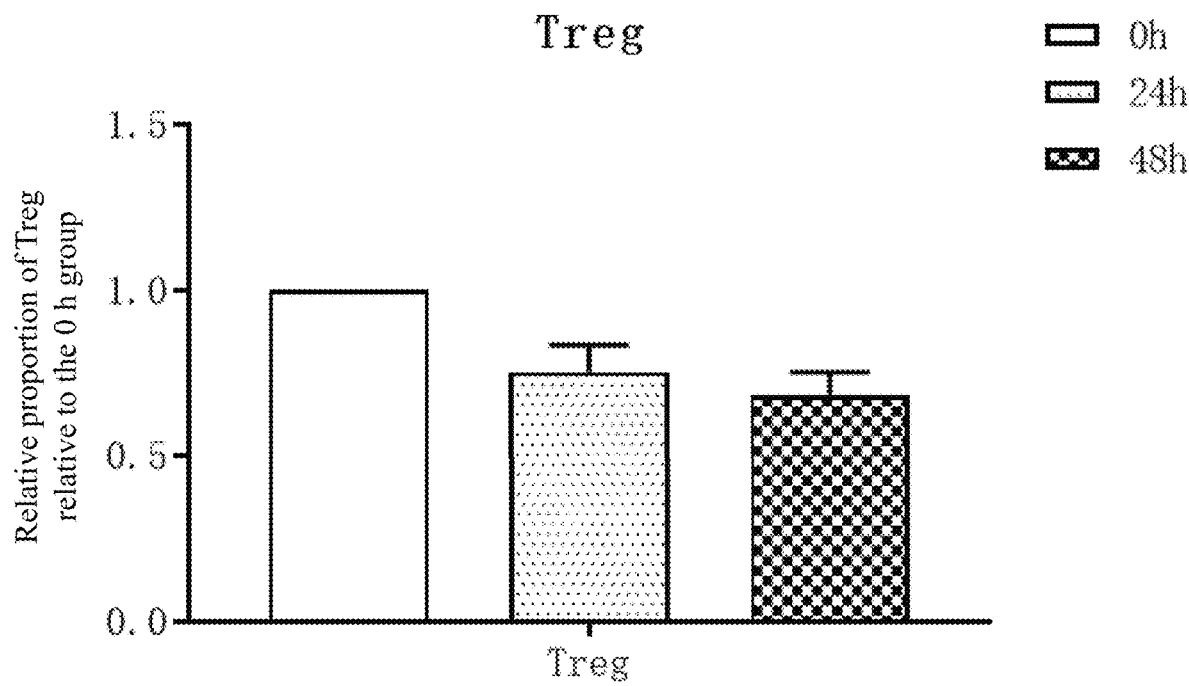
FIG. 12 shows the proportion of CD4$^+$CD25$^+$Foxp3$^+$ regulatory T cells (Treg) of TIL cells obtained by culturing TILs with feeder cells added at 0, 24 or 48 hours after addition of OKT3 and IL-2.

FIG. 12 shows the ratio of CD4$^+$CD25$^+$Foxp3$^+$ regulatory T cells (Treg) of TIL cells obtained by culturing TILs with feeder cells added at 0, 24 or 48 hours after addition of OKT3 and IL-2. The results show that the TILs cultured with the feeder cells added at 24 hours or 48 hours had lower ratio of regulatory T cells than the TILs cultured with the feeder cells added at the same time.

Figure 13:
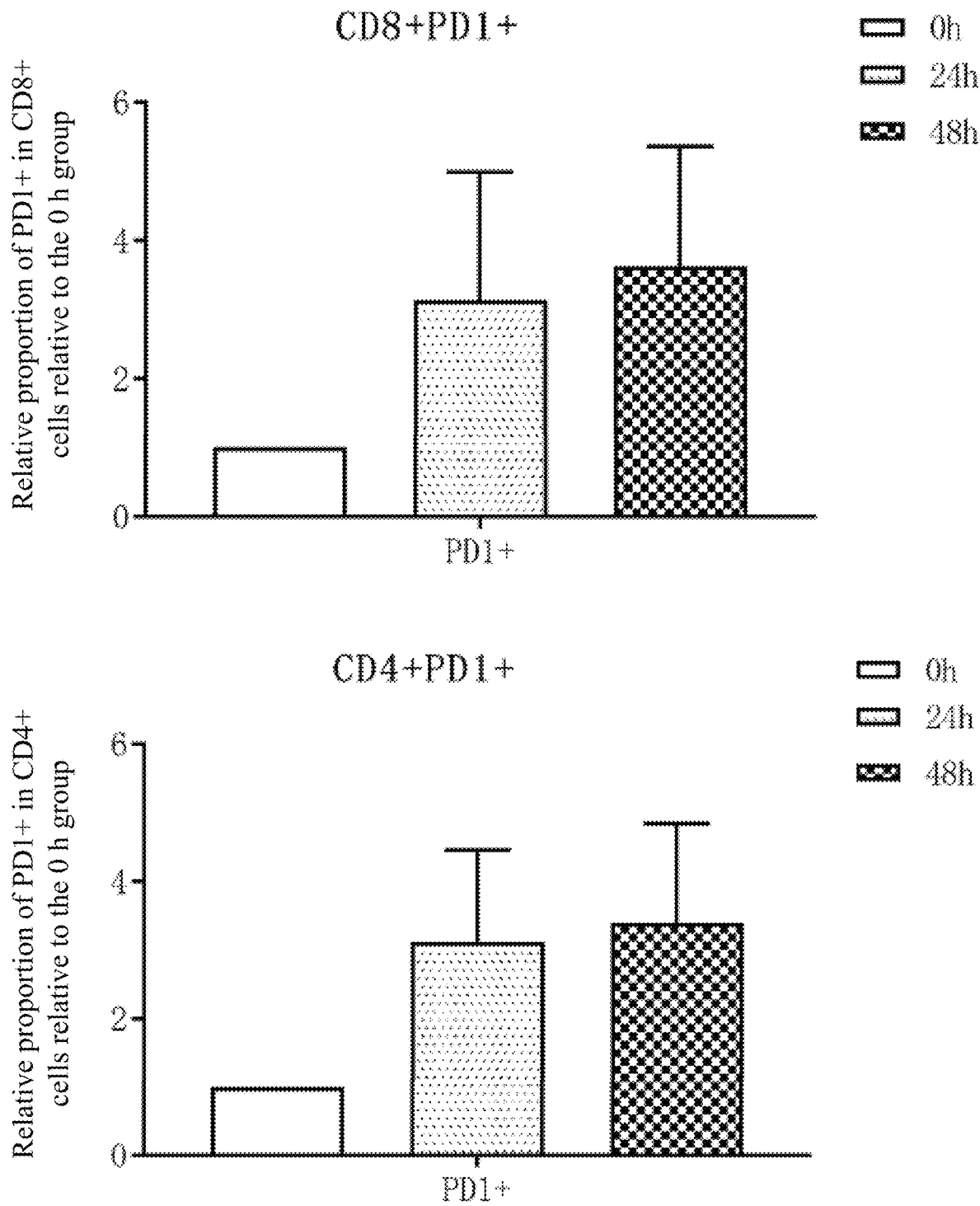
FIG. 13 shows the proportion of activated T cells (PD1$^+$) of TIL cells obtained by culturing TILs with feeder cells added at 0, 24 or 48 hours after addition of OKT3 and IL-2.

FIG. 13 shows the ratio of activated T cells (PD1$^+$) of TIL cells obtained by culturing TILs with feeder cells added at 0, 24 or 48 hours after addition of OKT3 and IL-2. The results show that the TILs cultured with the feeder cells added at 24 hours or 48 hours had higher ratio of activated T cells, for example higher ratio of PD1$^+$ cells in CD8$^+$ and/or in CD4$^+$, than the TILs cultured with the feeder cells added at the same time.

Figure 14:
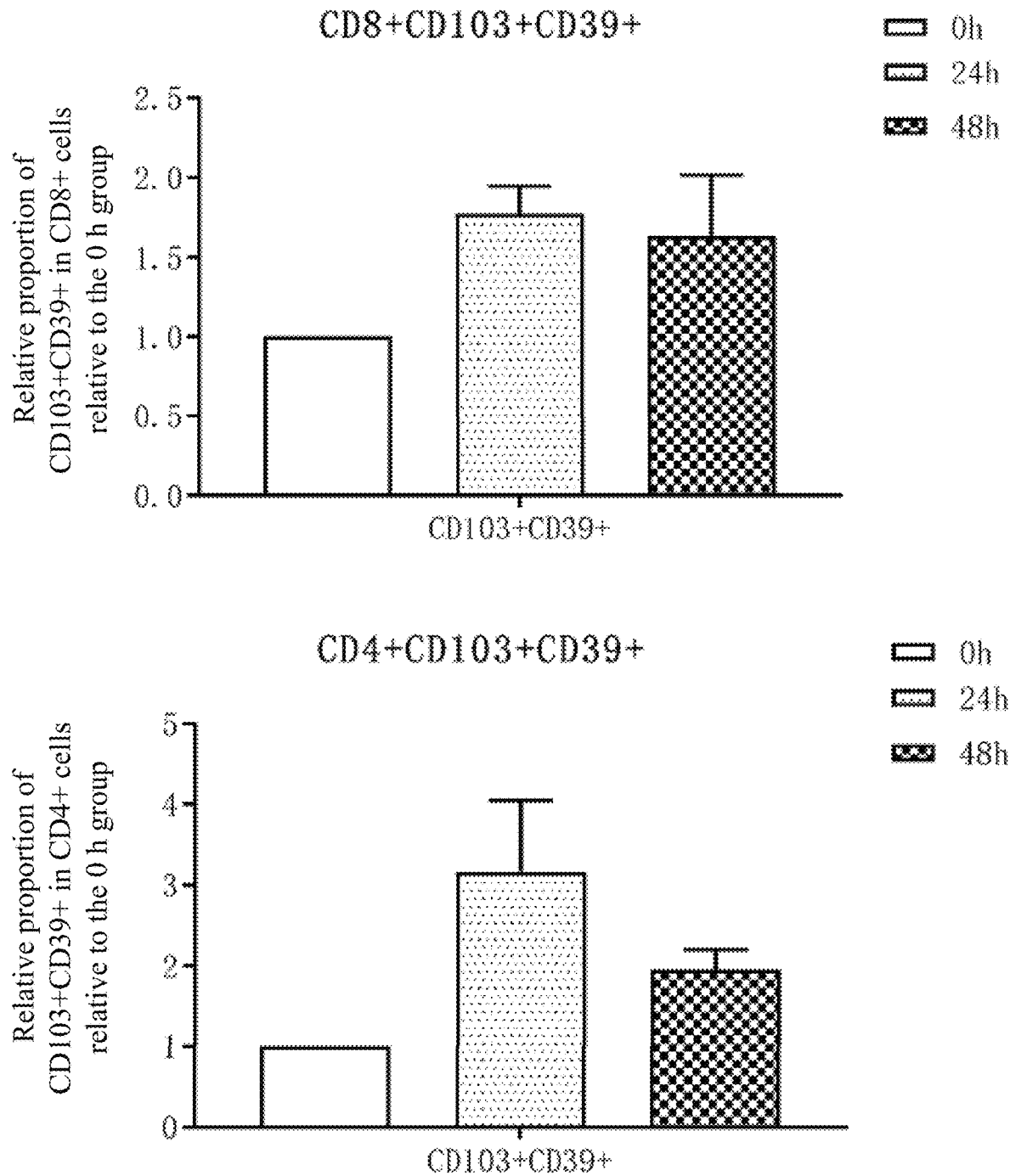
FIG. 14 shows the proportion of CD103$^+$CD39$^+$ tumor-specific T cells of TIL cells obtained by culturing TILs with feeder cells added at 0, 24 or 48 hours after addition of OKT3 and IL-2.

FIG. 14 shows the ratio of CD103$^+$CD39$^+$ tumor-specific T cells of TIL cells obtained by culturing TILs with feeder cells added at 0, 24 or 48 hours after addition of OKT3 and IL-2. The results show that the TILs cultured with the feeder cells added at 24 hours or 48 hours had higher ratio of tumor-specific T cells in CD8$^+$ or in CD4$^+$ than the TILs cultured with the feeder cells added at the same time.

Figure 15:
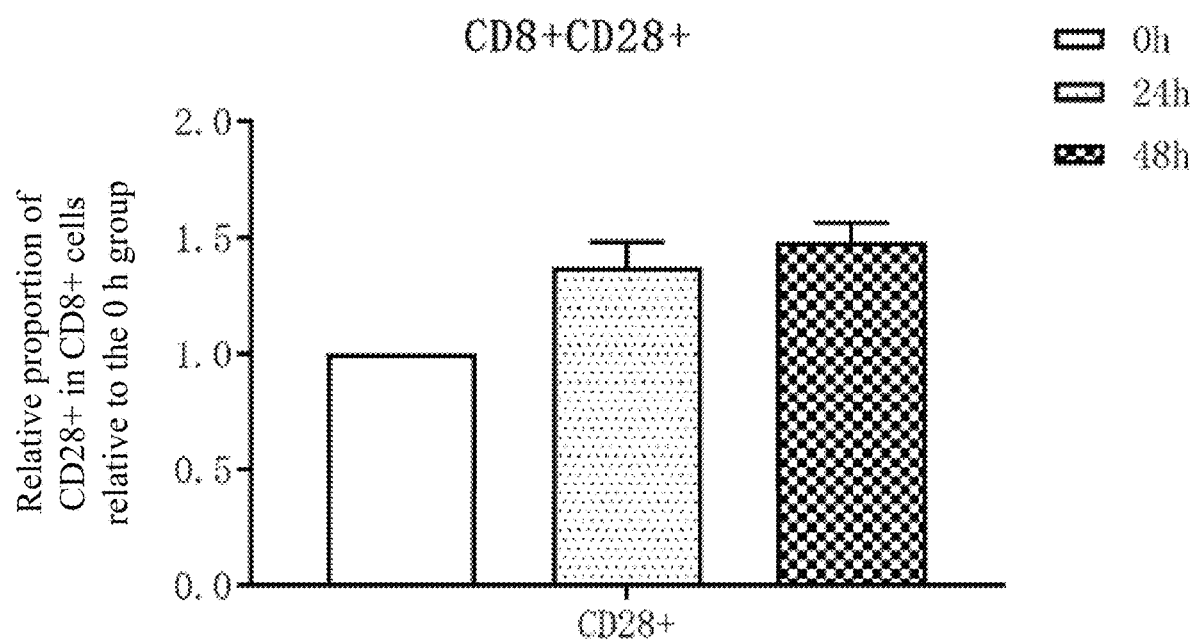
FIG. 15 shows the proportion of activated T cells (CD28$^+$) of TIL cells obtained by culturing TILs with feeder cells added at 0, 24 or 48 hours after addition of OKT3 and IL-2.

FIG. 15 shows the ratio of activated T cells (CD28$^+$) of TIL cells obtained by culturing TILs with feeder cells added at 0, 24 or 48 hours after addition of OKT3 and IL-2. The results show that the TILs cultured with the feeder cells added at 24 hours or 48 hours had higher ratio of activated T cells, for example higher ratio of CD8$^+$CD28$^+$ cells, than the TILs cultured with the feeder cells added at the same time.

Figure 16:
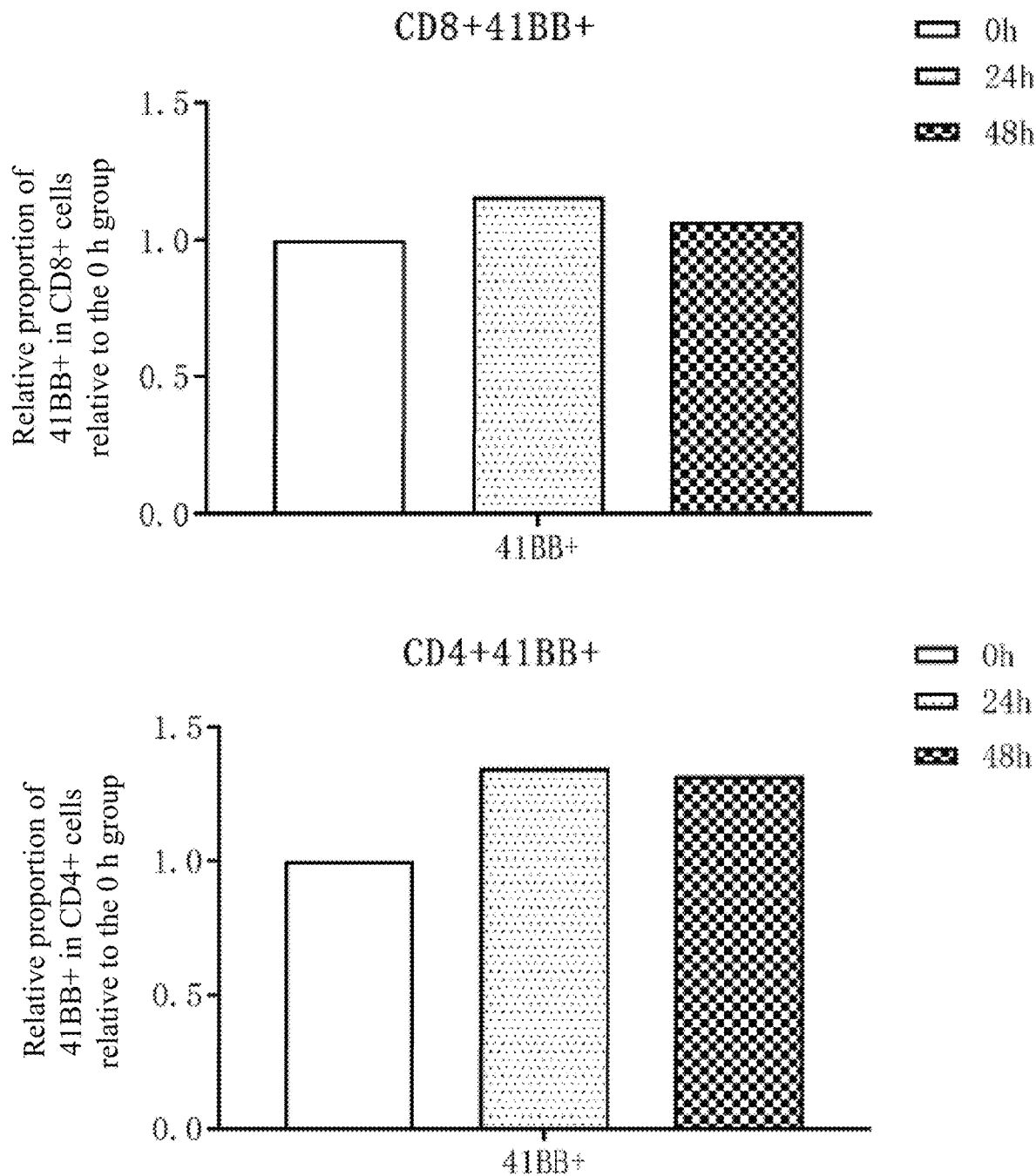
FIG. 16 shows the proportion of activated T cells (41BB$^+$) of TIL cells obtained by culturing TILs with feeder cells added at 0, 24 or 48 hours after addition of OKT3 and IL-2.

FIG. 16 shows the ratio of activated T cells (41BB$^+$) of TIL cells obtained by culturing TILs with feeder cells added at 0, 24 or 48 hours after addition of OKT3 and IL-2. The results show that the TILs cultured with the feeder cells added at 24 hours or 48 hours had higher ratio of activated T cells, for example higher ratio of 41BB$^+$cells in CD8$^+$ and/or in CD4$^+$, than the TILs cultured with the feeder cells added at the same time.

Figure 17:
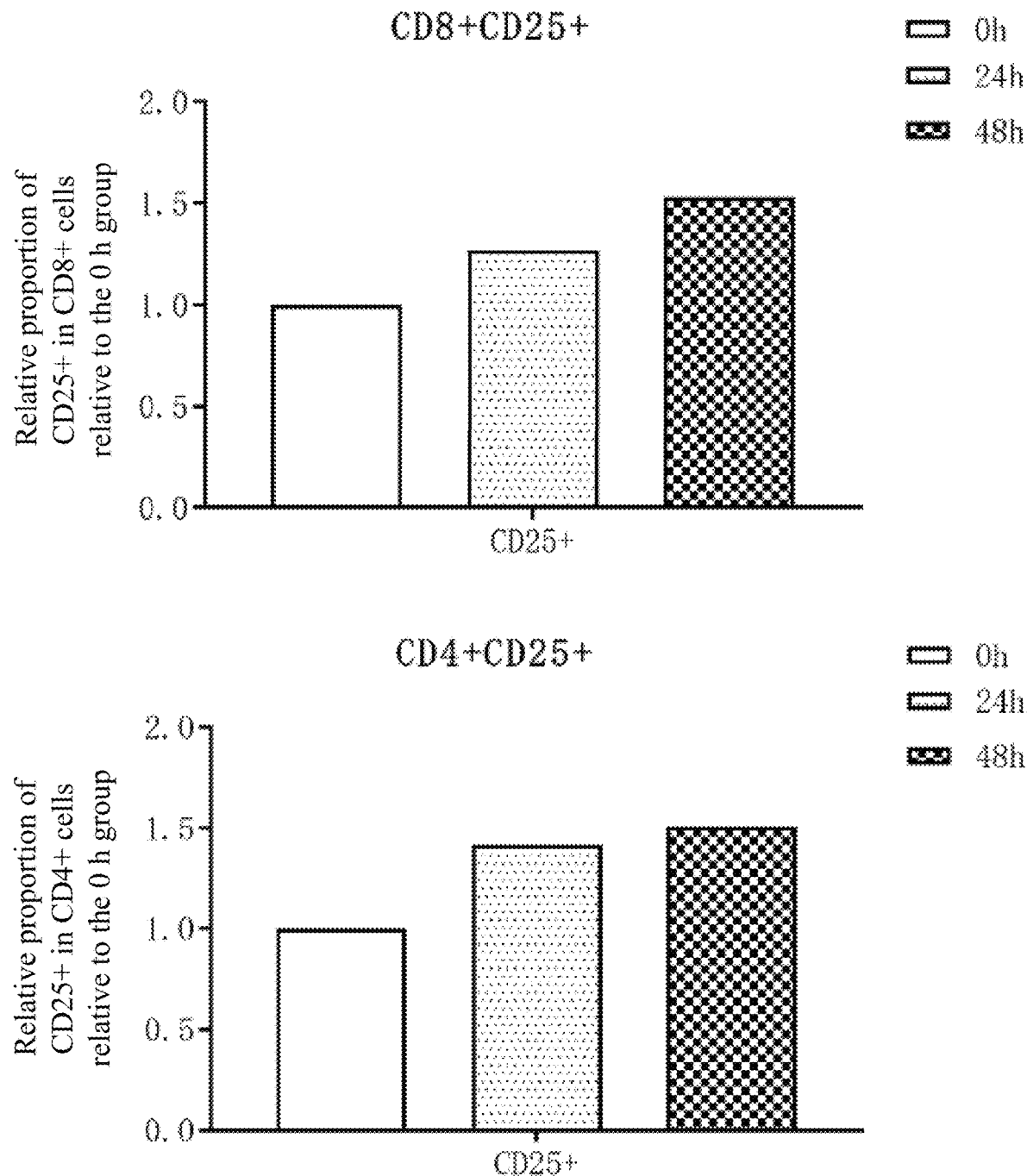
FIG. 17 shows the proportion of activated T cells (CD25$^+$) of TIL cells obtained by culturing TILs with feeder cells added at 0, 24 or 48 hours after addition of OKT3 and IL-2.

FIG. 17 shows the ratio of activated T cells (CD25$^+$) of TIL cells obtained by culturing TILs with feeder cells added at 0, 24 or 48 hours after addition of OKT3 and IL-2. The results show that the TILs cultured with the feeder cells added at 24 hours or 48 hours had higher ratio of activated T cells, for example higher ratio of CD25$^+$ cells in CD8$^+$ and/or in CD4$^+$, than the TILs cultured with the feeder cells added at the same time.

Detection of Intracellular Factor Expression

Experiment Preparation

Preparing the medium required for the detection of intracellular factor expression: T cell culture medium was taken, and CD107a antibody (BD) in a volume ratio of 1:500 was added.

Detection Steps

After centrifuging the TILs of each experiment group, they were resuspended to 1×10$^6$ cells/mL using 600 μL of above-mentioned medium required for the detection of intracellular factor expression, added into a 96-well plate in 100 μL/well, and placed in a 37° C. incubator to incubate overnight.

After the incubation was completed, they were washed once with 200 μL/well PBS, centrifuged at 600 g for 3 minutes, and the supernatant was discarded. An antibody mixed working solution (BD) was prepared for CD3/CD4/CD8 cell surface staining, with an antibody concentration of 1:100, a viability of 1:10000, a staining volume of 50 μL/group. Incubating was performed at 2-8° C. in dark for 30 minutes. After the staining was completed, the cells were washed, and resuspended in PBS for flow detection on machine.

Figure 18:
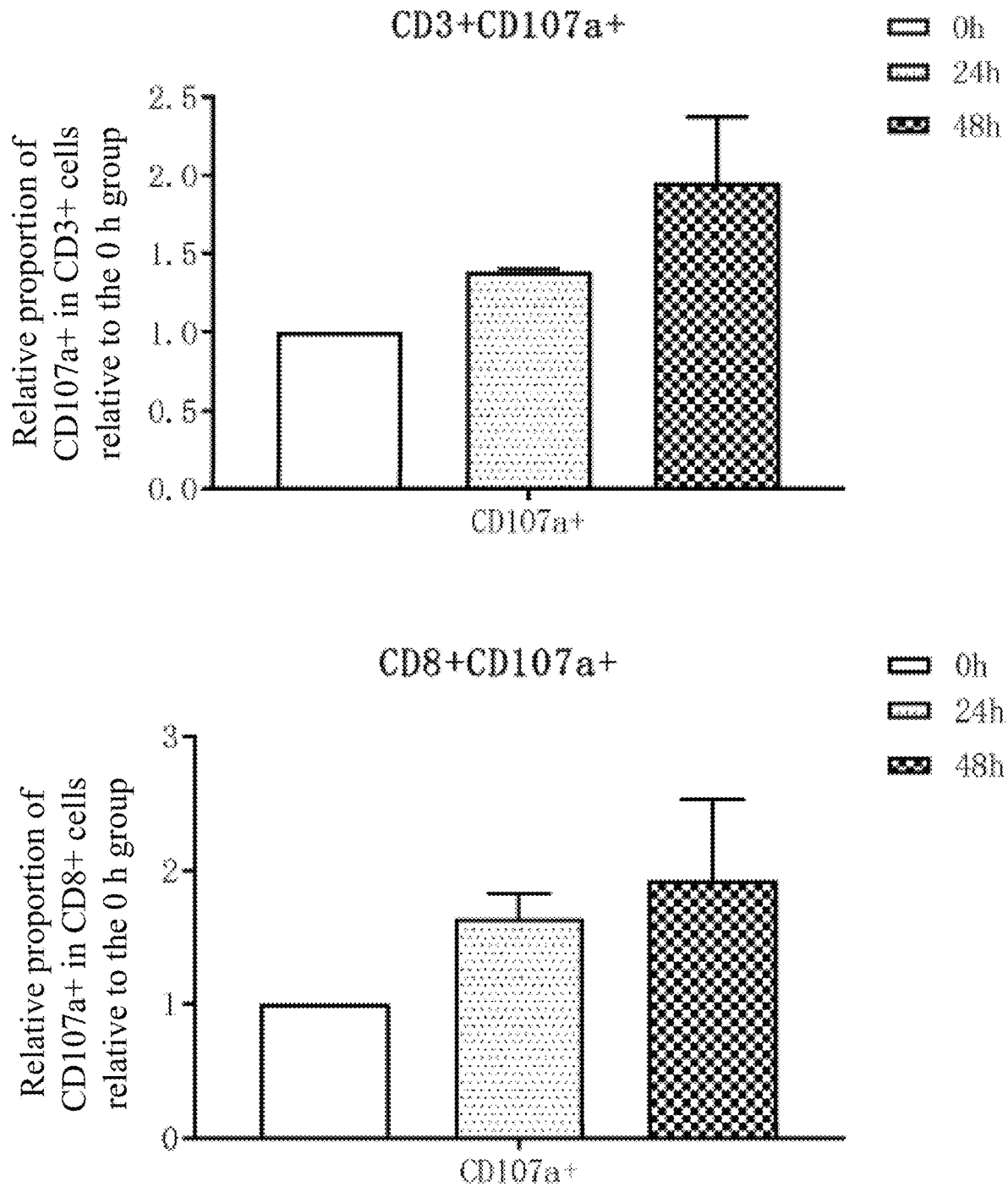
FIG. 18 shows the results of the intracellular factor expression detection of TIL cells obtained by culturing TILs with feeder cells added at 0, 24 or 48 hours after addition of OKT3 and IL-2.
Figure 18:
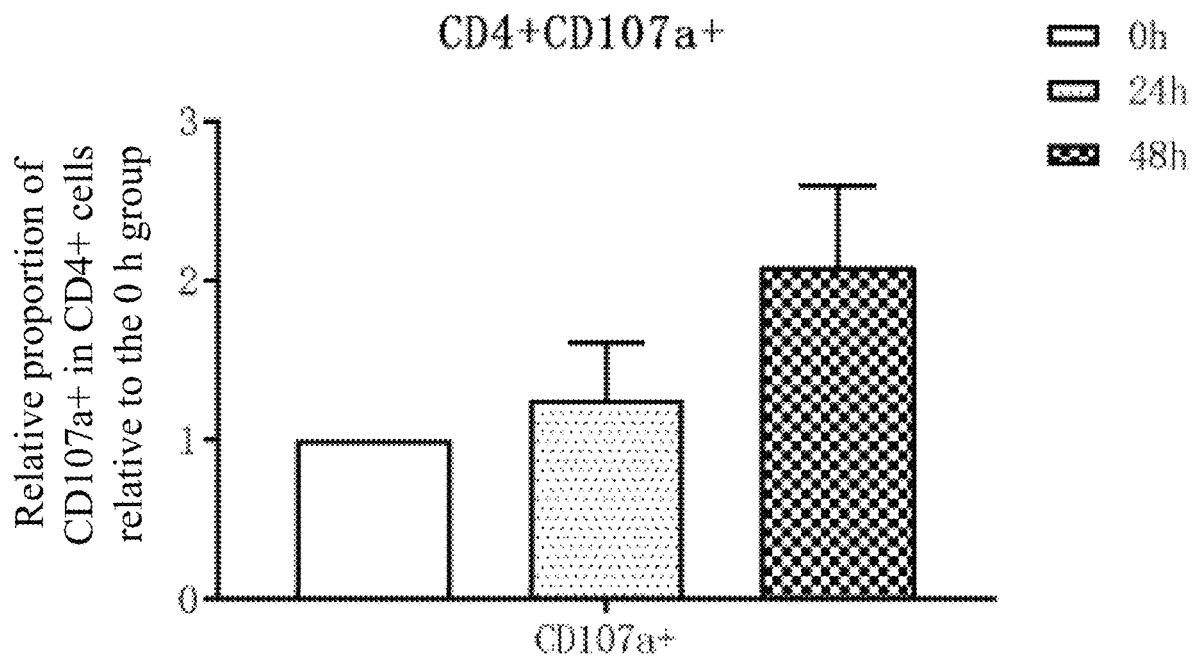

FIG. 18 shows the results of the intracellular factor expression detection of TIL cells obtained by culturing TILs with feeder cells added at 0, 24 or 48 hours after addition of OKT3 and IL-2. The results show that the TILs cultured with the feeder cells added at 24 hours or 48 hours had higher expression abilities of intracellular factors than the TILs cultured with the feeder cells added at the same time. For example, higher expression abilities of CD107a in CD3$^+$, CD8$^+$ and/or CD4$^+$.

Detection of Cytokine Secretion

The detection method of cytokine secretion can refer to the instructions of a cytokine detection kit (BD). The human Th1/Th2/Th17 cytokine standard lyophilized powders (BD) were reconstituted in 2 mL of Assay Diluent (BD) (The concentration of each cytokine in the standard stock solution was 5000 pg/mL), and serially diluted in the following order: 1:2, 1:4, 1:8, 1:16, 1:32, 1:64, 1:128, 1:256, 1:512, and 1:1024, and labeled as "standard tubes". A tube containing Assay Diluent only was taken as a reference. Each kind of Capture Beads (BD) were added at 2 L/Beads/well, then a PE Detection Reagent (BD) was added at 10 μL/well, and they were mixed to prepare a mix which was added to a V-bottom 96-well plate at 22 μL/well. Then, the supernatants of each standard and the experiment group were added at 10 μL/well and mixed, and incubated at room temperature in dark for 3 hours.

After the incubation was completed, 200 μL/well of a Wash Buffer (BD) was added and centrifuged at 500 g for 3 minutes. After the centrifugation was completed, 100 μL/well of the Wash Buffer (BD) was added to resuspend for flow analysis.

Figure 19:
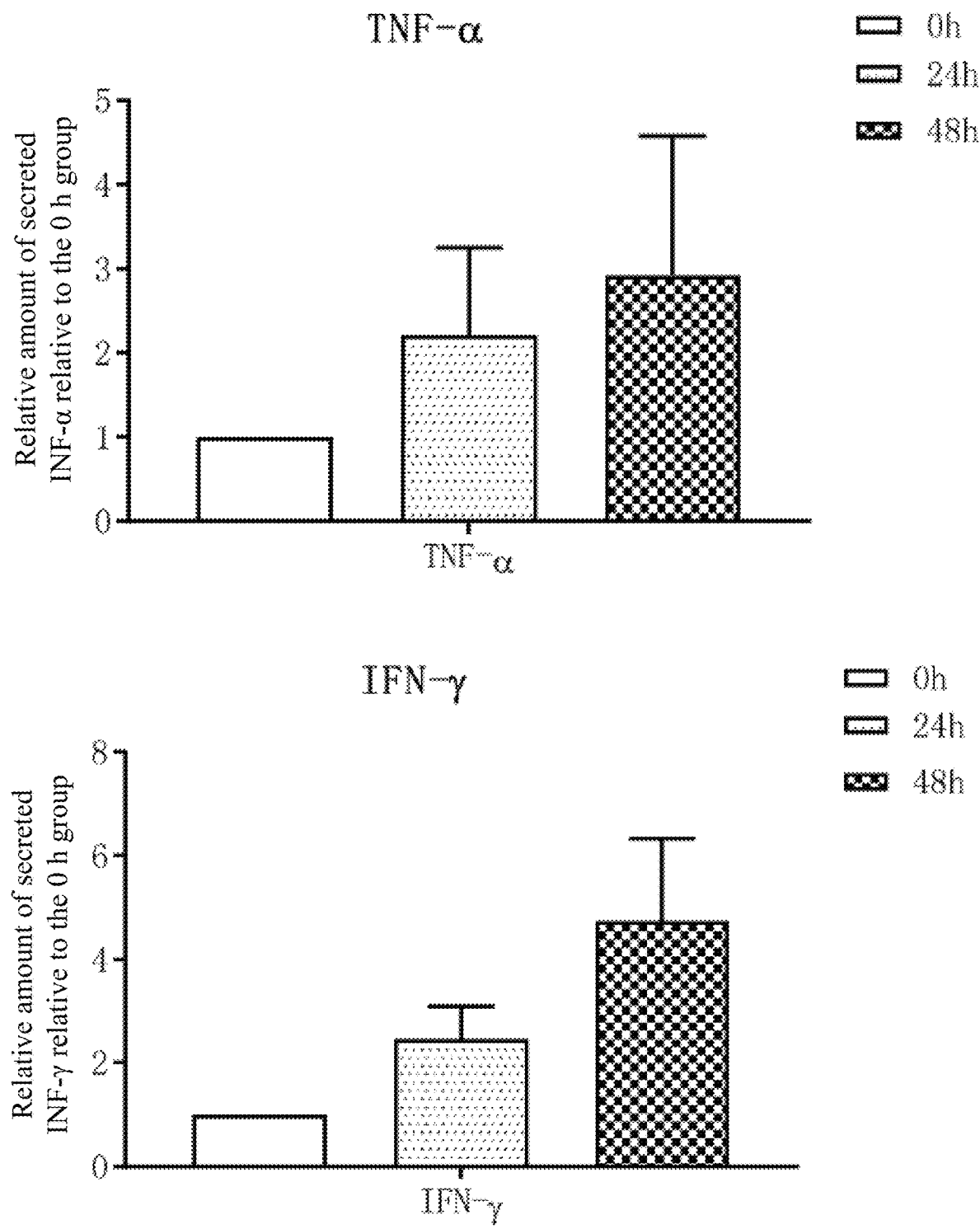
FIG. 19 shows the results of the cytokine secretion detection of TIL cells obtained by culturing TILs with feeder cells added at 0, 24 or 48 hours after addition of OKT3 and IL-2.

FIG. 19 shows the results of the cytokine secretion detection of TIL cells obtained by culturing TILs with feeder cells added at 0, 24 or 48 hours after addition of OKT3 and IL-2. The results show that the TILs cultured with the feeder cells added at 24 hours or 48 hours had higher secretion abilities of cytokines than the TILs cultured with the feeder cells added at the same time. For example, a higher TNF-α secretion ability, or a higher IFN-γ secretion ability.

Example 5 Statistics of the Results of TILs Cultured with Feeder Cells Added at Different Times In the activation of TILs subjected to second stage of expansion in 1.4 of Example 1, the amount of cells subjected to the first stage of the expansion was taken. The cell density was adjusted to 5×10$^5$ to 2×10$^6$/mL, and the cells were added into the suspension 24-well culture plate at 1 mL/well. A CD3 antibody, for example, about 30 ng/mL of OKT3 was added. IL-2 was added at a concentration of about 1000-9000 IU/mL, e.g., 3000 or 6000 IU/mL of IL-2. 0 hours, 6 hours, 12 hours, 24 hours, 48 hours, 72 hours, or 5 days after the addition of the above-mentioned OKT3 and IL-2, the feeder cells were added into the culture environment of the tumor infiltrating lymphocytes. Wherein, the TILs and the feeder cells could be added at a ratio of 1:40-1:400, e.g., 1:200. All the cells were collected after culturing for about 9-14 days in the second stage of the expansion, to detect the TILs obtained by the culture and perform statistics on the results of the TILs.

Detection of Proliferation Abilities

Cell counts were performed on the TILs obtained by culturing with feeder cells added at different times.

Figure 20:
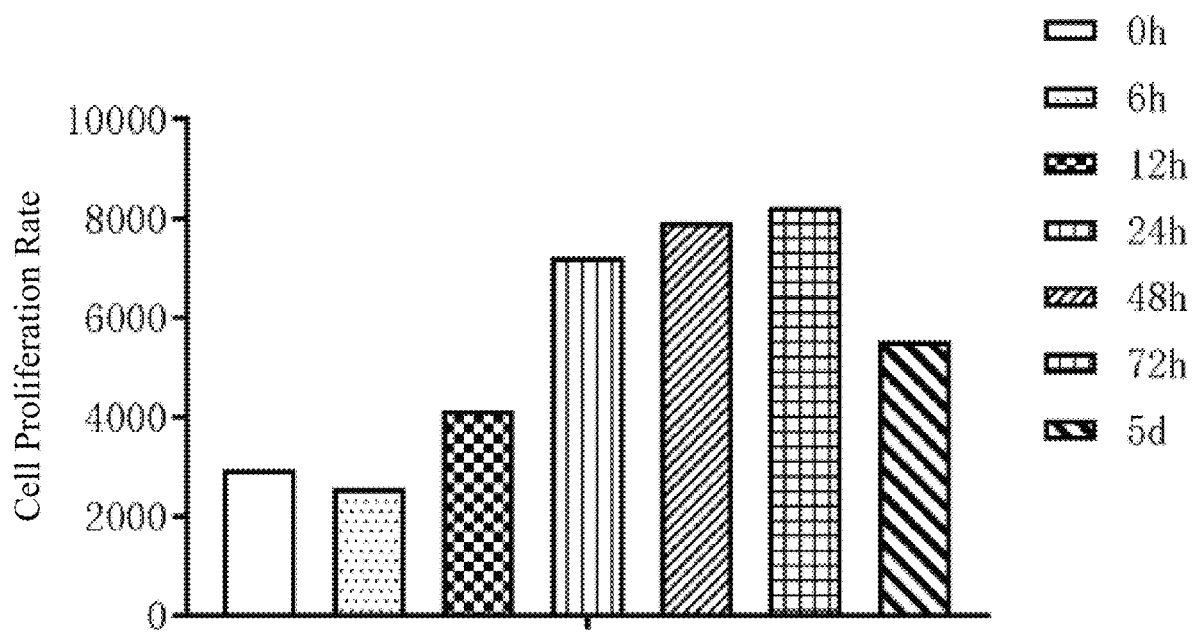
FIG. 20 is a graph showing the results of the cell proliferation abilities of TIL cells obtained by culturing TILs with feeder cells added at 0, 6, 12, 24, 48, 72 hours, or 5 days after addition of OKT3 and IL-2.

FIG. 20 is a graph showing the results of the cell proliferation abilities of TIL cells obtained by culturing TILs with feeder cells added at 0, 6, 12, 24, 48, 72 hours, or 5 days after addition of OKT3 and IL-2. The proliferation abilities of the TILs cultured with the feeder cells added after 12 hours or more after the addition of OKT3 and IL-2 were significantly enhanced relative to the TILs cultured with the feeder cells added 0 hours after (i.e., at the same time) addition of OKT3 and IL-2.

Flow Detection of TIL Cell Composition

Flow detection was performed on the TIL populations obtained by culturing with above feeder cells added at different times.

The TILs which are derived from tumors of different donors were used as different batches; the data of the experiment groups in which OKT3 and IL-2 were added with the feeder cells at the same time (0 h group) in each batch were used as benchmark 1. The data of the experiment groups at other time points in the same batch were normalized, and statistics on the cell composition ratio of each experiment group in the second stage of the expansion relative to the 0 h group was performed.

For the experiment flow of the flow detection, reference can be made to the content of example 3 of the present application.

Figure 21:
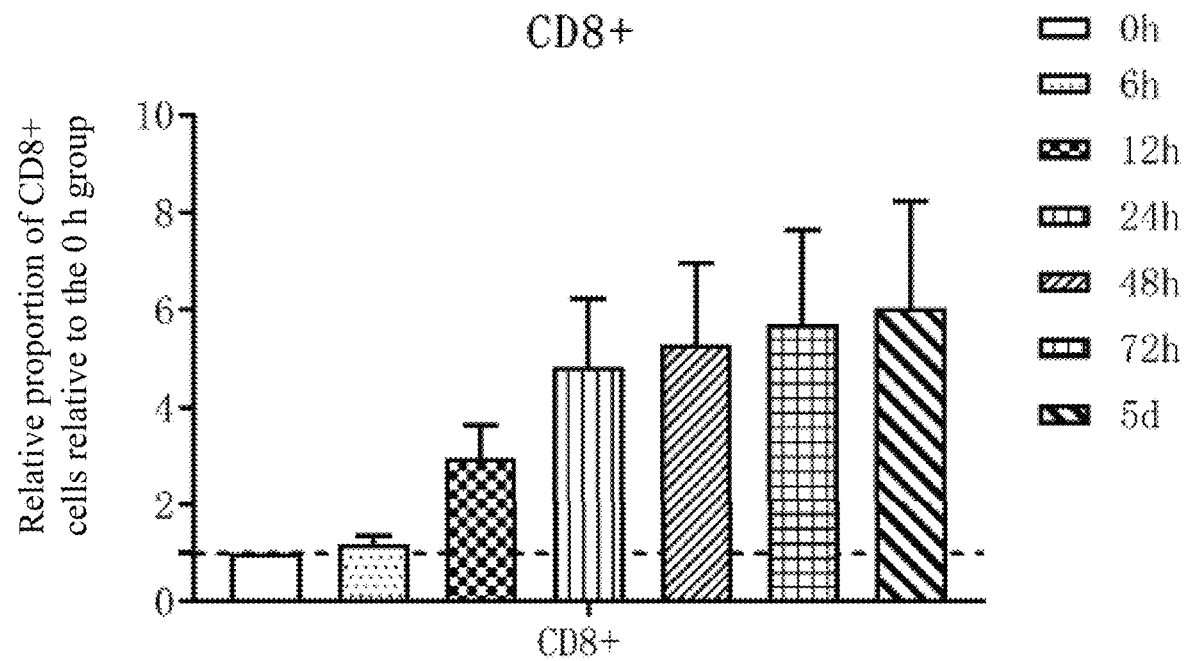
FIG. 21 shows the proportion of CD8$^+$ T cells of TIL cells obtained by culturing TILs with feeder cells added at 0, 6, 12, 24, 48, 72 hours, or 5 days after addition of OKT3 and IL-2.

FIG. 21 shows the ratio of CD8$^+$ T cells of TIL cells obtained by culturing TILs with feeder cells added at 0, 6, 12, 24, 48, 72 hours, or 5 days after addition of OKT3 and IL-2. The results show that the ratio of the CD8$^+$ T cells of the TILs cultured with the feeder cells added 12 hours or more after addition of OKT3 and IL-2 were higher relative to the TILs cultured with the feeder cells added at the same time with the addition of OKT3 and IL-2.

Figure 22:
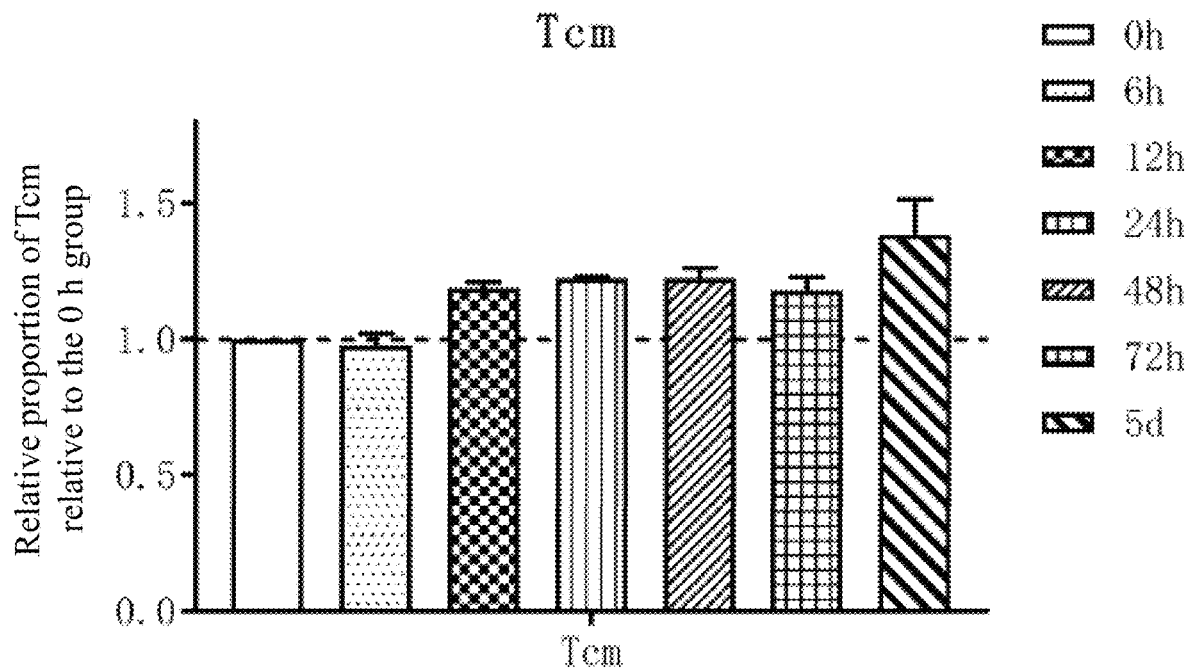
FIG. 22 shows the proportion of CD45RO$^+$CD62L$^+$T cells of TIL cells obtained by culturing TILs with feeder cells added at 0, 6, 12, 24, 48, 72 hours, or 5 days after addition of OKT3 and IL-2.

FIG. 22 shows the ratio of CD45RO$^+$CD62L$^+$T cells of TIL cells obtained by culturing TILs with feeder cells added at 0, 6, 12, 24, 48, 72 hours, or 5 days after addition of OKT3 and IL-2. The results show that the ratio of the memory T cells(Tcm, CD45RO$^+$CD62L$^+$) of the TILs cultured with the feeder cells added 12 hours or more after addition of OKT3 and IL-2 were higher relative to the TILs cultured with the feeder cells added at the same time with the addition of OKT3 and IL-2.

Figure 23:
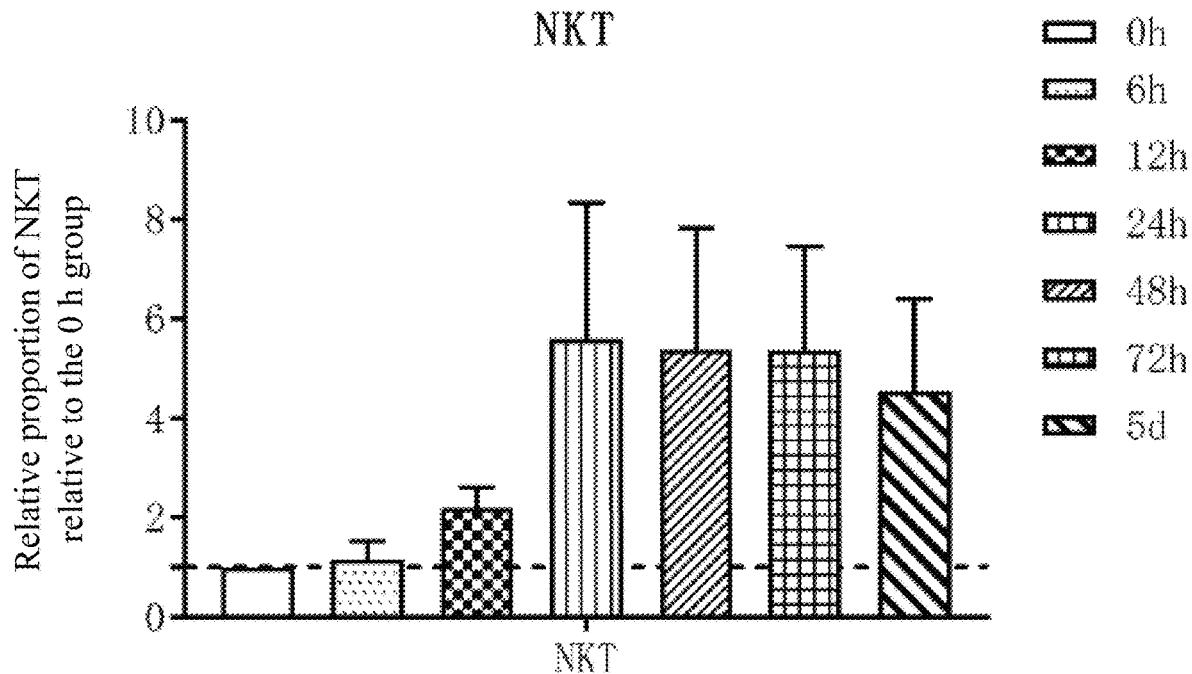
FIG. 23 shows the proportion of NK T cells of TIL cells obtained by culturing TILs with feeder cells added at 0, 6, 12, 24, 48, 72 hours, or 5 days after addition of OKT3 and IL-2.

FIG. 23 shows the ratio of NK T cells of TIL cells obtained by culturing TILs with feeder cells added at 0, 6, 12, 24, 48, 72 hours, or 5 days after addition of OKT3 and IL-2. The results show that the ratio of the NK T cells of the TILs cultured with the feeder cells added 12 hours or more after the addition of OKT3 and IL-2 were higher relative to the TILs cultured with the feeder cells added at the same time with the addition of OKT3 and IL-2.

Figure 24:
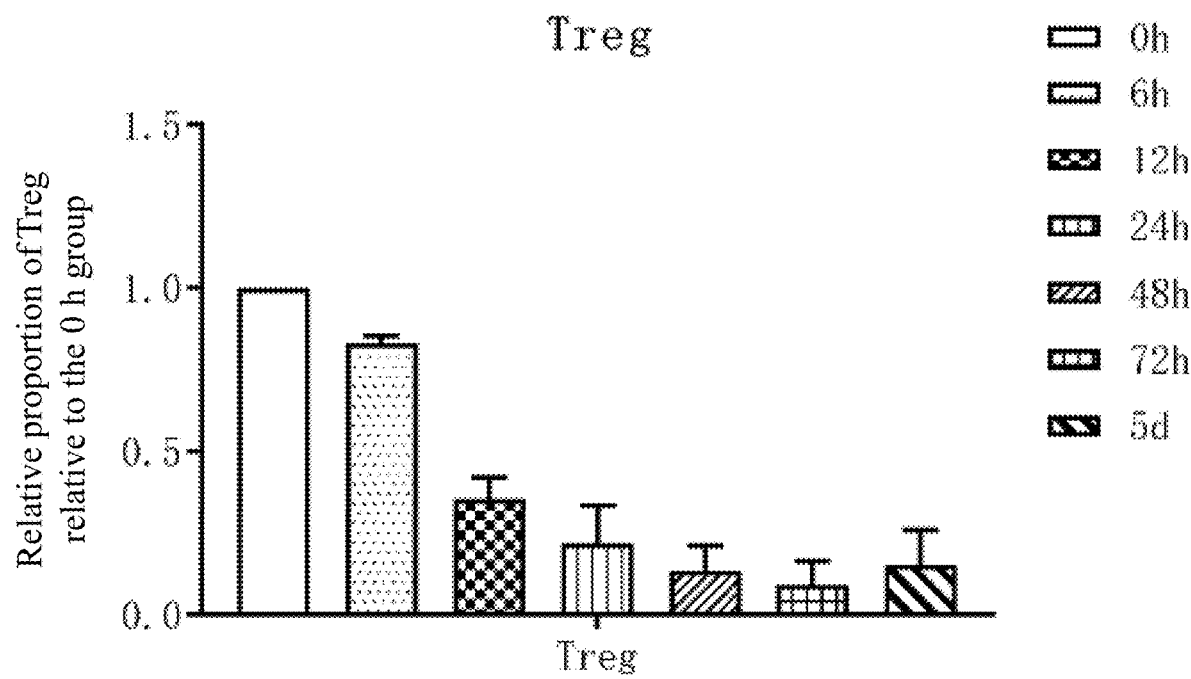
FIG. 24 shows the proportion of CD4$^+$CD25$^+$Foxp3$^+$ regulatory T cells (Treg) of TIL cells obtained by culturing TILs with feeder cells added at 0, 6, 12, 24, 48, 72 hours, or 5 days after addition of OKT3 and IL-2.

FIG. 24 shows the ratio of CD4$^+$CD25$^+$Foxp3$^+$ regulatory T cells (Treg) of TIL cells obtained by culturing TILs with feeder cells added at 0, 6, 12, 24, 48, 72 hours, or 5 days after addition of OKT3 and IL-2. The results show that the ratio of the regulatory T cells of the TILs cultured with the feeder cells added 12 hours or more after the addition of OKT3 and IL-2 were lower relative to the TILs cultured with the feeder cells added at the same time with the addition of OKT3 and IL-2.

Example 6 Detection of Killing Abilities of TILs Cultured in the Present Application For the activation of TILs subjected to second stage of expansion in 1.4 of Example 1, the amount of cells subjected to the first stage of the expansion was taken. The cell density was adjusted to $5 \times 10^5$ to $2 \times 10^6$/mL, and the cells were added into the suspension 24-well culture plate at 1 mL/well. A CD3 antibody, for example, about 30 ng/mL of OKT3 was added. IL-2 was added at a concentration of about 1000-9000 IU/mL, e.g., 3000 or 6000 IU/mL of IL-2. After 12 hours to 14 days, e.g., 48 hours after the addition of the above-mentioned OKT3 and IL-2, the feeder cells were added into the culture environment of the tumor infiltrating lymphocytes. Wherein, the TILs and the feeder cells could be added at a ratio of 1:40-1:400. All the cells were collected after culturing for about 9-14 days in the second stage of the expansion, to detect the cell killing abilities of the TILs obtained by the culture and perform statistics on the detection of the cell killing abilities.

Cell Preparation

TILs obtained from each experiment group for detection and target cells (e.g., A375 melanoma cells and/or Hela cervical cancer cells) for co-culture were prepared.

Detection Steps labeling the tumor cells with CFSE (5(6)-Carboxyfluorescein diacetate N-succinimidyl ester, Sigma, 21888-25MG-F): The tumor cells were washed with PBS. The tumor cells were resuspended in 500 μL of PBS; CFSE was added into 500 μL of PBS, and mixed with 500 μL resuspension of the tumor cells in PBS, with a final concentration of CFSE of 0.5 μmol/L. After incubation at 37° C. for 6 minutes, the medium containing 10% FBS was added to wash. Centrifugation was performed at 600 g for 5 minutes. X-vivo 15 medium or other commercially available T cell culture media, e.g. T cell culture media of Stem Cell, Lonza, Thermo, Miltenyi brands etc., were used to resuspend the tumor cells at a concentration of $1 \times 10^6$ cells/mL. The TIL population of each experiment group was centrifuged at 600 g for 5 minutes, and the TIL cells were resuspended according to the effector-target ratio (the ratio of TIL cells to tumor cells) of 3:1 (i.e., the concentration of the resuspended TIL cells was $3 \times 10^6$ cells/mL). 100 μL of the tumor cells and the TIL cells were added to a U-bottom 96-well plate (Corning) individually, and three replicate wells were set up in each group. At the same time, a control group containing only the tumor cells was set up. The plate was centrifuged at 200 g for 1 minute and incubated at 37° C. for 4 hours to overnight. Among them, when the TILs were co-cultured with the tumor cells, those without substances activating the TIL cells could be regarded as the non-activated groups, or those with transACT (Miltenyi, a nanomatrix material containing a CD3 antibody and a CD28 antibody) added could be regarded as activated groups.

After the incubation was completed, centrifugation was performed at 600 g for 3 minutes and the supernatant was discarded. Trypsin was added at 20 μL/well. Incubation was performed in an incubator at 37° C. for 3-5 minutes to digest the tumor cells. After the digestion was completed, 180 μL of medium containing 10% FBS was added to terminate the digestion. Dapi (Biyuntian, C0060) was diluted 1:100, and then the diluted Dapi was added at 20 μL/well. Flow detection on machine was carried out.

The killing rate %=the number of Dapi$^+$CFSE$^+$ cell/total CFSE$^+ \times 100\%$, or the killing rate can be represented by the number of Dapi+ cells/total tumor cell number.

Figure 25:
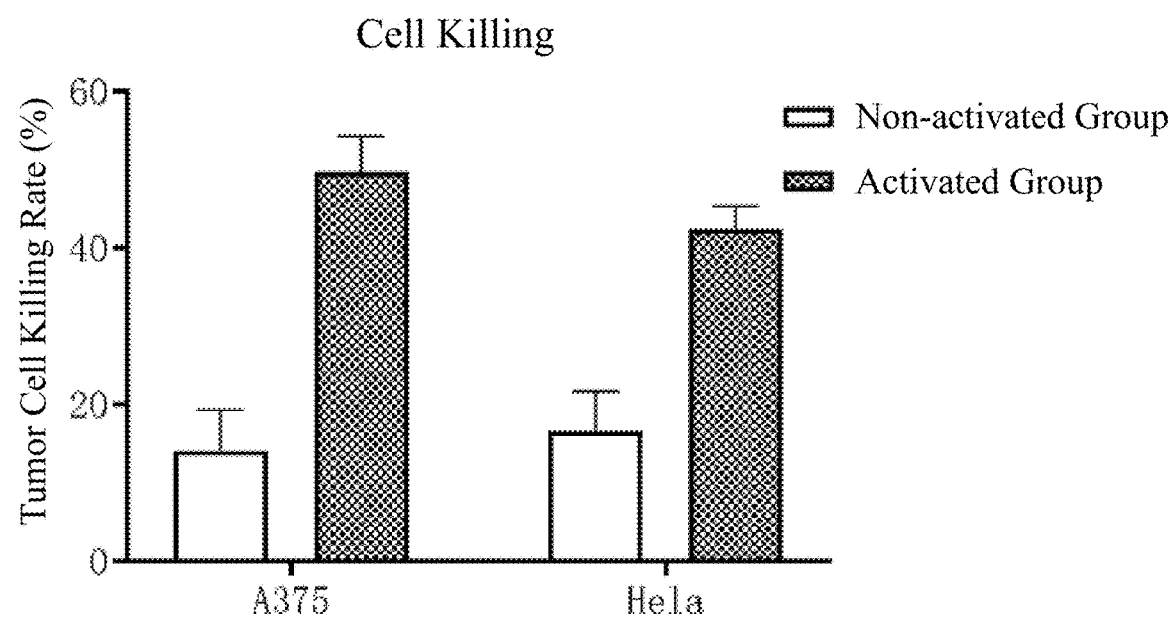
FIG. 25 shows the results of the cell killing abilities of TIL cells obtained by culturing TILs with feeder cells added at 48 hours after addition of OKT3 and IL-2.

FIG. 25 shows the results of the cell killing abilities of TIL cells obtained by culturing TILs with feeder cells added at 48 hours after addition of OKT3 and IL-2. The results show that the TILs cultured with the feeder cells added 48 hours after the addition of OKT3 and IL-2 all have significant tumor cell killing abilities, e.g., melanoma and/or cervical tumors.

The foregoing detailed description is provided in an illustrative and exemplary manner, and is not intended to limit the scope of the appended claims. Various modifications of embodiments currently listed herein are apparent for those skilled in the art, and are encompassed within the scope of the appended claims and their equivalents.

What is claimed is:

1. A method for culturing tumor infiltrating lymphocytes (TILs), wherein the method comprises subjecting TILs that are derived from tumor tissues and not expanded in vitro to at least one stage of in vitro expansion, and wherein a single stage of the in vitro expansion comprises co-culturing non-in vitro-expanded or in vitro-expanded TILs with feeder cells after contacting the non-in vitro-expanded or in vitro-expanded TILs with one or more T cell co-stimulatory molecules and one or more T cell growth factors for a period of time, wherein the period of time is 12 hours or more.

2. The method according to claim 1, wherein the method comprises subjecting the TILs that are derived from the tumor tissues and not expanded in vitro to at least two stages of the in vitro expansion, and wherein the second stage of the in vitro expansion comprises co-culturing in vitro-expanded TILs with the feeder cells after contacting the in vitro-expanded TILs with the one or more T cell co-stimulatory molecules and the one or more T cell growth factors for the period of time.

3. The method according to claim 1, wherein the period of time is about 12 to 72 hours.

4. The method according to claim 1, wherein the period of time is about 12 to 48 hours.

5. The method according to claim 1, wherein the period of time is about 12, 24, 48 or 72 hours.

6. The method according to claim 1, wherein the one or more T cell co-stimulatory molecules are one or more of the molecules selected from the group consisting of: CD80, CD86, B7-H3, 4-1BBL, CD27, CD30, CD134, B7h, CD40, LIGHT, an antibody that specifically binds to CD3, an antibody that specifically binds to CD28, an antibody that specifically binds to HVEM, an antibody that specifically binds to CD40L, an antibody that specifically binds to OX40, and an antibody that specifically binds to 4-1BB.

7. The method according to claim 1, wherein the one or more T cell co-stimulatory molecules comprise an antibody and/or an antigen-binding fragment thereof that specifically binds to CD3.

8. The method according to claim 1, wherein the one or more T cell growth factors are one or more of the factors selected from the group consisting of: IL-2, IL-4, IL-7, IL-10, IL-12, IL-15, IL-21, and interferon gamma.

9. The method according to claim 1, wherein the one or more T cell growth factors comprise IL-2 and/or a functionally active fragment thereof.

10. The method according to claim 9, wherein the one or more T cell growth factors comprise an engineered cell expressing the IL-2 and/or functionally active fragment thereof, a nanoparticle comprising the IL-2 and/or functionally active fragment thereof, or a polymer comprising the IL-2 and/or functionally active fragment thereof.

11. The method according to claim 9, wherein the one or more T cell growth factors comprise IL-2 and the initial concentration of IL-2 in the cell culture medium of the TILs is at least 1000 IU/mL.

12. The method according to claim 1, wherein the one or more T cell co-stimulatory molecules comprise an antibody and/or an antigen-binding fragment thereof that specifically binds to CD3, and the one or more T cell growth factors comprise IL-2 and/or a functionally active fragment thereof.

13. The method according to claim 12, wherein the one or more T cell growth factors comprise an engineered cell expressing the IL-2 and/or functionally active fragment thereof, a nanoparticle comprising the IL-2 and/or functionally active fragment thereof, or a polymer comprising the IL-2 and/or functionally active fragment thereof.

14. The method according to claim 12, wherein the one or more T cell growth factors comprise IL-2 and the initial concentration of IL-2 in the cell culture medium of the TILs is at least 1000 IU/mL.

15. The method according to claim 1, wherein the feeder cells comprise antigen presenting cells.

16. The method according to claim 1, wherein the feeder cells are peripheral mononuclear cells.

17. The method according to claim 1, wherein the feeder cells are dendritic cells or artificial antigen presenting cells.

18. The method according to claim 1, wherein the feeder cells are irradiated feeder cells.

19. The method according to claim 1, wherein the step of co-culturing comprises adding the feeder cells into the cell culture medium of the TILs.

20. The method according to claim 1, wherein the period of time is about 24 hours.

21. The method according to claim 1, wherein the period of time is about 48 hours.

22. The method according to claim 1, wherein the period of time is about 72 hours.

23. The method according to claim 1, wherein the period of time is about 4 days.

24. The method according to claim 1, wherein the period of time is about 5 days.

* * * * *